US008632462B2

(12) United States Patent
Yoo et al.

(10) Patent No.: US 8,632,462 B2
(45) Date of Patent: *Jan. 21, 2014

(54) TRANS-RECTUM UNIVERSAL PORTS

(75) Inventors: Andrew Yoo, Cincinnati, OH (US);
Edward G. Chekan, Cincinnati, OH
(US); Frederick E. Shelton, IV,
Hillsboro, OH (US); Steven G. Hall,
Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 111 days.

This patent is subject to a terminal disclaimer.

(21) Appl. No.: 13/181,801

(22) Filed: Jul. 13, 2011

(65) Prior Publication Data

US 2012/0238826 A1 Sep. 20, 2012

Related U.S. Application Data

(60) Provisional application No. 61/452,432, filed on Mar. 14, 2011.

(51) Int. Cl.
*A61B 1/32* (2006.01)

(52) U.S. Cl.
USPC .......................................... 600/208

(58) Field of Classification Search
USPC ......... 600/235, 208, 224, 210, 214, 215, 217, 600/219, 222, 234, 184; 606/151, 153, 219
See application file for complete search history.

(56) References Cited

U.S. PATENT DOCUMENTS

| | | | |
|---|---|---|---|
| 3,166,072 A | 1/1965 | Sullivan, Jr. | |
| 3,863,639 A | 2/1975 | Kleaveland | |
| 4,274,398 A | 6/1981 | Scott, Jr. | |
| 4,505,272 A | 3/1985 | Utyamyshev et al. | |
| 4,893,622 A | 1/1990 | Green et al. | |
| 4,903,697 A | 2/1990 | Resnick et al. | |
| 4,984,564 A | 1/1991 | Yuen | |
| 5,071,430 A | 12/1991 | de Salis et al. | |
| 5,104,025 A | 4/1992 | Main et al. | |
| 5,122,156 A | 6/1992 | Granger et al. | |
| 5,139,513 A | 8/1992 | Segato | |

(Continued)

FOREIGN PATENT DOCUMENTS

| | | |
|---|---|---|
| CA | 2458946 A1 | 3/2003 |
| CA | 2512960 A1 | 1/2006 |

(Continued)

OTHER PUBLICATIONS

Disclosed Anonymously, "Motor-Driven Surgical Stapler Improvements," Research Disclosure Database No. 526041, Published: Feb. 2008.

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.

(Continued)

*Primary Examiner* — Pedro Philogene

(57) ABSTRACT

Various universal ports for installation into a colon are disclosed. Various embodiments include expandable port bodies that may employ selectively deployable tissue-engaging barbs for securing the port in position within the colon. Some embodiments also employ tissue cutting members that may be deployed to sever the colon. Some embodiments also employ a flexible sleeve that may extend from the port out through the anus to provide a passageway for passing surgical instruments and into and out of the rectum and also for removing severed specimens therefrom.

24 Claims, 52 Drawing Sheets

(56) References Cited

U.S. PATENT DOCUMENTS

| | | |
|---|---|---|
| 5,158,567 A | 10/1992 | Green |
| 5,205,459 A | 4/1993 | Brinkerhoff et al. |
| 5,222,963 A | 6/1993 | Brinkerhoff et al. |
| 5,222,975 A | 6/1993 | Crainich |
| 5,234,447 A | 8/1993 | Kaster et al. |
| 5,236,440 A | 8/1993 | Hlavacek |
| 5,258,009 A | 11/1993 | Conners |
| 5,282,829 A | 2/1994 | Hermes |
| 5,285,945 A | 2/1994 | Brinkerhoff et al. |
| 5,304,204 A | 4/1994 | Bregen |
| 5,309,927 A | 5/1994 | Welch |
| 5,336,232 A | 8/1994 | Green et al. |
| 5,342,395 A | 8/1994 | Jarrett et al. |
| 5,342,396 A | 8/1994 | Cook |
| 5,350,400 A | 9/1994 | Esposito et al. |
| 5,366,479 A | 11/1994 | McGarry et al. |
| 5,404,870 A | 4/1995 | Brinkerhoff et al. |
| 5,411,508 A | 5/1995 | Bessler et al. |
| 5,425,745 A | 6/1995 | Green et al. |
| 5,445,644 A | 8/1995 | Pietrafitta et al. |
| 5,474,057 A | 12/1995 | Makower et al. |
| 5,478,354 A | 12/1995 | Tovey et al. |
| 5,503,635 A | 4/1996 | Sauer et al. |
| 5,520,609 A | 5/1996 | Moll et al. |
| 5,527,264 A | 6/1996 | Moll et al. |
| 5,549,621 A | 8/1996 | Bessler et al. |
| 5,554,169 A | 9/1996 | Green et al. |
| 5,562,690 A | 10/1996 | Green et al. |
| 5,571,285 A | 11/1996 | Chow et al. |
| 5,575,803 A | 11/1996 | Cooper et al. |
| 5,613,937 A | 3/1997 | Garrison et al. |
| 5,618,307 A * | 4/1997 | Donlon et al. ............... 606/205 |
| 5,620,452 A | 4/1997 | Yoon |
| 5,651,762 A | 7/1997 | Bridges |
| 5,653,721 A | 8/1997 | Knodel et al. |
| 5,667,517 A | 9/1997 | Hooven |
| 5,667,527 A | 9/1997 | Cook |
| 5,681,341 A | 10/1997 | Lunsford et al. |
| 5,683,349 A | 11/1997 | Makower et al. |
| 5,695,504 A | 12/1997 | Gifford, III et al. |
| 5,695,524 A | 12/1997 | Kelley et al. |
| 5,697,943 A | 12/1997 | Sauer et al. |
| 5,702,409 A | 12/1997 | Rayburn et al. |
| 5,725,554 A | 3/1998 | Simon et al. |
| 5,730,758 A | 3/1998 | Allgeyer |
| 5,738,629 A | 4/1998 | Moll et al. |
| 5,752,965 A | 5/1998 | Francis et al. |
| 5,766,188 A | 6/1998 | Igaki |
| 5,769,892 A | 6/1998 | Kingwell |
| 5,810,721 A | 9/1998 | Mueller et al. |
| 5,810,855 A | 9/1998 | Rayburn et al. |
| 5,814,057 A | 9/1998 | Oi et al. |
| 5,839,639 A | 11/1998 | Sauer et al. |
| 5,860,581 A | 1/1999 | Robertson et al. |
| 5,964,774 A | 10/1999 | McKean et al. |
| 6,024,748 A | 2/2000 | Manzo et al. |
| 6,063,097 A | 5/2000 | Oi et al. |
| 6,083,234 A | 7/2000 | Nicholas et al. |
| 6,083,242 A | 7/2000 | Cook |
| 6,099,551 A | 8/2000 | Gabbay |
| 6,142,933 A | 11/2000 | Longo et al. |
| 6,171,330 B1 | 1/2001 | Benchetrit |
| 6,248,117 B1 | 6/2001 | Blatter |
| 6,258,107 B1 | 7/2001 | Balázs et al. |
| 6,325,810 B1 | 12/2001 | Hamilton et al. |
| 6,338,737 B1 | 1/2002 | Toledano |
| 6,346,077 B1 | 2/2002 | Taylor et al. |
| 6,387,113 B1 | 5/2002 | Hawkins et al. |
| 6,391,038 B2 | 5/2002 | Vargas et al. |
| 6,398,797 B2 | 6/2002 | Bombard et al. |
| 6,402,766 B2 | 6/2002 | Bowman et al. |
| RE37,814 E | 8/2002 | Allgeyer |
| 6,436,110 B2 | 8/2002 | Bowman et al. |
| 6,440,146 B2 | 8/2002 | Nicholas et al. |
| 6,443,973 B1 | 9/2002 | Whitman |
| 6,503,257 B2 | 1/2003 | Grant et al. |
| 6,503,259 B2 | 1/2003 | Huxel et al. |
| 6,517,565 B1 | 2/2003 | Whitman et al. |
| 6,517,566 B1 | 2/2003 | Hovland et al. |
| 6,551,333 B2 | 4/2003 | Kuhns et al. |
| 6,582,364 B2 | 6/2003 | Butler et al. |
| 6,592,597 B2 | 7/2003 | Grant et al. |
| 6,616,686 B2 | 9/2003 | Coleman et al. |
| 6,629,988 B2 | 10/2003 | Weadock |
| 6,638,285 B2 | 10/2003 | Gabbay |
| 6,638,297 B1 | 10/2003 | Huitema |
| 6,645,201 B1 | 11/2003 | Utley et al. |
| 6,656,193 B2 | 12/2003 | Grant et al. |
| 6,692,507 B2 | 2/2004 | Pugsley et al. |
| 6,716,233 B1 | 4/2004 | Whitman |
| 6,726,697 B2 | 4/2004 | Nicholas et al. |
| 6,736,825 B2 | 5/2004 | Blatter et al. |
| 6,769,590 B2 | 8/2004 | Vresh et al. |
| 6,821,284 B2 | 11/2004 | Sturtz et al. |
| 6,872,214 B2 | 3/2005 | Sonnenschein et al. |
| 6,913,608 B2 | 7/2005 | Liddicoat et al. |
| 6,939,358 B2 | 9/2005 | Palacios et al. |
| 6,960,220 B2 | 11/2005 | Marino et al. |
| 6,981,978 B2 | 1/2006 | Gannoe |
| 7,052,454 B2 | 5/2006 | Taylor |
| 7,056,330 B2 | 6/2006 | Gayton |
| 7,063,712 B2 | 6/2006 | Vargas et al. |
| 7,066,944 B2 | 6/2006 | Laufer et al. |
| 7,077,856 B2 | 7/2006 | Whitman |
| 7,108,701 B2 | 9/2006 | Evens et al. |
| 7,108,709 B2 | 9/2006 | Cummins |
| 7,128,748 B2 | 10/2006 | Mooradian et al. |
| 7,156,863 B2 | 1/2007 | Sonnenschein et al. |
| 7,179,267 B2 | 2/2007 | Nolan et al. |
| 7,220,272 B2 | 5/2007 | Weadock |
| 7,229,408 B2 | 6/2007 | Douglas et al. |
| 7,238,195 B2 | 7/2007 | Viola |
| 7,267,679 B2 | 9/2007 | McGuckin, Jr. et al. |
| 7,328,828 B2 | 2/2008 | Ortiz et al. |
| 7,354,447 B2 | 4/2008 | Shelton, IV et al. |
| 7,377,928 B2 | 5/2008 | Zubik et al. |
| 7,407,078 B2 | 8/2008 | Shelton, IV et al. |
| 7,416,101 B2 | 8/2008 | Shelton, IV et al. |
| 7,422,139 B2 | 9/2008 | Shelton, IV et al. |
| 7,431,189 B2 | 10/2008 | Shelton, IV et al. |
| 7,431,730 B2 | 10/2008 | Viola |
| 7,434,717 B2 | 10/2008 | Shelton, IV et al. |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,455,682 B2 | 11/2008 | Viola |
| 7,464,846 B2 | 12/2008 | Shelton, IV et al. |
| 7,464,849 B2 | 12/2008 | Shelton, IV et al. |
| 7,467,740 B2 | 12/2008 | Shelton, IV et al. |
| 7,472,815 B2 | 1/2009 | Shelton, IV et al. |
| 7,473,221 B2 | 1/2009 | Ewers et al. |
| 7,490,749 B2 | 2/2009 | Schall et al. |
| 7,491,232 B2 | 2/2009 | Bolduc et al. |
| 7,500,979 B2 | 3/2009 | Hueil et al. |
| 7,506,791 B2 | 3/2009 | Omaits et al. |
| 7,510,107 B2 | 3/2009 | Timm et al. |
| 7,517,356 B2 | 4/2009 | Heinrich |
| 7,547,312 B2 | 6/2009 | Bauman et al. |
| 7,549,564 B2 | 6/2009 | Boudreaux |
| 7,568,603 B2 | 8/2009 | Shelton, IV et al. |
| 7,588,175 B2 | 9/2009 | Timm et al. |
| 7,588,176 B2 | 9/2009 | Timm et al. |
| 7,597,229 B2 | 10/2009 | Boudreaux et al. |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,644,848 B2 | 1/2010 | Swayze et al. |
| 7,658,311 B2 | 2/2010 | Boudreaux |
| 7,665,647 B2 | 2/2010 | Shelton, IV et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |

(56) References Cited

U.S. PATENT DOCUMENTS

| | | | |
|---|---|---|---|
| 7,673,781 B2 | 3/2010 | Swayze et al. | |
| 7,673,782 B2 | 3/2010 | Hess et al. | |
| 7,673,783 B2 | 3/2010 | Morgan et al. | |
| 7,686,201 B2 | 3/2010 | Csiky | |
| 7,699,844 B2 | 4/2010 | Utley et al. | |
| 7,699,859 B2 | 4/2010 | Bombard et al. | |
| 7,721,931 B2 | 5/2010 | Shelton, IV et al. | |
| 7,721,934 B2 | 5/2010 | Shelton, IV et al. | |
| 7,721,936 B2 | 5/2010 | Shalton, IV et al. | |
| 7,731,072 B2 | 6/2010 | Timm et al. | |
| 7,735,703 B2 | 6/2010 | Morgan et al. | |
| 7,736,306 B2 | 6/2010 | Brustad et al. | |
| 7,738,971 B2 | 6/2010 | Swayze et al. | |
| 7,740,159 B2 | 6/2010 | Shelton, IV et al. | |
| 7,753,245 B2 | 7/2010 | Boudreaux et al. | |
| 7,753,904 B2 | 7/2010 | Shelton, IV et al. | |
| 7,766,209 B2 | 8/2010 | Baxter, III et al. | |
| 7,766,210 B2 | 8/2010 | Shelton, IV et al. | |
| 7,770,775 B2 | 8/2010 | Shelton, IV et al. | |
| 7,776,060 B2 | 8/2010 | Mooradian et al. | |
| 7,780,685 B2 | 8/2010 | Hunt et al. | |
| 7,793,812 B2 | 9/2010 | Moore et al. | |
| 7,794,475 B2 | 9/2010 | Hess et al. | |
| 7,798,386 B2 | 9/2010 | Schall et al. | |
| 7,799,039 B2 | 9/2010 | Shelton, IV et al. | |
| 7,810,692 B2 | 10/2010 | Hall et al. | |
| 7,810,693 B2 | 10/2010 | Broehl et al. | |
| 7,819,296 B2 | 10/2010 | Hueil et al. | |
| 7,819,297 B2 | 10/2010 | Doll et al. | |
| 7,819,298 B2 | 10/2010 | Hall et al. | |
| 7,819,299 B2 | 10/2010 | Shelton, IV et al. | |
| 7,832,408 B2 | 11/2010 | Shelton, IV et al. | |
| 7,832,612 B2 | 11/2010 | Baxter, III et al. | |
| 7,837,080 B2 | 11/2010 | Schwemberger | |
| 7,845,537 B2 | 12/2010 | Shelton, IV et al. | |
| 7,857,185 B2 | 12/2010 | Swayze et al. | |
| 7,857,186 B2 | 12/2010 | Baxter, III et al. | |
| 7,861,906 B2 | 1/2011 | Doll et al. | |
| 7,866,527 B2 | 1/2011 | Hall et al. | |
| 7,871,418 B2 * | 1/2011 | Thompson et al. | 606/153 |
| 7,883,461 B2 | 2/2011 | Albrecht et al. | |
| 7,900,805 B2 | 3/2011 | Shelton, IV et al. | |
| 7,905,380 B2 | 3/2011 | Shelton, IV et al. | |
| 7,905,381 B2 | 3/2011 | Baxter, III et al. | |
| 7,913,891 B2 | 3/2011 | Doll et al. | |
| 7,914,543 B2 | 3/2011 | Roth et al. | |
| 7,918,377 B2 | 4/2011 | Measamer et al. | |
| 7,922,061 B2 | 4/2011 | Shelton, IV et al. | |
| 7,934,630 B2 | 5/2011 | Shelton, Iv et al. | |
| 7,942,890 B2 | 5/2011 | D'Agostino et al. | |
| 7,954,682 B2 | 6/2011 | Giordano et al. | |
| 7,954,684 B2 | 6/2011 | Boudreaux | |
| 7,954,686 B2 | 6/2011 | Baxter, III et al. | |
| 7,955,253 B2 | 6/2011 | Ewers et al. | |
| 7,955,257 B2 | 6/2011 | Frasier et al. | |
| 7,959,051 B2 | 6/2011 | Smith et al. | |
| 7,966,799 B2 | 6/2011 | Morgan et al. | |
| 7,980,443 B2 | 7/2011 | Scheib et al. | |
| 8,002,795 B2 | 8/2011 | Beetel | |
| 8,020,743 B2 | 9/2011 | Shelton, IV | |
| 8,034,077 B2 | 10/2011 | Smith et al. | |
| 8,056,787 B2 | 11/2011 | Boudreaux et al. | |
| 8,066,167 B2 | 11/2011 | Measamer et al. | |
| D650,074 S | 12/2011 | Hunt et al. | |
| 8,083,120 B2 | 12/2011 | Shelton, IV et al. | |
| 8,097,017 B2 | 1/2012 | Viola | |
| 8,113,410 B2 | 2/2012 | Hall et al. | |
| 8,123,767 B2 | 2/2012 | Bauman et al. | |
| 8,128,645 B2 | 3/2012 | Sonnenschein et al. | |
| 8,136,712 B2 | 3/2012 | Zingman | |
| 8,141,762 B2 | 3/2012 | Bedi et al. | |
| 8,157,145 B2 | 4/2012 | Shelton, IV et al. | |
| 8,157,153 B2 | 4/2012 | Shelton, IV et al. | |
| 8,161,977 B2 | 4/2012 | Shelton, IV et al. | |
| 8,167,185 B2 | 5/2012 | Shelton, IV et al. | |
| 8,172,124 B2 | 5/2012 | Shelton, IV et al. | |
| 8,186,555 B2 | 5/2012 | Shelton, IV et al. | |
| 8,186,560 B2 | 5/2012 | Hess et al. | |
| 8,196,795 B2 | 6/2012 | Moore et al. | |
| 8,196,796 B2 | 6/2012 | Shelton, IV et al. | |
| 8,205,781 B2 | 6/2012 | Baxter, III et al. | |
| 8,210,411 B2 | 7/2012 | Yates et al. | |
| 8,211,125 B2 | 7/2012 | Spivey | |
| 8,215,531 B2 | 7/2012 | Shelton, IV et al. | |
| 8,267,300 B2 | 9/2012 | Boudreaux | |
| 8,292,155 B2 | 10/2012 | Shelton, IV et al. | |
| 8,308,040 B2 | 11/2012 | Huang et al. | |
| 8,317,070 B2 | 11/2012 | Hueil et al. | |
| 8,322,455 B2 | 12/2012 | Shelton, IV et al. | |
| 8,322,589 B2 | 12/2012 | Boudreaux | |
| 8,333,313 B2 | 12/2012 | Boudreaux et al. | |
| 8,348,129 B2 | 1/2013 | Bedi et al. | |
| 8,348,131 B2 | 1/2013 | Omaits et al. | |
| 8,348,837 B2 * | 1/2013 | Wenchell | 600/201 |
| 8,353,437 B2 | 1/2013 | Boudreaux | |
| 8,353,438 B2 | 1/2013 | Baxter, III et al. | |
| 8,353,439 B2 | 1/2013 | Baxter, III et al. | |
| 8,360,296 B2 | 1/2013 | Zingman | |
| 8,360,297 B2 | 1/2013 | Shelton, IV et al. | |
| 8,365,976 B2 | 2/2013 | Hess et al. | |
| 8,371,491 B2 | 2/2013 | Huitema et al. | |
| 8,372,094 B2 | 2/2013 | Bettuchi et al. | |
| 8,393,514 B2 | 3/2013 | Shelton, IV et al. | |
| 8,397,971 B2 | 3/2013 | Yates et al. | |
| 8,408,439 B2 | 4/2013 | Huang et al. | |
| 2003/0220660 A1 | 11/2003 | Kortenbach et al. | |
| 2004/0006372 A1 | 1/2004 | Racenet et al. | |
| 2004/0097987 A1 | 5/2004 | Pugsley et al. | |
| 2004/0167572 A1 | 8/2004 | Roth et al. | |
| 2004/0193189 A1 | 9/2004 | Kortenbach et al. | |
| 2004/0254608 A1 | 12/2004 | Huitema et al. | |
| 2004/0260315 A1 | 12/2004 | Dell et al. | |
| 2004/0267310 A1 | 12/2004 | Racenet et al. | |
| 2005/0059997 A1 | 3/2005 | Bauman et al. | |
| 2005/0070929 A1 | 3/2005 | Dalessandro et al. | |
| 2005/0177181 A1 | 8/2005 | Kagan et al. | |
| 2005/0187576 A1 | 8/2005 | Whitman et al. | |
| 2005/0192628 A1 | 9/2005 | Viola | |
| 2005/0203550 A1 | 9/2005 | Laufer et al. | |
| 2005/0216055 A1 | 9/2005 | Scirica et al. | |
| 2005/0240222 A1 | 10/2005 | Shipp | |
| 2006/0047307 A1 | 3/2006 | Ortiz et al. | |
| 2006/0052825 A1 | 3/2006 | Ransick et al. | |
| 2006/0085033 A1 | 4/2006 | Criscuolo et al. | |
| 2006/0161185 A1 | 7/2006 | Saadat et al. | |
| 2006/0173470 A1 | 8/2006 | Oray et al. | |
| 2006/0201989 A1 | 9/2006 | Ojeda | |
| 2006/0235469 A1 | 10/2006 | Viola | |
| 2006/0241692 A1 | 10/2006 | McGuckin, Jr. et al. | |
| 2007/0073341 A1 | 3/2007 | Smith | |
| 2007/0102472 A1 | 5/2007 | Shelton, IV | |
| 2007/0106317 A1 | 5/2007 | Shelton, IV et al. | |
| 2007/0118175 A1 | 5/2007 | Butler et al. | |
| 2007/0170225 A1 | 7/2007 | Shelton, IV et al. | |
| 2007/0175949 A1 | 8/2007 | Shelton, IV et al. | |
| 2007/0175950 A1 | 8/2007 | Shelton, IV et al. | |
| 2007/0175951 A1 | 8/2007 | Shelton, IV et al. | |
| 2007/0175955 A1 | 8/2007 | Shelton, IV et al. | |
| 2007/0194079 A1 | 8/2007 | Hueil et al. | |
| 2007/0194082 A1 | 8/2007 | Morgan et al. | |
| 2007/0203510 A1 | 8/2007 | Bettuchi | |
| 2007/0225562 A1 | 9/2007 | Spivey et al. | |
| 2007/0239028 A1 | 10/2007 | Houser et al. | |
| 2007/0276189 A1 * | 11/2007 | Abel et al. | 600/210 |
| 2008/0029570 A1 | 2/2008 | Shelton et al. | |
| 2008/0029573 A1 | 2/2008 | Shelton et al. | |
| 2008/0029574 A1 | 2/2008 | Shelton et al. | |
| 2008/0029575 A1 | 2/2008 | Shelton et al. | |
| 2008/0078800 A1 | 4/2008 | Hess et al. | |
| 2008/0078802 A1 | 4/2008 | Hess et al. | |
| 2008/0078803 A1 | 4/2008 | Shelton et al. | |
| 2008/0078807 A1 | 4/2008 | Hess et al. | |
| 2008/0082114 A1 | 4/2008 | McKenna et al. | |
| 2008/0082125 A1 | 4/2008 | Murray et al. | |

(56) References Cited

U.S. PATENT DOCUMENTS

| | | |
|---|---|---|
| 2008/0140115 A1 | 6/2008 | Stopek |
| 2008/0167522 A1 | 7/2008 | Giordano et al. |
| 2008/0167672 A1 | 7/2008 | Giordano et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0172088 A1 | 7/2008 | Smith et al. |
| 2008/0296346 A1 | 12/2008 | Shelton, IV et al. |
| 2008/0308602 A1 | 12/2008 | Timm et al. |
| 2008/0308603 A1 | 12/2008 | Shelton, IV et al. |
| 2009/0001121 A1 | 1/2009 | Hess et al. |
| 2009/0001124 A1 | 1/2009 | Hess et al. |
| 2009/0001130 A1 | 1/2009 | Hess et al. |
| 2009/0005807 A1 | 1/2009 | Hess et al. |
| 2009/0005808 A1 | 1/2009 | Hess et al. |
| 2009/0005809 A1 | 1/2009 | Hess et al. |
| 2009/0012556 A1 | 1/2009 | Boudreaux et al. |
| 2009/0149871 A9 | 6/2009 | Kagan et al. |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206132 A1 | 8/2009 | Hueil et al. |
| 2009/0206133 A1 | 8/2009 | Morgan et al. |
| 2009/0206137 A1 | 8/2009 | Hall et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0209946 A1 | 8/2009 | Swayze et al. |
| 2009/0209979 A1 | 8/2009 | Yates et al. |
| 2009/0209990 A1 | 8/2009 | Yates et al. |
| 2009/0242610 A1 | 10/2009 | Shelton, IV et al. |
| 2009/0292176 A1 | 11/2009 | Bonadio et al. |
| 2010/0069942 A1 | 3/2010 | Shelton, IV |
| 2010/0076475 A1 | 3/2010 | Yates et al. |
| 2010/0089970 A1 | 4/2010 | Smith et al. |
| 2010/0127042 A1 | 5/2010 | Shelton, IV |
| 2010/0133317 A1 | 6/2010 | Shelton, IV et al. |
| 2010/0179382 A1 | 7/2010 | Shelton, IV et al. |
| 2010/0193566 A1 | 8/2010 | Scheib et al. |
| 2010/0193567 A1 | 8/2010 | Scheib et al. |
| 2010/0193568 A1 | 8/2010 | Scheib et al. |
| 2010/0198220 A1 | 8/2010 | Boudreaux et al. |
| 2010/0213241 A1 | 8/2010 | Bedi et al. |
| 2010/0222901 A1 | 9/2010 | Swayze et al. |
| 2010/0224669 A1 | 9/2010 | Shelton, IV et al. |
| 2010/0243709 A1 | 9/2010 | Hess et al. |
| 2010/0292540 A1 | 11/2010 | Hess et al. |
| 2010/0294829 A1 | 11/2010 | Giordano et al. |
| 2010/0301095 A1 | 12/2010 | Shelton, IV et al. |
| 2010/0305552 A1 | 12/2010 | Shelton, IV et al. |
| 2010/0312261 A1 | 12/2010 | Suzuki et al. |
| 2010/0331880 A1 | 12/2010 | Stopek |
| 2011/0006099 A1 | 1/2011 | Hall et al. |
| 2011/0006101 A1 | 1/2011 | Hall et al. |
| 2011/0006103 A1 | 1/2011 | Laurent et al. |
| 2011/0011914 A1 | 1/2011 | Baxter, III et al. |
| 2011/0011915 A1 | 1/2011 | Shelton, IV |
| 2011/0024477 A1 | 2/2011 | Hall et al. |
| 2011/0024478 A1 | 2/2011 | Shelton, IV |
| 2011/0024479 A1 | 2/2011 | Swensgard et al. |
| 2011/0042441 A1 | 2/2011 | Shelton, IV et al. |
| 2011/0060363 A1 | 3/2011 | Hess et al. |
| 2011/0068145 A1 | 3/2011 | Bedi et al. |
| 2011/0068148 A1 | 3/2011 | Hall et al. |
| 2011/0087276 A1 | 4/2011 | Bedi et al. |
| 2011/0087279 A1 | 4/2011 | Shah et al. |
| 2011/0114697 A1 | 5/2011 | Baxter, III et al. |
| 2011/0114700 A1 | 5/2011 | Baxter, III et al. |
| 2011/0118761 A1 | 5/2011 | Baxter, III et al. |
| 2011/0125176 A1 | 5/2011 | Yates et al. |
| 2011/0125177 A1 | 5/2011 | Yates et al. |
| 2011/0132963 A1 | 6/2011 | Giordano et al. |
| 2011/0132964 A1 | 6/2011 | Weisenburgh, II et al. |
| 2011/0132965 A1 | 6/2011 | Moore et al. |
| 2011/0144430 A1 | 6/2011 | Spivey et al. |
| 2011/0147433 A1 | 6/2011 | Shelton, IV et al. |
| 2011/0147434 A1 | 6/2011 | Hueil et al. |
| 2011/0155781 A1 | 6/2011 | Swensgard et al. |
| 2011/0155785 A1 | 6/2011 | Laurent et al. |
| 2011/0155787 A1 | 6/2011 | Baxter, III et al. |
| 2011/0163147 A1 | 7/2011 | Laurent et al. |
| 2011/0174861 A1 | 7/2011 | Shelton, IV et al. |
| 2011/0174863 A1 | 7/2011 | Shelton, IV et al. |
| 2011/0192882 A1 | 8/2011 | Hess et al. |
| 2011/0226837 A1 | 9/2011 | Baxter, III et al. |
| 2011/0275901 A1 | 11/2011 | Shelton, IV |
| 2011/0276083 A1 | 11/2011 | Shelton, IV et al. |
| 2011/0288573 A1 | 11/2011 | Yates et al. |
| 2011/0290851 A1 | 12/2011 | Shelton, IV |
| 2011/0290853 A1 | 12/2011 | Shelton, IV et al. |
| 2011/0290854 A1 | 12/2011 | Timm et al. |
| 2011/0290855 A1 | 12/2011 | Moore et al. |
| 2011/0290856 A1 | 12/2011 | Shelton, IV et al. |
| 2011/0295242 A1 | 12/2011 | Spivey et al. |
| 2011/0295269 A1 | 12/2011 | Swensgard et al. |
| 2011/0295270 A1 | 12/2011 | Giordano et al. |
| 2011/0295295 A1 | 12/2011 | Shelton, IV et al. |
| 2012/0024934 A1 | 2/2012 | Shelton, IV et al. |
| 2012/0024935 A1 | 2/2012 | Shelton, IV et al. |
| 2012/0024936 A1 | 2/2012 | Baxter, III et al. |
| 2012/0029272 A1 | 2/2012 | Shelton, IV et al. |
| 2012/0029544 A1 | 2/2012 | Shelton, IV et al. |
| 2012/0029547 A1 | 2/2012 | Shelton, IV et al. |
| 2012/0046692 A1 | 2/2012 | Smith et al. |
| 2012/0071711 A1 | 3/2012 | Shelton, IV et al. |
| 2012/0071866 A1 | 3/2012 | Kerr et al. |
| 2012/0074196 A1 | 3/2012 | Shelton, IV et al. |
| 2012/0074198 A1 | 3/2012 | Huitema et al. |
| 2012/0074200 A1 | 3/2012 | Schmid et al. |
| 2012/0074201 A1 | 3/2012 | Baxter, III et al. |
| 2012/0080332 A1 | 4/2012 | Shelton, IV et al. |
| 2012/0080333 A1 | 4/2012 | Woodard, Jr. et al. |
| 2012/0080335 A1 | 4/2012 | Shelton, IV et al. |
| 2012/0080336 A1 | 4/2012 | Shelton, IV et al. |
| 2012/0080337 A1 | 4/2012 | Shelton, IV et al. |
| 2012/0080338 A1 | 4/2012 | Shelton, IV et al. |
| 2012/0080339 A1 | 4/2012 | Shelton, IV et al. |
| 2012/0080340 A1 | 4/2012 | Shelton, IV et al. |
| 2012/0080344 A1 | 4/2012 | Shelton, IV |
| 2012/0080345 A1 | 4/2012 | Morgan et al. |
| 2012/0080477 A1 | 4/2012 | Leimbach et al. |
| 2012/0080478 A1 | 4/2012 | Morgan et al. |
| 2012/0080479 A1 | 4/2012 | Shelton, IV |
| 2012/0080480 A1 | 4/2012 | Woodard, Jr. et al. |
| 2012/0080481 A1 | 4/2012 | Widenhouse et al. |
| 2012/0080482 A1 | 4/2012 | Schall et al. |
| 2012/0080483 A1 | 4/2012 | Riestenberg et al. |
| 2012/0080484 A1 | 4/2012 | Morgan et al. |
| 2012/0080485 A1 | 4/2012 | Woodard, Jr. et al. |
| 2012/0080486 A1 | 4/2012 | Woodard, Jr. et al. |
| 2012/0080487 A1 | 4/2012 | Woodard, Jr. et al. |
| 2012/0080488 A1 | 4/2012 | Shelton, IV et al. |
| 2012/0080489 A1 | 4/2012 | Shelton, IV et al. |
| 2012/0080490 A1 | 4/2012 | Shelton, IV et al. |
| 2012/0080491 A1 | 4/2012 | Shelton, IV et al. |
| 2012/0080493 A1 | 4/2012 | Shelton, IV et al. |
| 2012/0080496 A1 | 4/2012 | Schall et al. |
| 2012/0080498 A1 | 4/2012 | Shelton, IV et al. |
| 2012/0080499 A1 | 4/2012 | Schall et al. |
| 2012/0080500 A1 | 4/2012 | Morgan et al. |
| 2012/0080501 A1 | 4/2012 | Morgan et al. |
| 2012/0080502 A1 | 4/2012 | Morgan et al. |
| 2012/0080503 A1 | 4/2012 | Woodard, Jr. et al. |
| 2012/0083833 A1 | 4/2012 | Shelton, IV et al. |
| 2012/0083834 A1 | 4/2012 | Shelton, IV et al. |
| 2012/0083835 A1 | 4/2012 | Shelton, IV et al. |
| 2012/0083836 A1 | 4/2012 | Shelton, IV et al. |
| 2012/0132450 A1 | 5/2012 | Timm et al. |
| 2012/0138660 A1 | 6/2012 | Shelton, IV |
| 2012/0160721 A1 | 6/2012 | Shelton, IV et al. |
| 2012/0175399 A1 | 7/2012 | Shelton et al. |

(56) References Cited

U.S. PATENT DOCUMENTS

| | | |
|---|---|---|
| 2012/0199630 A1 | 8/2012 | Shelton, IV et al. |
| 2012/0199631 A1 | 8/2012 | Shelton, IV et al. |
| 2012/0199632 A1 | 8/2012 | Spivey et al. |
| 2012/0199633 A1 | 8/2012 | Shelton, IV et al. |
| 2012/0203247 A1 | 8/2012 | Shelton, IV et al. |
| 2012/0205421 A1 | 8/2012 | Shelton, IV |
| 2012/0211546 A1 | 8/2012 | Shelton, IV |
| 2012/0234890 A1 | 9/2012 | Aronhalt et al. |
| 2012/0234891 A1 | 9/2012 | Aronhalt et al. |
| 2012/0234892 A1 | 9/2012 | Aronhalt et al. |
| 2012/0234893 A1 | 9/2012 | Schuckmann et al. |
| 2012/0234895 A1 | 9/2012 | O'Connor et al. |
| 2012/0234896 A1 | 9/2012 | Ellerhorst et al. |
| 2012/0234897 A1 | 9/2012 | Shelton, IV et al. |
| 2012/0234898 A1 | 9/2012 | Shelton, IV et al. |
| 2012/0234899 A1 | 9/2012 | Scheib et al. |
| 2012/0234900 A1 | 9/2012 | Swayze |
| 2012/0238823 A1 | 9/2012 | Hagerty et al. |
| 2012/0238824 A1 | 9/2012 | Widenhouse et al. |
| 2012/0238829 A1 | 9/2012 | Shelton, IV et al. |
| 2012/0239009 A1 | 9/2012 | Mollere et al. |
| 2012/0239010 A1 | 9/2012 | Shelton, IV et al. |
| 2012/0239012 A1 | 9/2012 | Laurent et al. |
| 2012/0239075 A1 | 9/2012 | Widenhouse et al. |
| 2012/0239082 A1 | 9/2012 | Shelton, IV et al. |
| 2012/0241491 A1 | 9/2012 | Aldridge et al. |
| 2012/0241492 A1 | 9/2012 | Shelton, IV et al. |
| 2012/0241493 A1 | 9/2012 | Baxter, III et al. |
| 2012/0241496 A1 | 9/2012 | Mandakolathur Vasudevan et al. |
| 2012/0241497 A1 | 9/2012 | Mandakolathur Vasudevan et al. |
| 2012/0241498 A1 | 9/2012 | Gonzalez et al. |
| 2012/0241499 A1 | 9/2012 | Baxter, III et al. |
| 2012/0241500 A1 | 9/2012 | Timmer et al. |
| 2012/0241501 A1 | 9/2012 | Swayze et al. |
| 2012/0241502 A1 | 9/2012 | Aldridge et al. |
| 2012/0241503 A1 | 9/2012 | Baxter, III et al. |
| 2012/0241505 A1 | 9/2012 | Alexander, III et al. |
| 2012/0248169 A1 | 10/2012 | Widenhouse et al. |
| 2012/0253298 A1 | 10/2012 | Henderson et al. |
| 2012/0265230 A1 | 10/2012 | Yates et al. |
| 2012/0273551 A1 | 11/2012 | Shelton, IV et al. |
| 2012/0283707 A1 | 11/2012 | Giordano et al. |
| 2012/0286019 A1 | 11/2012 | Hueil et al. |
| 2012/0292367 A1 | 11/2012 | Morgan et al. |
| 2012/0292370 A1 | 11/2012 | Hess et al. |
| 2012/0298719 A1 | 11/2012 | Shelton, IV et al. |
| 2013/0012931 A1 | 1/2013 | Spivey et al. |
| 2013/0012957 A1 | 1/2013 | Shelton, IV et al. |
| 2013/0020376 A1 | 1/2013 | Shelton, IV et al. |
| 2013/0023861 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0041371 A1 | 2/2013 | Yates et al. |

FOREIGN PATENT DOCUMENTS

| | | |
|---|---|---|
| CA | 2514274 A1 | 1/2006 |
| CN | 2488482 Y | 5/2002 |
| CN | 1634601 A | 7/2005 |
| CN | 1868411 A | 11/2006 |
| CN | 1915180 A | 2/2007 |
| CN | 101011286 A | 8/2007 |
| CN | 101095621 A | 1/2008 |
| DE | 273689 C | 5/1914 |
| DE | 1775926 A | 1/1972 |
| DE | 3036217 A1 | 4/1982 |
| DE | 3210466 A1 | 9/1983 |
| DE | 3709067 A1 | 9/1988 |
| DE | 9412228 U | 9/1994 |
| DE | 19509116 A1 | 9/1996 |
| DE | 19851291 A1 | 1/2000 |
| DE | 19924311 A1 | 11/2000 |
| DE | 69328576 T2 | 1/2001 |
| DE | 10052679 A1 | 5/2001 |
| DE | 20112837 U1 | 10/2001 |
| DE | 20121753 U1 | 4/2003 |
| DE | 10314072 A1 | 10/2004 |
| DE | 202007003114 U1 | 6/2007 |
| EP | 0122046 A1 | 10/1984 |
| EP | 0070230 B1 | 10/1985 |
| EP | 0156774 A2 | 10/1985 |
| EP | 0387980 B1 | 10/1985 |
| EP | 0033548 B1 | 5/1986 |
| EP | 0129442 B1 | 11/1987 |
| EP | 0276104 A2 | 7/1988 |
| EP | 0178940 B1 | 1/1991 |
| EP | 0178941 B1 | 1/1991 |
| EP | 0248844 B1 | 1/1993 |
| EP | 0545029 A1 | 6/1993 |
| EP | 0277959 B1 | 10/1993 |
| EP | 0233940 B1 | 11/1993 |
| EP | 0261230 B1 | 11/1993 |
| EP | 0639349 A2 | 2/1994 |
| EP | 0324636 B1 | 3/1994 |
| EP | 0593920 B1 | 4/1994 |
| EP | 0594148 A1 | 4/1994 |
| EP | 0427949 B1 | 6/1994 |
| EP | 0523174 B1 | 6/1994 |
| EP | 0600182 A2 | 6/1994 |
| EP | 0310431 B1 | 11/1994 |
| EP | 0375302 B1 | 11/1994 |
| EP | 0376562 B1 | 11/1994 |
| EP | 0630612 A1 | 12/1994 |
| EP | 0634144 A1 | 1/1995 |
| EP | 0646356 A2 | 4/1995 |
| EP | 0646357 A1 | 4/1995 |
| EP | 0653189 A2 | 5/1995 |
| EP | 0669104 A1 | 8/1995 |
| EP | 0511470 B1 | 10/1995 |
| EP | 0679367 A2 | 11/1995 |
| EP | 0392547 B1 | 12/1995 |
| EP | 0685204 A1 | 12/1995 |
| EP | 0364216 B1 | 1/1996 |
| EP | 0699418 A1 | 3/1996 |
| EP | 0702937 A1 | 3/1996 |
| EP | 0705571 A1 | 4/1996 |
| EP | 0711611 A2 | 5/1996 |
| EP | 0484677 B2 | 6/1996 |
| EP | 0541987 B1 | 7/1996 |
| EP | 0667119 B1 | 7/1996 |
| EP | 0708618 B1 | 3/1997 |
| EP | 0770355 A1 | 5/1997 |
| EP | 0503662 B1 | 6/1997 |
| EP | 0447121 B1 | 7/1997 |
| EP | 0625077 B1 | 7/1997 |
| EP | 0633749 B1 | 8/1997 |
| EP | 0710090 B1 | 8/1997 |
| EP | 0578425 B1 | 9/1997 |
| EP | 0625335 B1 | 11/1997 |
| EP | 0552423 B1 | 1/1998 |
| EP | 0592244 B1 | 1/1998 |
| EP | 0648476 B1 | 1/1998 |
| EP | 0649290 B1 | 3/1998 |
| EP | 0598618 B1 | 9/1998 |
| EP | 0676173 B1 | 9/1998 |
| EP | 0678007 B1 | 9/1998 |
| EP | 0603472 B1 | 11/1998 |
| EP | 0605351 B1 | 11/1998 |
| EP | 0878169 A1 | 11/1998 |
| EP | 0879742 A1 | 11/1998 |
| EP | 0695144 B1 | 12/1998 |
| EP | 0722296 B1 | 12/1998 |
| EP | 0760230 B1 | 2/1999 |
| EP | 0623316 B1 | 3/1999 |
| EP | 0650701 B1 | 3/1999 |
| EP | 0537572 B1 | 6/1999 |
| EP | 0923907 A1 | 6/1999 |
| EP | 0843906 B1 | 3/2000 |
| EP | 0552050 B1 | 5/2000 |
| EP | 0833592 B1 | 5/2000 |
| EP | 0830094 B1 | 9/2000 |
| EP | 1034747 A1 | 9/2000 |
| EP | 1034748 A1 | 9/2000 |

(56) References Cited

FOREIGN PATENT DOCUMENTS

| | | | |
|---|---|---|---|
| EP | 0694290 | B1 | 11/2000 |
| EP | 1050278 | A1 | 11/2000 |
| EP | 1053719 | A1 | 11/2000 |
| EP | 1053720 | A1 | 11/2000 |
| EP | 1055399 | A1 | 11/2000 |
| EP | 1055400 | A1 | 11/2000 |
| EP | 1080694 | A1 | 3/2001 |
| EP | 1090592 | A1 | 4/2001 |
| EP | 1095627 | A1 | 5/2001 |
| EP | 1256318 | B1 | 5/2001 |
| EP | 0806914 | B1 | 9/2001 |
| EP | 0768840 | B1 | 12/2001 |
| EP | 0908152 | B1 | 1/2002 |
| EP | 0872213 | B1 | 5/2002 |
| EP | 0862386 | B1 | 6/2002 |
| EP | 0949886 | B1 | 9/2002 |
| EP | 1238634 | A2 | 9/2002 |
| EP | 0858295 | B1 | 12/2002 |
| EP | 0656188 | B1 | 1/2003 |
| EP | 1284120 | A1 | 2/2003 |
| EP | 1287788 | A1 | 3/2003 |
| EP | 0717966 | B1 | 4/2003 |
| EP | 0869742 | B1 | 5/2003 |
| EP | 0829235 | B1 | 6/2003 |
| EP | 0887046 | B1 | 7/2003 |
| EP | 0852480 | B1 | 8/2003 |
| EP | 0891154 | B1 | 9/2003 |
| EP | 0813843 | B1 | 10/2003 |
| EP | 0873089 | B1 | 10/2003 |
| EP | 0856326 | B1 | 11/2003 |
| EP | 1374788 | A1 | 1/2004 |
| EP | 0741996 | B1 | 2/2004 |
| EP | 0814712 | B1 | 2/2004 |
| EP | 1402837 | A1 | 3/2004 |
| EP | 0705570 | B1 | 4/2004 |
| EP | 0959784 | B1 | 4/2004 |
| EP | 1407719 | A2 | 4/2004 |
| EP | 1086713 | B1 | 5/2004 |
| EP | 0996378 | B1 | 6/2004 |
| EP | 1426012 | A1 | 6/2004 |
| EP | 0833593 | B2 | 7/2004 |
| EP | 1442694 | A1 | 8/2004 |
| EP | 0888749 | B1 | 9/2004 |
| EP | 0959786 | B1 | 9/2004 |
| EP | 1459695 | A1 | 9/2004 |
| EP | 1473819 | A1 | 11/2004 |
| EP | 1477119 | A1 | 11/2004 |
| EP | 1479345 | A1 | 11/2004 |
| EP | 1479347 | A1 | 11/2004 |
| EP | 1479348 | A1 | 11/2004 |
| EP | 0754437 | B2 | 12/2004 |
| EP | 1025807 | B1 | 12/2004 |
| EP | 1001710 | B1 | 1/2005 |
| EP | 1520521 | A1 | 4/2005 |
| EP | 1520523 | A1 | 4/2005 |
| EP | 1520525 | A1 | 4/2005 |
| EP | 1522264 | A1 | 4/2005 |
| EP | 1523942 | A2 | 4/2005 |
| EP | 1550408 | A1 | 7/2005 |
| EP | 1557129 | A1 | 7/2005 |
| EP | 1064883 | B1 | 8/2005 |
| EP | 1067876 | B1 | 8/2005 |
| EP | 0870473 | B1 | 9/2005 |
| EP | 1157666 | B1 | 9/2005 |
| EP | 0880338 | B1 | 10/2005 |
| EP | 1158917 | B1 | 11/2005 |
| EP | 1344498 | B1 | 11/2005 |
| EP | 1330989 | B1 | 12/2005 |
| EP | 0771176 | B2 | 1/2006 |
| EP | 1621138 | A2 | 2/2006 |
| EP | 1621139 | A2 | 2/2006 |
| EP | 1621141 | A2 | 2/2006 |
| EP | 1621145 | A2 | 2/2006 |
| EP | 1621151 | A2 | 2/2006 |
| EP | 1034746 | B1 | 3/2006 |
| EP | 1632191 | A2 | 3/2006 |
| EP | 1065981 | B1 | 5/2006 |
| EP | 1082944 | B1 | 5/2006 |
| EP | 1652481 | A2 | 5/2006 |
| EP | 1382303 | B1 | 6/2006 |
| EP | 1253866 | BI | 7/2006 |
| EP | 1032318 | B1 | 8/2006 |
| EP | 1045672 | B1 | 8/2006 |
| EP | 1617768 | B1 | 8/2006 |
| EP | 1693015 | A2 | 8/2006 |
| EP | 1400214 | B1 | 9/2006 |
| EP | 1702567 | A2 | 9/2006 |
| EP | 1129665 | B1 | 11/2006 |
| EP | 1400206 | B1 | 11/2006 |
| EP | 1721568 | A1 | 11/2006 |
| EP | 1256317 | B1 | 12/2006 |
| EP | 1285633 | B1 | 12/2006 |
| EP | 1728473 | A1 | 12/2006 |
| EP | 1728475 | A2 | 12/2006 |
| EP | 1479346 | B1 | 1/2007 |
| EP | 1484024 | B1 | 1/2007 |
| EP | 1754445 | A2 | 2/2007 |
| EP | 1759812 | A1 | 3/2007 |
| EP | 1767163 | A1 | 3/2007 |
| EP | 1769756 | A1 | 4/2007 |
| EP | 1769758 | A1 | 4/2007 |
| EP | 1581128 | B1 | 5/2007 |
| EP | 1780825 | A1 | 5/2007 |
| EP | 1785097 | A2 | 5/2007 |
| EP | 1790293 | A2 | 5/2007 |
| EP | 1800610 | A1 | 6/2007 |
| EP | 1300117 | B1 | 8/2007 |
| EP | 1813199 | A1 | 8/2007 |
| EP | 1813201 | A1 | 8/2007 |
| EP | 1813202 | A1 | 8/2007 |
| EP | 1813203 | A2 | 8/2007 |
| EP | 1813207 | A1 | 8/2007 |
| EP | 1813209 | A1 | 8/2007 |
| EP | 1487359 | B1 | 10/2007 |
| EP | 1599146 | B1 | 10/2007 |
| EP | 1839596 | A1 | 10/2007 |
| EP | 2110083 | A2 | 10/2007 |
| EP | 1857057 | A2 | 11/2007 |
| EP | 1402821 | B1 | 12/2007 |
| EP | 1872727 | A1 | 1/2008 |
| EP | 1897502 | A1 | 3/2008 |
| EP | 1330201 | B1 | 6/2008 |
| EP | 1702568 | B1 | 7/2008 |
| EP | 1943955 | A2 | 7/2008 |
| EP | 1943957 | A2 | 7/2008 |
| EP | 1943964 | A1 | 7/2008 |
| EP | 1943976 | A2 | 7/2008 |
| EP | 1593337 | B1 | 8/2008 |
| EP | 1970014 | A1 | 9/2008 |
| EP | 1980213 | A2 | 10/2008 |
| EP | 1759645 | B1 | 11/2008 |
| EP | 1990014 | A2 | 11/2008 |
| EP | 1693008 | B1 | 12/2008 |
| EP | 1759640 | B1 | 12/2008 |
| EP | 2000102 | A2 | 12/2008 |
| EP | 2005894 | A2 | 12/2008 |
| EP | 2008595 | A2 | 12/2008 |
| EP | 1736104 | B1 | 3/2009 |
| EP | 1749486 | B1 | 3/2009 |
| EP | 2039316 | A2 | 3/2009 |
| EP | 1721576 | B1 | 4/2009 |
| EP | 1733686 | B1 | 4/2009 |
| EP | 2044890 | A1 | 4/2009 |
| EP | 1550409 | A1 | 6/2009 |
| EP | 1550413 | B1 | 6/2009 |
| EP | 1745748 | B1 | 8/2009 |
| EP | 2090237 | A1 | 8/2009 |
| EP | 2090244 | A2 | 8/2009 |
| EP | 2090245 | A1 | 8/2009 |
| EP | 2090256 | A2 | 8/2009 |
| EP | 2095777 | A2 | 9/2009 |
| EP | 2110082 | A1 | 10/2009 |
| EP | 1813208 | B1 | 11/2009 |
| EP | 1908426 | B1 | 11/2009 |

(56) References Cited

FOREIGN PATENT DOCUMENTS

| | | |
|---|---|---|
| EP | 2116195 A1 | 11/2009 |
| EP | 1607050 B1 | 12/2009 |
| EP | 1815804 B1 | 12/2009 |
| EP | 1566150 B1 | 4/2010 |
| EP | 1813206 B1 | 4/2010 |
| EP | 1769754 B1 | 6/2010 |
| EP | 1535565 B1 | 10/2010 |
| EP | 1702570 B1 | 10/2010 |
| EP | 1785098 B1 | 10/2010 |
| EP | 2005896 B1 | 10/2010 |
| EP | 2030578 B1 | 11/2010 |
| EP | 1627605 B1 | 12/2010 |
| EP | 1690502 B1 | 3/2011 |
| EP | 1813205 B1 | 6/2011 |
| EP | 2090243 B1 | 6/2011 |
| EP | 2153781 B1 | 11/2011 |
| EP | 1785102 B1 | 1/2012 |
| EP | 2005895 B1 | 8/2012 |
| FR | 999646 A | 2/1952 |
| FR | 1112936 A | 3/1956 |
| FR | 2598905 A1 | 11/1987 |
| FR | 2765794 A | 1/1999 |
| GB | 939929 A | 10/1963 |
| GB | 1210522 A | 10/1970 |
| GB | 1217159 A | 12/1970 |
| GB | 1339394 A | 12/1973 |
| GB | 2109241 A | 6/1983 |
| GB | 2272159 A | 5/1994 |
| GB | 2284242 A | 5/1995 |
| GB | 2336214 A | 10/1999 |
| GB | 2425903 A | 11/2006 |
| JP | 50-33988 U | 4/1975 |
| JP | 58500053 A | 1/1983 |
| JP | 61-98249 A | 5/1986 |
| JP | 61502036 A | 9/1986 |
| JP | 63-203149 | 8/1988 |
| JP | 3-12126 A | 1/1991 |
| JP | 5-212039 A | 8/1993 |
| JP | 6007357 A | 1/1994 |
| JP | 7051273 A | 2/1995 |
| JP | 7-124166 A | 5/1995 |
| JP | 7-255735 A | 10/1995 |
| JP | 8-33642 A | 2/1996 |
| JP | 8033641 A | 2/1996 |
| JP | 8-164141 A | 6/1996 |
| JP | 8229050 A | 9/1996 |
| JP | 2000033071 A | 2/2000 |
| JP | 2000171730 A | 6/2000 |
| JP | 2000287987 A | 10/2000 |
| JP | 2000325303 A | 11/2000 |
| JP | 2001-514541 A | 9/2001 |
| JP | 2001286477 A | 10/2001 |
| JP | 2002143078 A | 5/2002 |
| JP | 2002369820 A | 12/2002 |
| JP | 2003-500153 A | 1/2003 |
| JP | 2003-521301 A | 7/2003 |
| JP | 2004-329624 A | 11/2004 |
| JP | 2004-344663 | 12/2004 |
| JP | 2005-028149 | 2/2005 |
| JP | 2005505322 T | 2/2005 |
| JP | 2005103293 A | 4/2005 |
| JP | 2005131163 A | 5/2005 |
| JP | 2005131164 A | 5/2005 |
| JP | 2005131173 A | 5/2005 |
| JP | 2005131211 A | 5/2005 |
| JP | 2005131212 A | 5/2005 |
| JP | 2005137423 A | 6/2005 |
| JP | 2005152416 A | 6/2005 |
| JP | 2005-523105 A | 8/2005 |
| JP | 2005524474 A | 8/2005 |
| JP | 2006-034975 A | 2/2006 |
| JP | 2006-218297 A | 8/2006 |
| JP | 2006-281405 A | 10/2006 |
| JP | 2007-117725 A | 5/2007 |
| JP | 2008-283459 A | 11/2008 |
| RU | 2008830 C1 | 3/1994 |
| RU | 2141279 C1 | 11/1999 |
| RU | 2187249 C2 | 8/2002 |
| RU | 2225170 C2 | 3/2004 |
| SU | 189517 A | 1/1967 |
| SU | 328636 A | 9/1972 |
| SU | 886900 A | 12/1981 |
| SU | 1009439 A | 4/1983 |
| SU | 1333319 A2 | 8/1987 |
| SU | 1377053 A1 | 2/1988 |
| SU | 1561964 A1 | 5/1990 |
| SU | 1708312 A1 | 1/1992 |
| SU | 1722476 A1 | 3/1992 |
| SU | 1752361 A1 | 8/1992 |
| WO | WO 82/02824 A1 | 9/1982 |
| WO | WO 91/15157 A1 | 10/1991 |
| WO | WO 92/20295 A1 | 11/1992 |
| WO | WO 92/21300 A1 | 12/1992 |
| WO | WO 93/08755 A1 | 5/1993 |
| WO | WO 93/13718 A1 | 7/1993 |
| WO | WO 93/14690 A1 | 8/1993 |
| WO | WO 93/15648 A1 | 8/1993 |
| WO | WO 93/15850 A1 | 8/1993 |
| WO | WO 93/19681 A1 | 10/1993 |
| WO | WO 94/00060 A1 | 1/1994 |
| WO | WO 94/11057 A1 | 5/1994 |
| WO | WO 94/12108 A1 | 6/1994 |
| WO | WO 94/18893 A1 | 9/1994 |
| WO | WO 94/22378 A1 | 10/1994 |
| WO | WO 94/23659 A1 | 10/1994 |
| WO | WO 95/02369 A1 | 1/1995 |
| WO | WO 95/03743 A1 | 2/1995 |
| WO | WO 95/06817 A1 | 3/1995 |
| WO | WO 95/09576 A1 | 4/1995 |
| WO | WO 95/09577 A1 | 4/1995 |
| WO | WO 95/14436 A1 | 6/1995 |
| WO | WO 95/17855 A1 | 7/1995 |
| WO | WO 95/18383 A1 | 7/1995 |
| WO | WO 95/18572 A1 | 7/1995 |
| WO | WO 95/19739 A1 | 7/1995 |
| WO | WO 95/20360 A1 | 8/1995 |
| WO | WO 95/23557 A1 | 9/1995 |
| WO | WO 95/24865 A1 | 9/1995 |
| WO | WO 95/25471 A3 | 9/1995 |
| WO | WO 95/26562 A1 | 10/1995 |
| WO | WO 95/29639 A1 | 11/1995 |
| WO | WO 96/04858 A1 | 2/1996 |
| WO | WO 96/19151 A1 | 6/1996 |
| WO | WO 96/19152 A1 | 6/1996 |
| WO | WO 96/20652 A1 | 7/1996 |
| WO | WO 96/21119 A1 | 7/1996 |
| WO | WO 96/22055 A1 | 7/1996 |
| WO | WO 96/23448 A1 | 8/1996 |
| WO | WO 96/24301 A1 | 8/1996 |
| WO | WO 96/27337 A1 | 9/1996 |
| WO | WO 96/31155 A1 | 10/1996 |
| WO | WO 96/35464 A1 | 11/1996 |
| WO | WO 96/39085 A1 | 12/1996 |
| WO | WO 96/39086 A1 | 12/1996 |
| WO | WO 96/39087 A1 | 12/1996 |
| WO | WO 96/39088 A1 | 12/1996 |
| WO | WO 96/39089 A1 | 12/1996 |
| WO | WO 97/00646 A1 | 1/1997 |
| WO | WO 97/00647 A1 | 1/1997 |
| WO | WO 97/06582 A1 | 2/1997 |
| WO | WO 97/10763 A1 | 3/1997 |
| WO | WO 97/10764 A1 | 3/1997 |
| WO | WO 97/11648 A2 | 4/1997 |
| WO | WO 97/11649 A1 | 4/1997 |
| WO | WO 97/15237 A1 | 5/1997 |
| WO | WO 97/24073 A1 | 7/1997 |
| WO | WO 97/24993 A1 | 7/1997 |
| WO | WO 97/30644 A1 | 8/1997 |
| WO | WO 97/34533 A1 | 9/1997 |
| WO | WO 97/37598 A1 | 10/1997 |
| WO | WO 97/39688 A2 | 10/1997 |
| WO | WO 98/17180 A1 | 4/1998 |
| WO | WO 98/27880 A1 | 7/1998 |
| WO | WO 98/30153 A1 | 7/1998 |

(56) References Cited

FOREIGN PATENT DOCUMENTS

| | | |
|---|---|---|
| WO | WO 98/47436 A1 | 10/1998 |
| WO | WO 99/03407 A1 | 1/1999 |
| WO | WO 99/03408 A1 | 1/1999 |
| WO | WO 99/03409 A1 | 1/1999 |
| WO | WO 99/12483 A1 | 3/1999 |
| WO | WO 99/12487 A1 | 3/1999 |
| WO | WO 99/12488 A1 | 3/1999 |
| WO | WO 99/15086 A1 | 4/1999 |
| WO | WO 99/15091 A1 | 4/1999 |
| WO | WO 99/23933 A2 | 5/1999 |
| WO | WO 99/23959 A1 | 5/1999 |
| WO | WO 99/25261 A1 | 5/1999 |
| WO | WO 99/29244 A1 | 6/1999 |
| WO | WO 99/34744 A1 | 7/1999 |
| WO | WO 99/45849 A1 | 9/1999 |
| WO | WO 99/48430 A1 | 9/1999 |
| WO | WO 99/51158 A1 | 10/1999 |
| WO | WO 00/24322 A1 | 5/2000 |
| WO | WO 00/24330 A1 | 5/2000 |
| WO | WO 00/41638 A1 | 7/2000 |
| WO | WO 00/48506 A1 | 8/2000 |
| WO | WO 00/53112 A2 | 9/2000 |
| WO | WO 00/54653 A1 | 9/2000 |
| WO | WO 00/57796 A1 | 10/2000 |
| WO | WO 00/64365 A1 | 11/2000 |
| WO | WO 00/72762 A1 | 12/2000 |
| WO | WO 00/72765 A1 | 12/2000 |
| WO | WO 01/03587 A1 | 1/2001 |
| WO | WO 01/05702 A1 | 1/2001 |
| WO | WO 01/10482 A1 | 2/2001 |
| WO | WO 01/35845 A1 | 5/2001 |
| WO | WO 01/54594 A1 | 8/2001 |
| WO | WO 01/58371 A1 | 8/2001 |
| WO | WO 01/62158 A2 | 8/2001 |
| WO | WO 01/62161 A1 | 8/2001 |
| WO | WO 01/62162 A1 | 8/2001 |
| WO | WO 01/62164 A2 | 8/2001 |
| WO | WO 01/62169 A2 | 8/2001 |
| WO | WO 01/78605 A2 | 10/2001 |
| WO | WO 01/91646 A1 | 12/2001 |
| WO | WO 02/07608 A2 | 1/2002 |
| WO | WO 02/07618 A1 | 1/2002 |
| WO | WO 02/17799 A1 | 3/2002 |
| WO | WO 02/19920 A1 | 3/2002 |
| WO | WO 02/19932 A1 | 3/2002 |
| WO | WO 02/30297 A2 | 4/2002 |
| WO | WO 02/32322 A2 | 4/2002 |
| WO | WO 02/36028 A1 | 5/2002 |
| WO | WO 02/43571 A2 | 6/2002 |
| WO | WO 02/058568 A1 | 8/2002 |
| WO | WO 02/060328 A1 | 8/2002 |
| WO | WO 02/067785 A2 | 9/2002 |
| WO | WO 02/098302 A1 | 12/2002 |
| WO | WO 03/000138 A2 | 1/2003 |
| WO | WO 03/001329 A2 | 1/2003 |
| WO | WO 03/013363 A1 | 2/2003 |
| WO | WO 03/015604 A2 | 2/2003 |
| WO | WO 03/020106 A2 | 3/2003 |
| WO | WO 03/020139 A2 | 3/2003 |
| WO | WO 03/024339 A1 | 3/2003 |
| WO | WO 03/079909 A3 | 3/2003 |
| WO | WO 03/030743 A2 | 4/2003 |
| WO | WO 03/037193 A1 | 5/2003 |
| WO | WO 03/047436 A3 | 6/2003 |
| WO | WO 03/055402 A1 | 7/2003 |
| WO | WO 03/057048 A1 | 7/2003 |
| WO | WO 03/057058 A1 | 7/2003 |
| WO | WO 03/063694 A1 | 8/2003 |
| WO | WO 03/077769 A1 | 9/2003 |
| WO | WO 03/079911 A1 | 10/2003 |
| WO | WO 03/082126 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 03/094746 A1 | 11/2003 |
| WO | WO 03/094747 A1 | 11/2003 |
| WO | WO 03/101313 A1 | 12/2003 |
| WO | WO 03/105698 A2 | 12/2003 |
| WO | WO 03/105702 A2 | 12/2003 |
| WO | WO 2004/006980 A2 | 1/2004 |
| WO | WO 2004/011037 A2 | 2/2004 |
| WO | WO 2004/019769 A1 | 3/2004 |
| WO | WO 2004/021868 A2 | 3/2004 |
| WO | WO 2004/028585 A2 | 4/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/034875 A2 | 4/2004 |
| WO | WO 2004/047626 A1 | 6/2004 |
| WO | WO 2004/047653 A2 | 6/2004 |
| WO | WO 2004/049956 A2 | 6/2004 |
| WO | WO 2004/052426 A2 | 6/2004 |
| WO | WO 2004/056276 A1 | 7/2004 |
| WO | WO 2004/056277 A1 | 7/2004 |
| WO | WO 2004/062516 A1 | 7/2004 |
| WO | WO 2004/078050 A2 | 9/2004 |
| WO | WO 2004/078051 A2 | 9/2004 |
| WO | WO 2004/086987 A1 | 10/2004 |
| WO | WO 2004/096015 A2 | 11/2004 |
| WO | WO 2004/096057 A2 | 11/2004 |
| WO | WO 2004/103157 A2 | 12/2004 |
| WO | WO 2004/105593 A1 | 12/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/044078 A2 | 5/2005 |
| WO | WO 2005/055846 A1 | 6/2005 |
| WO | WO 2005/072634 A2 | 8/2005 |
| WO | WO 2005/078892 A1 | 8/2005 |
| WO | WO 2005/079675 A2 | 9/2005 |
| WO | WO 2005/096954 A2 | 10/2005 |
| WO | WO 2005/112806 A2 | 12/2005 |
| WO | WO 2005/112808 A1 | 12/2005 |
| WO | WO 2005/115251 A2 | 12/2005 |
| WO | WO 2005/115253 A2 | 12/2005 |
| WO | WO 2005/117735 A1 | 12/2005 |
| WO | WO 2005/122936 A1 | 12/2005 |
| WO | WO 2006/023486 A1 | 3/2006 |
| WO | WO 2006/027014 A1 | 3/2006 |
| WO | WO 2006/044490 A2 | 4/2006 |
| WO | WO 2006/044581 A2 | 4/2006 |
| WO | WO 2006/044810 A2 | 4/2006 |
| WO | WO 2006/051252 A1 | 5/2006 |
| WO | WO 2006/059067 A1 | 6/2006 |
| WO | WO 2006/083748 A1 | 8/2006 |
| WO | WO 2006/092563 A1 | 9/2006 |
| WO | WO 2006/092565 A1 | 9/2006 |
| WO | WO 2006/115958 A1 | 11/2006 |
| WO | WO 2006/125940 A1 | 11/2006 |
| WO | WO 2006/132992 A1 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/098220 A2 | 8/2007 |
| WO | WO 2007/121579 A1 | 11/2007 |
| WO | WO 2007/131110 A2 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2007/147439 A1 | 12/2007 |
| WO | WO 2008/021969 A2 | 2/2008 |
| WO | WO 2008/039249 A1 | 4/2008 |
| WO | WO 2008/039270 A1 | 4/2008 |
| WO | WO 2008/045383 A2 | 4/2008 |
| WO | WO 2008/070763 A1 | 6/2008 |
| WO | WO 2008/089404 A2 | 7/2008 |
| WO | WO 2008/109125 A1 | 9/2008 |
| WO | WO 2008/124748 A1 | 10/2008 |
| WO | WO 2009/023861 A1 | 2/2009 |
| WO | WO 2010/054404 A1 | 5/2010 |

(56) References Cited

FOREIGN PATENT DOCUMENTS

| WO | WO 2010/063795 A1 | 6/2010 |
|----|-------------------|--------|
| WO | WO 2010/098871 A2 | 9/2010 |
| WO | WO 2012/021671 A1 | 2/2012 |
| WO | WO 2012/044844 A2 | 4/2012 |

OTHER PUBLICATIONS

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000. 7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

The Sodem Aseptic Battery Transfer Kit, Sodem Systems, (2000), 3 pages.

"Biomedical Coatings," Fort Wayne Metals, Research Products Corporation, obtained online at www.fwmetals.com on Jun. 21, 2010 (1 page).

Van Meer et al., "A Disposable Plastic Compact Wrist for Smart Minimally Invasive Surgical Tools," LAAS/CNRS (Aug. 2005).

Breedveld et al., "A New, Easily Miniaturized Sterrable Endoscope," IEEE Engineering in Medicine and Biology Magazine (Nov./Dec. 2005).

D. Tuite, Ed., "Get the Lowdown on Ultracapacitors," Nov. 15, 2007; [online] URL: http://electronicdesign.com/Articles/Print.cfm?ArticleID=17465, accessed Jan. 15, 2008 (5 pages).

Datasheet for Panasonic TK Relays Ultra Low Profile 2 A Polarized Relay, Copyright Matsushita Electric Works, Ltd. (Known of at least as early as Aug. 17, 2010), 5 pages.

ASTM procedure D2240-00, "Standard Test Method for Rubber Property-Durometer Hardness," (Published Aug. 2000).

ASTM procedure D2240-05, "Standard Test Method for Rubber Property-Durometer Hardness," (Published Apr. 2010).

International Search Report for PCT/US2012/028886, dated Nov. 23, 2012 (6 pages).

\* cited by examiner

FIG. 3

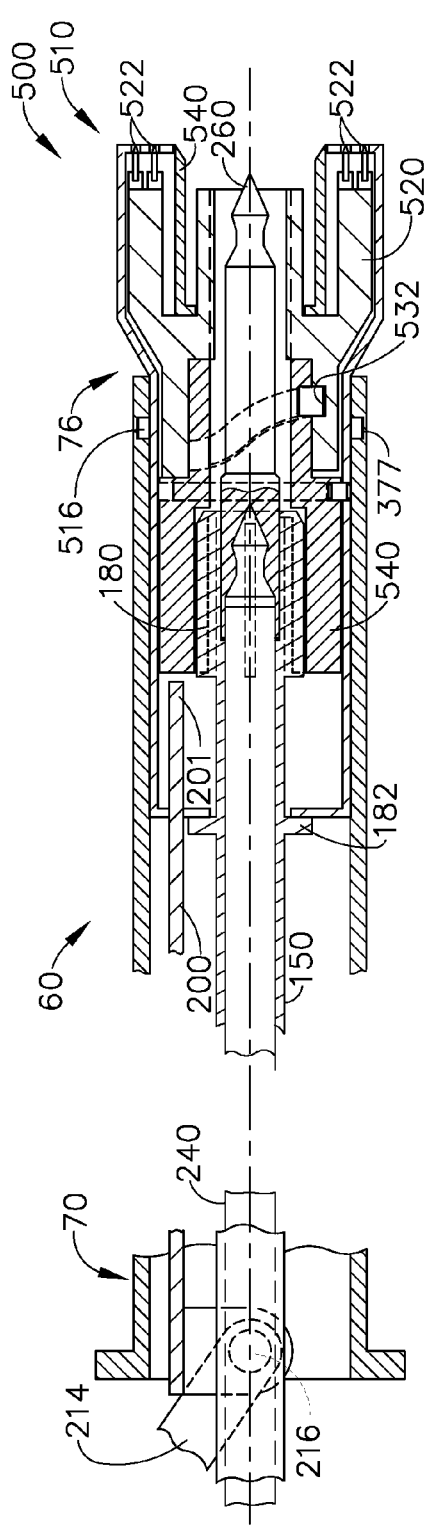
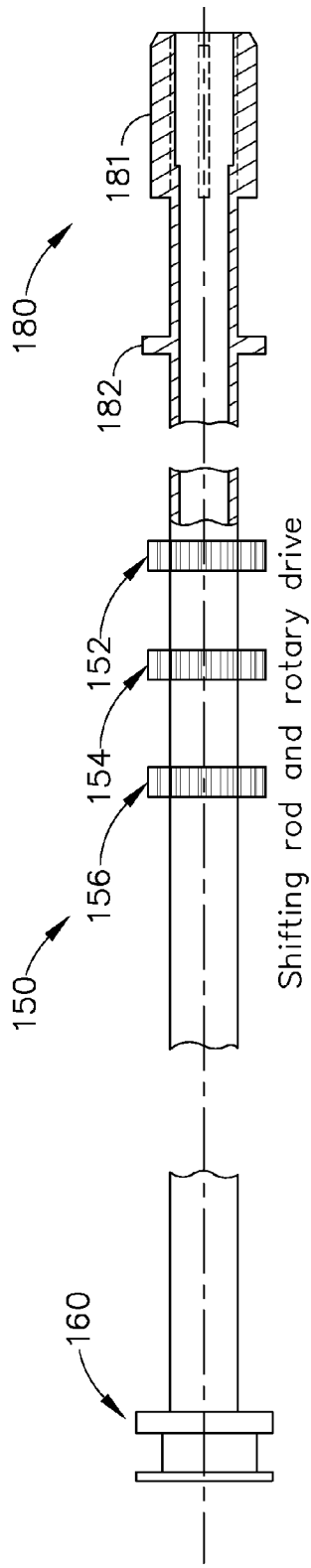
FIG. 9
FIG. 10

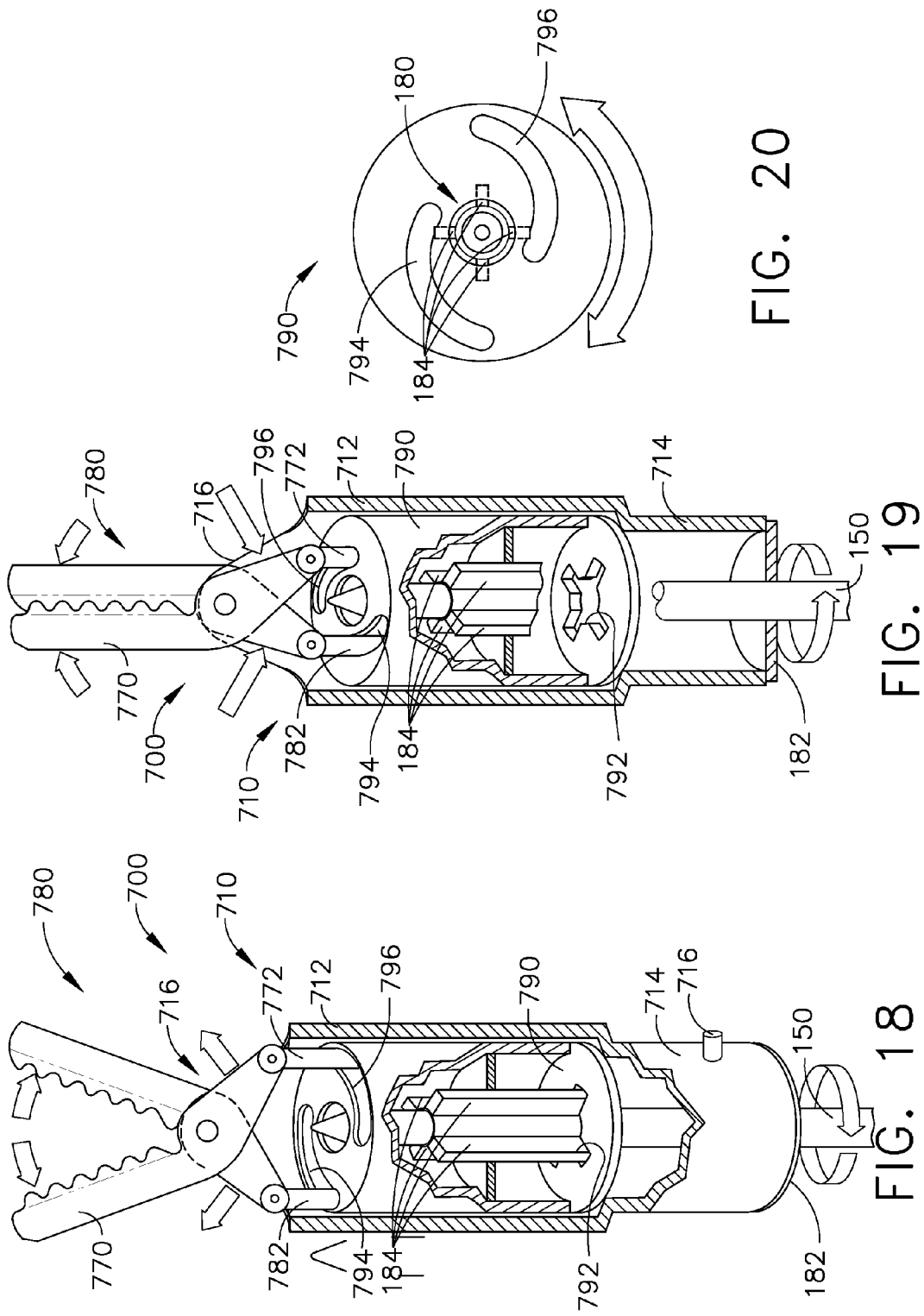

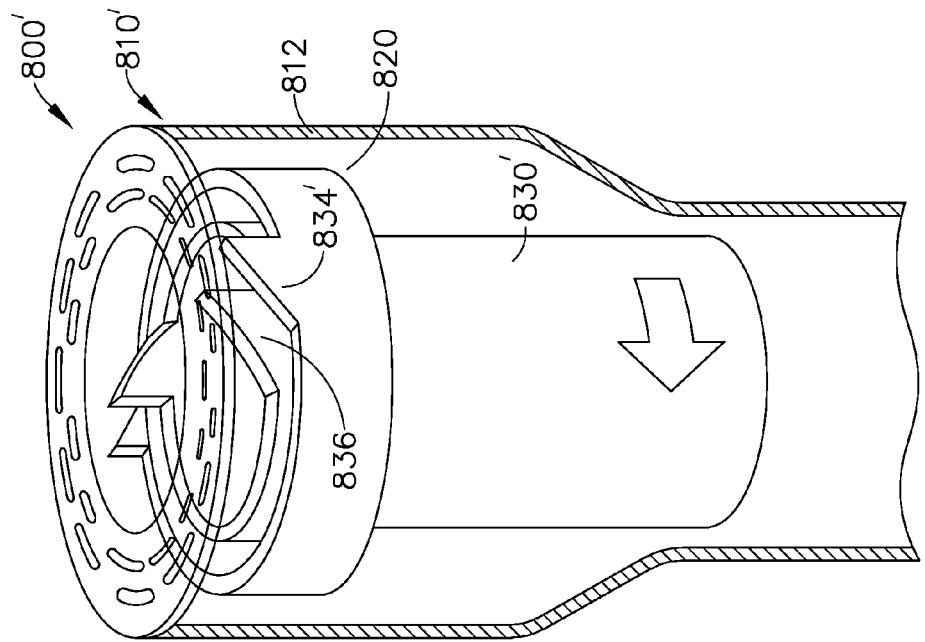
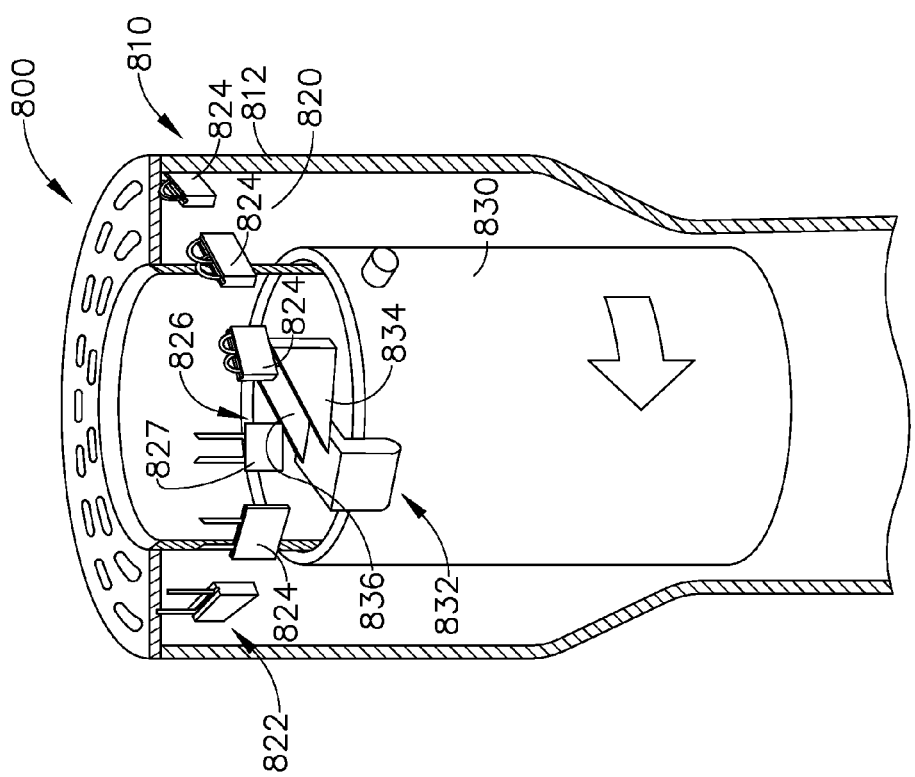

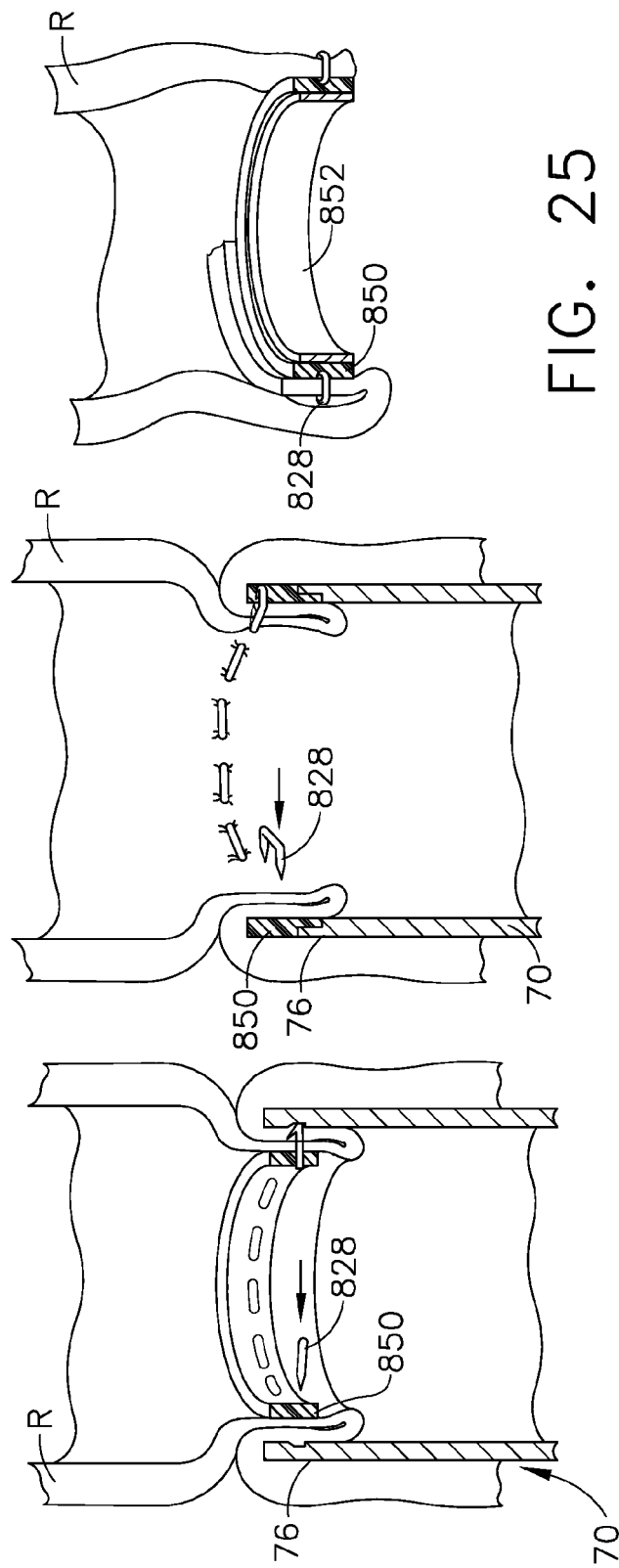

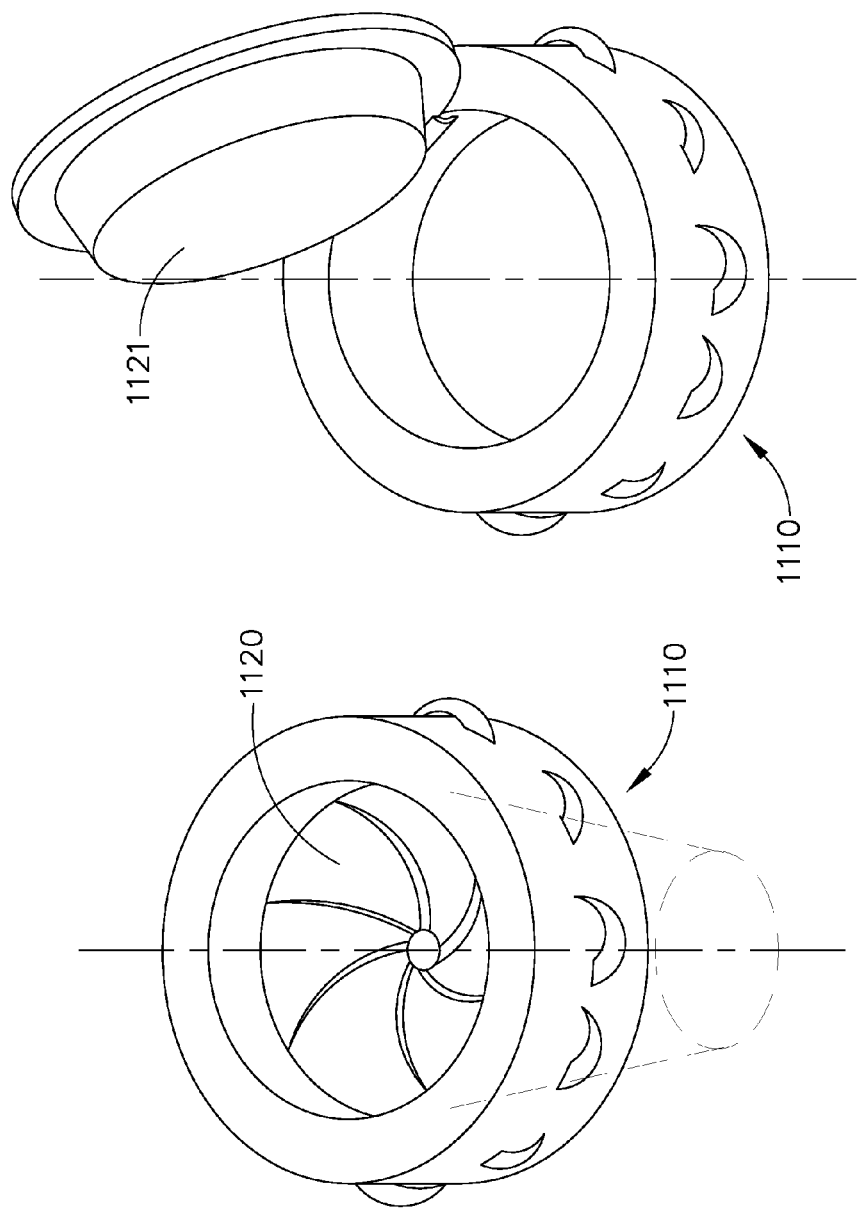

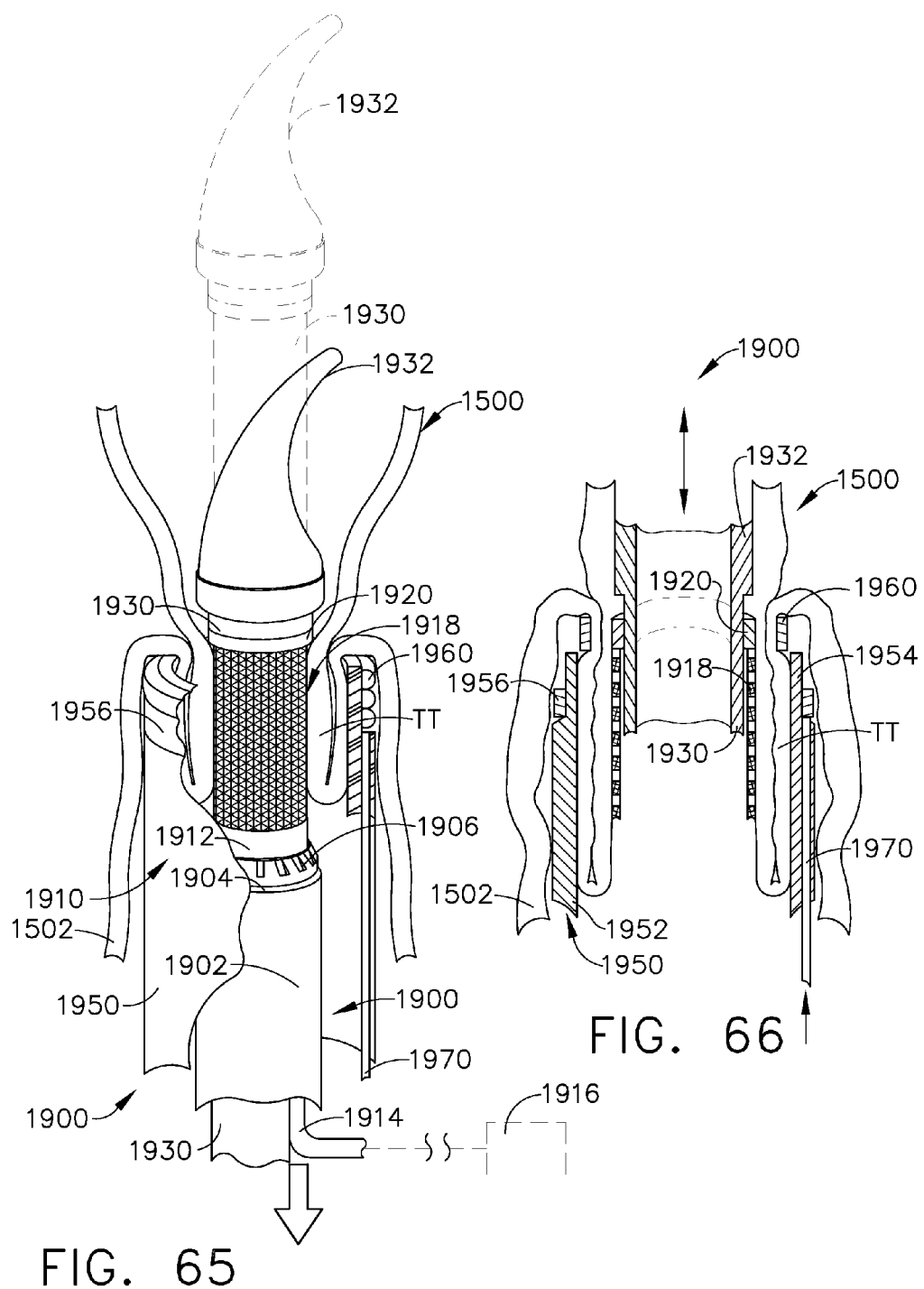

TRANS-RECTUM UNIVERSAL PORTS

CROSS-REFERENCE TO RELATED APPLICATIONS

This non-provisional patent application claims the benefit of and priority from U.S. Provisional Patent Application Ser. No. 61/452,432, filed Mar. 14, 2011, entitled "Surgical Stapling Instruments", the entire disclosure of which is hereby incorporated by reference.

FIELD OF THE INVENTION

The present invention generally relates to surgical devices for performing a variety of surgical procedures, and more particularly, to a surgical tool system that comprises a single handle assembly that can be employed with different tool attachments that are capable of performing different surgical procedures and actions.

BACKGROUND

Circular instruments are used to perform a number of surgical procedures. Such procedures often require the use of several different circular instruments that have a desired diametric size, shaft length and shaft geometry. Hospitals require storage space to inventory multiple product codes to satisfy these procedures.

One type of circular instrument that is often used in open and laparoscopic approaches is a circular stapling instrument. In general, a conventional circular stapler typically consists of an elongated shaft that has a proximal actuating mechanism and a distal stapling mechanism mounted to the elongated shaft. Various circular stapling devices are disclosed, for example, in U.S. Pat. Nos. 5,104,025; 5,205,459; 5,285,945; and 5,309,927 which are each herein incorporated by reference in their respective entireties. The distal stapling mechanism commonly consists of a fixed stapling cartridge that contains a plurality of staples configured in a concentric circular array. A round cutting knife is concentrically mounted in the cartridge interior for axial travel therein. Extending axially from the center of the cartridge is a movable trocar or attachment shaft that is adapted to have a staple anvil removably coupled thereto. The anvil is configured to form the ends of the staples as they are driven into it. The distance between a distal face of the staple cartridge and the staple anvil is commonly controlled by an adjustment mechanism that is mounted to the proximal end of the stapler shaft for controlling the axial movement of the trocar. Tissue that is clamped between the staple cartridge and the staple anvil is simultaneously stapled and cut when the actuating mechanism is activated by the surgeon.

Such circular stapling instruments are essential for creating anastomosis within the body when using open or laparoscopic methods. However, such instruments cannot perform other actions or procedures that may also be required to complete a particular operation. Such actions may comprise, for example, grasping and manipulating tissue, cutting tissue without deploying fasteners, dilating colon tissue, safely managing the removal of the transected specimens from the colon, etc. Thus, different types and sizes of instruments must be kept on hand.

Thus, the need exists for a surgical tool system that includes a single handle assembly that can be employed with different tool attachments that are capable of performing different surgical procedures and actions.

There is a further need for a universal port arrangement that can be used to dilate and/or occlude the colon and facilitate the entry and removal of surgical instruments within the colon;

There is a further need for a universal port arrangement that may be selectively employed to sever colon tissue.

Yet another need exists for a universal port arrangement that can facilitate the safe removal of transected colon portions.

The foregoing discussion is intended only to illustrate some of the shortcomings present in the field of the invention at the time, and should not be taken as a disavowal of claim scope.

BRIEF SUMMARY

In connection with general aspects of various embodiments of the present invention, there is provided a modular circular surgical instrument. In at least one form, the instrument comprises an actuator for generating an actuation motion and an actuation system that is configured to generate a plurality of discrete rotary drive motions in response to an application of the actuation motion thereto. An elongated shaft assembly operably interfaces with the actuation system and is configured to be interchangeably attached to a plurality of different surgical tool heads such that upon attachment of a first one of the surgical tool heads thereto, the elongated shaft assembly is caused to interact with the actuation system to impart a first one of the discrete rotary drive motions to the first surgical tool head when the actuation motion is applied to the actuation system. When a second one of the surgical tool heads is attached to the elongated shaft assembly, the elongated shaft assembly is caused to interact with the actuation system to impart a second one of the discrete rotary drive motions to the second surgical tool head upon when the actuation motion is applied to the actuation system.

In connection with yet another general aspect of one form of the present invention, there is provided a modular surgical instrument system that comprises a handle assembly that has a manually-actuatable actuator trigger operably supported thereon for generating an actuation motion. An actuation system is operably supported by the handle assembly and is configured to generate a plurality of discrete drive motions in response to an application of the actuation motion thereto. The instrument further comprises an elongated shaft assembly that includes an outer shaft casing that has a distal end. A rotary drive shaft is operably supported within the outer shaft casing and is oriented for selective operable interaction with the actuation system. The instrument further comprises a first surgical tool head that is configured for interchangeable attachment to the distal end of the outer shaft casing such that upon attachment thereto, the first surgical tool head moves the rotary drive shaft to a first drive position wherein upon application of the actuation motion to the actuation system, the rotary drive shaft imparts a first rotary drive motion to the first surgical tool head to cause the first surgical tool head to perform a first surgical action. A second surgical tool head is configured for interchangeable attachment to the distal end of the outer shaft casing such that upon attachment thereto, the second surgical tool head moves the rotary drive shaft to a second drive position wherein upon application of the actuation motion to the actuation system, the rotary drive shaft imparts a second rotary drive motion to the second surgical tool head to cause the second surgical tool head to perform a second surgical action that differs from the first surgical action. A third surgical tool head is configured for interchangeable attachment to the distal end of the outer shaft casing such that upon attachment thereto, the third surgical tool head moves the rotary drive shaft to a third drive position wherein upon said application of said actuation motion to said actuation system, the rotary drive shaft imparts a third rotary drive motion to the third surgical tool head to cause the third surgical tool head to perform a third surgical action.

In accordance with still another general aspect of one form of the present invention, there is provided a method for performing colorectal surgery. The method comprises providing a modular surgical instrument that has an elongated shaft assembly that includes a distal end and is configured to generate a plurality of discrete drive motions upon application of actuation motions thereto. The method further comprises coupling a first surgical tool head that is configured to perform a first surgical procedure to the distal end of the elongated shaft assembly and inserting the surgical instrument into the colon to bring the first surgical tool head into operable engagement with a target tissue. The method further includes applying a first actuation motion to the surgical instrument to cause the first surgical tool head to perform the first surgical action on the target tissue. The method also comprises withdrawing the surgical instrument from the colon and detaching the first surgical tool head from the surgical instrument. The method further includes coupling a second surgical tool head that is configured to perform a second surgical procedure that differs from the first surgical procedure to the distal end of the elongated shaft assembly and reinserting the surgical instrument into the colon to position the second surgical tool head in a second position therein. The method further includes applying a second actuation motion to the surgical instrument to cause the second surgical tool head to perform the second surgical action and withdrawing the surgical instrument from the colon.

In accordance with general aspects of various forms of the present invention, there is provided a circular stapling head for use with a modular circular surgical instrument that has an elongated shaft assembly that is configured to apply rotary drive motions. In various embodiments, the circular stapling head comprises an outer casing that is configured for releasable attachment to the elongated shaft. The outer casing operably supports at least one circular array of surgical staples therein. A staple driver is constrained for axial movement within the outer casing and is configured for driving engagement by a rotary drive shaft portion of the elongated shaft assembly when the outer casing is attached to the elongated shaft assembly. An application of a rotary drive motion from the rotary drive shaft portion to the staple driver causes the staple driver to axially drive the surgical staples out of the outer casing.

In accordance with still other general aspects of various embodiments of the present invention, there is provided a surgical grasping device for use with a modular circular surgical instrument that has an elongated shaft assembly that is configured for generating rotary drive motions. Various forms of the surgical grasping device comprise an outer casing that is configured for releasable attachment to the elongated shaft assembly. The outer casing movably supports first and second jaws thereon that are each configured to receive rotary drive motions from the elongated shaft assembly. Upon application of the rotary drive motion in a first rotary direction, the first and second movable jaws are caused to move from a closed position to an open position. Upon application of the rotary drive motion to the first and second movable jaws in a second rotary direction, the first and second movable jaws are caused to move from the open position to the closed position.

In accordance with yet other general aspects of various forms of the present invention, there is provided a kit of surgical tool heads for interchangeable use with a circular surgical instrument. In various forms, the kit comprises at least two of the circular tool heads selected from a group of circular surgical tool heads that includes a first circular stapling head that is configured for removable operable attachment to the circular surgical instrument for operably receiving a corresponding first drive motion therefrom. The group further includes a second circular stapling head that is configured for removable operable attachment to the circular surgical instrument for operably receiving a corresponding second drive motion therefrom. The group also includes a surgical grasping head that is configured for removable operable attachment to the circular surgical instrument for receiving corresponding third drive motion therefrom. The group also includes a universal port member that is configured for removable operable attachment to the circular surgical instrument for receiving at least one corresponding fourth drive motion therefrom.

In accordance with general aspects of various forms of the present invention, at least one embodiment comprises a universal port for insertion into a colon. In various forms, the universal port comprises a first ring stage that is configured to be selectively expanded from a collapsed insertion state to an expanded state upon application of a first rotary drive motion thereto and a second ring stage that is operably attached to the first ring stage and is configured to retainingly engage a portion of the colon upon application of a second rotary drive motion thereto.

In accordance with other general aspects of other forms of the present invention, in at least one embodiment, there is provided a universal port for insertion into a colon. In at least one form, the universal port comprises an annular port body that has a centrally-disposed port extending therethrough. A plurality of tissue-engaging barbs are operably supported within the annular port body and are configured for movement from a first insertion position within the annular port body to a second deployed position wherein a tissue-engaging portion thereof protrudes outward from the annular port body. A deployment drive assembly is operably supported within the annular port body and is configured to for operable engagement with a surgical instrument. The deployment drive assembly operably interfaces with each of the tissue-engaging barbs such that upon application of a drive motion from the surgical instrument in a first direction causes the tissue-engaging barbs to move from the first insertion position to the second deployed position and upon another application of the drive motion from the surgical instrument in a second direction causes the tissue-engaging barbs to move from the deployed position to the insertion position.

In accordance with still other general aspects of other forms of the present invention, in at least one embodiment, there is provided a universal port for installation within a colon. In at least one form, the universal port comprises a first annular port body that is configured to be releasably inserted within the colon by an insertion member. A second annular port body is movably coupled to the first annular port body and is configured for releasable operable engagement with a drive member for applying drive motions thereto. The second annular port body operably supports a plurality of tissue-engaging barbs around a circumference of the second annular port body that are selectively deployable from an insertion position wherein each of the tissue-engaging barbs is supported substantially within the second annular port body and a deployed position wherein the tissue-engaging tip portions thereof protrude outward from the second annular port body.

In accordance with other general aspects of other forms of the present invention, in at least one embodiment, there is provided a colon expansion port for installation within a colon. In at least one form, the colon expansion portion comprises a port body that has a proximal port end, a distal port end and a central portion that extends therebetween. The port body is selectively configurable from a collapsed insertion position and an expanded installation position. An insertion instrument is releasably attachable to the proximal end of the port body. An actuation member interfaces with the distal end of the port body to apply an actuation motion thereto for drawing the distal portion of the port body towards the proximal portion of the port body to move the port body from the insertion position to the installation position. A plurality of tissue-engaging barbs are operably supported within the port body and are movable from an un-deployed position to a deployed position when the actuation motion is applied to the distal end portion of the port body.

In accordance with other general aspects of other forms of the present invention, in at least one embodiment, there is a universal port for insertion into a colon. The universal port comprises a dilatable portion configured to be selectively expanded from a collapsed insertion state to an expanded state upon the application of a rotary drive motion thereto wherein the dilatable portion is configured to engage the colon in its expanded state. The universal port further comprises a drive portion configured to engage the dilatable portion and apply the rotary drive motion to the dilatable portion.

In accordance with other general aspects of other forms of the present invention, in at least one embodiment, there is a port for insertion into a patient's colon and use during a surgical technique using a surgical stapler, the surgical stapler including a tool head and an anvil attachable to the tool head. The port comprises a frame configured to engage the colon, an aperture extending through the frame, wherein the aperture is sized and configured to permit the anvil to be passed therethrough in a first direction and a portion of the patient's colon to be passed therethrough in a second direction. The port can further comprise a sleeve extending from the frame, wherein the sleeve is sized and configured to receive at least a portion of the tool head therein.

In accordance with other general aspects of other forms of the present invention, in at least one embodiment, there is a port for insertion into a patient's colon and use during a surgical technique using a surgical stapler, the surgical stapler including a tool head and an anvil attachable to the tool head. The port comprises a frame configured to engage the colon, means for permitting the anvil to be passed through the frame in a first direction, and means for permitting a portion of the patient's colon to be passed through the frame in a second direction.

In accordance with other general aspects of other forms of the present invention, in at least one embodiment, there is a port for insertion into a patient's colon and use during a surgical technique using a surgical stapler, the surgical stapler including a tool head and an anvil attachable to the tool head. The port comprises means for securely engaging the colon, means for permitting the anvil to be passed through the frame in a first direction, and means for permitting a portion of the patient's colon to be passed through the frame in a second direction.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the various forms of the present invention.

FIG. 3 is a partial perspective view of one embodiment of an actuation system of a modular surgical instrument embodiment of the present invention;

FIG. 9 is a cross-sectional view of the shaft assembly and surgical tool head depicted in FIG. 8;

FIG. 10 is a partial side view of one rotary drive shaft embodiment of the present invention;

FIG. 18 is a partial cross-sectional view of another surgical tool head embodiment of the present invention with the movable jaws thereof in an open position;

FIG. 19 is another partial cross-sectional view of the surgical tool head embodiment of FIG. 18 with the movable jaws thereof in a closed position;

FIG. 20 is a partial top view of a rotary adapter employed in the surgical tool head of FIGS. 18 and 19;

FIG. 21 is a partial cross-sectional view of another surgical tool head embodiment of the present invention with various component portions thereof omitted for clarity;

FIG. 22 is a partial cross-sectional view of another surgical tool head embodiment of the present invention with various component portions thereof omitted for clarity;

FIG. 23 is a partial cross-sectional view of a modular surgical instrument embodiment wherein the surgical staples have been driven horizontally through an elastic ring supported within the colon;

FIG. 24 is another partial cross-sectional view of a modular surgical instrument embodiment wherein the surgical staples have been driven horizontally through an elastic ring supported on the distal end of a shaft assembly;

FIG. 25 is another partial cross-sectional view illustrating surgical staples that have been driven horizontally through an elastic ring supported within the colon with a metal ring removably inserted into the interior of the elastic ring to prevent the elastic ring from collapsing;

FIG. 33A is a diagrammatical perspective view of the universal port embodiment of FIG. 33;

FIG. 33B is another diagrammatical perspective view of another universal port embodiment of the present invention;

FIG. 65 is a partial cross-sectional perspective view of a tissue manipulation device embodiment of the present invention inserted into the colon and engaging a portion thereof;

FIG. 66 is a cross-sectional view of a portion of the tissue manipulation device and colon of FIG. 65;

DETAILED DESCRIPTION

Figure 1:
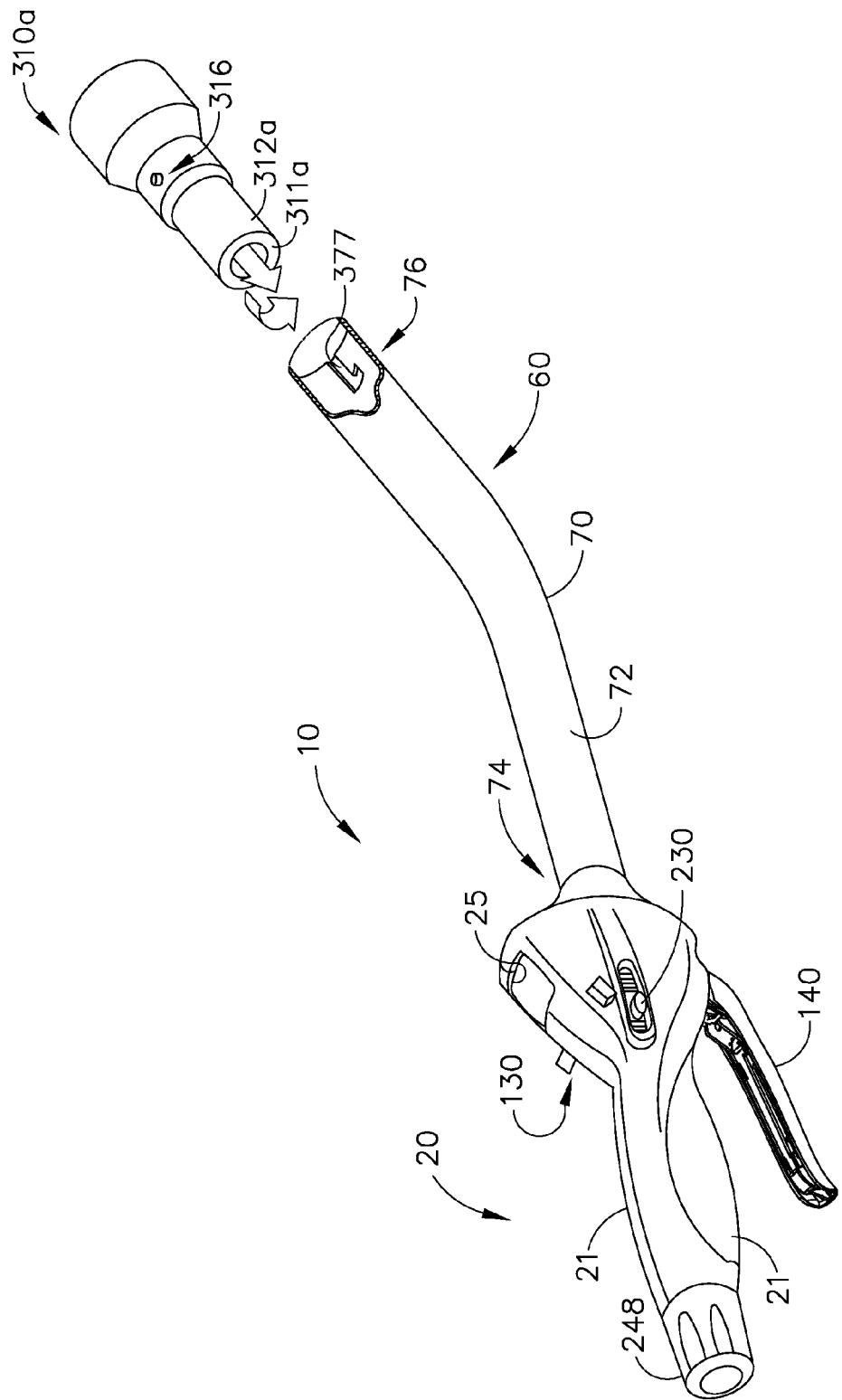
FIG. 1 is an exploded perspective view of one form of a modular surgical instrument of an embodiment of the present invention and a surgical tool head embodiment of the present invention.

The assignee of the present application also owns the following applications which were contemporaneously filed herewith and which are each herein incorporated by reference in their respective entireties:

U.S. patent application Ser. No. 13/181,798, filed Jul. 13, 2011, entitled "Modular Surgical Tool Systems";

U.S. patent application Ser. No. 13/181,779, filed Jul. 13, 2011, entitled "Multiple Part Anvil Assemblies For Circular Surgical Stapling Devices";

U.S. patent application Ser. No. 13/181,807, filed Jul. 13, 2011, entitled "Modular Tool Heads For Use With Circular Surgical Instruments";

U.S. patent application Ser. No. 13/181,831, filed Jul. 13, 2011, entitled "Tissue Manipulation Devices";

U.S. patent application Ser. No. 13/181,768, filed Jul. 13, 2011 entitled "Collapsible Anvil Plate Assemblies For Circular Surgical Stapling Devices";

U.S. patent application Ser. No. 13/181,786, filed Jul. 13, 2011, entitled "Circular Stapling Devices With Tissue-Puncturing Anvil Features";

U.S. patent application Ser. No. 13/181,774, filed Jul. 13, 2011 entitled "Anvil Assemblies With Collapsible Frames For Circular Staplers";

U.S. patent application Ser. No. 13/181,842, filed Jul. 13, 2011 entitled "Rectal Manipulation Devices";

U.S. patent application Ser. No. 13/181,836, filed Jul. 13, 2011, entitled "Surgical Access Devices With Anvil Introduction and Specimen Retrieval Structures"; and U.S. patent application Ser. No. 13/181,827, filed Jul. 13, 2011, entitled "Surgical Bowel Retractor Devices".

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment", or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation. Such modifications and variations are intended to be included within the scope of the present invention.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

FIG. 1 illustrates one form of a modular surgical instrument 10 of an embodiment of the present invention. In at least one embodiment, the modular surgical instrument 10 includes a universal actuator handle assembly 20 that is attached to an elongated shaft assembly 60 that is configured for operable attachment to a variety of different surgical tool heads. FIG. 1 illustrates a circular stapling head 310a, the attachment and operation of which will be discussed in further detail below. In the depicted embodiment, the handle assembly 20 operably supports an actuation system generally designated as 100 which is configured to selectively apply various forms of actuation motions to the particular-type of surgical tool head attached thereto. As the present Detailed Description proceeds, those of ordinary skill in the art will appreciate that portions of the various modular surgical instruments disclosed herein may be configured to operably interface with a robotic control system that can provide the requisite actuation motions to the instruments.

In various embodiments, the handle assembly 20 includes two handle case segments 21 that may be interconnected together by suitable fastener arrangements for ease of assembly. The shaft assembly 60 includes an outer shaft casing 70 that is substantially hollow and may be fabricated from two casing segments 72 that are coupled together to form a hollow conduit. The outer shaft casing 70 has a proximal end 74 that is coupled to the handle assembly 20 and an open distal end 76.

The Rotary Drive System

Figure 2:
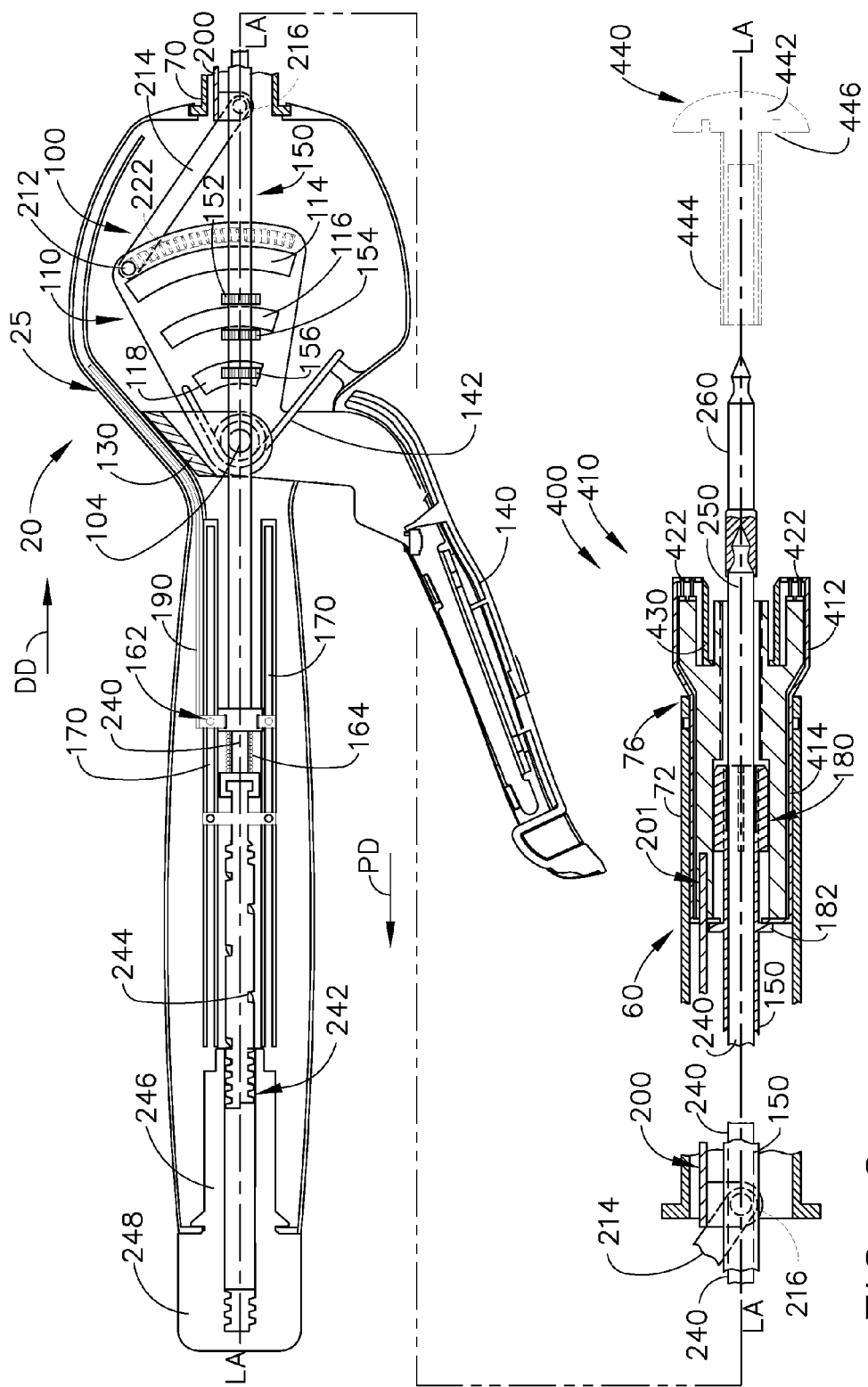
FIG. 2 is a cross-sectional view of one form of a modular surgical instrument embodiment of the present invention attached to a surgical tool head embodiment of the present invention.
Figure 3:
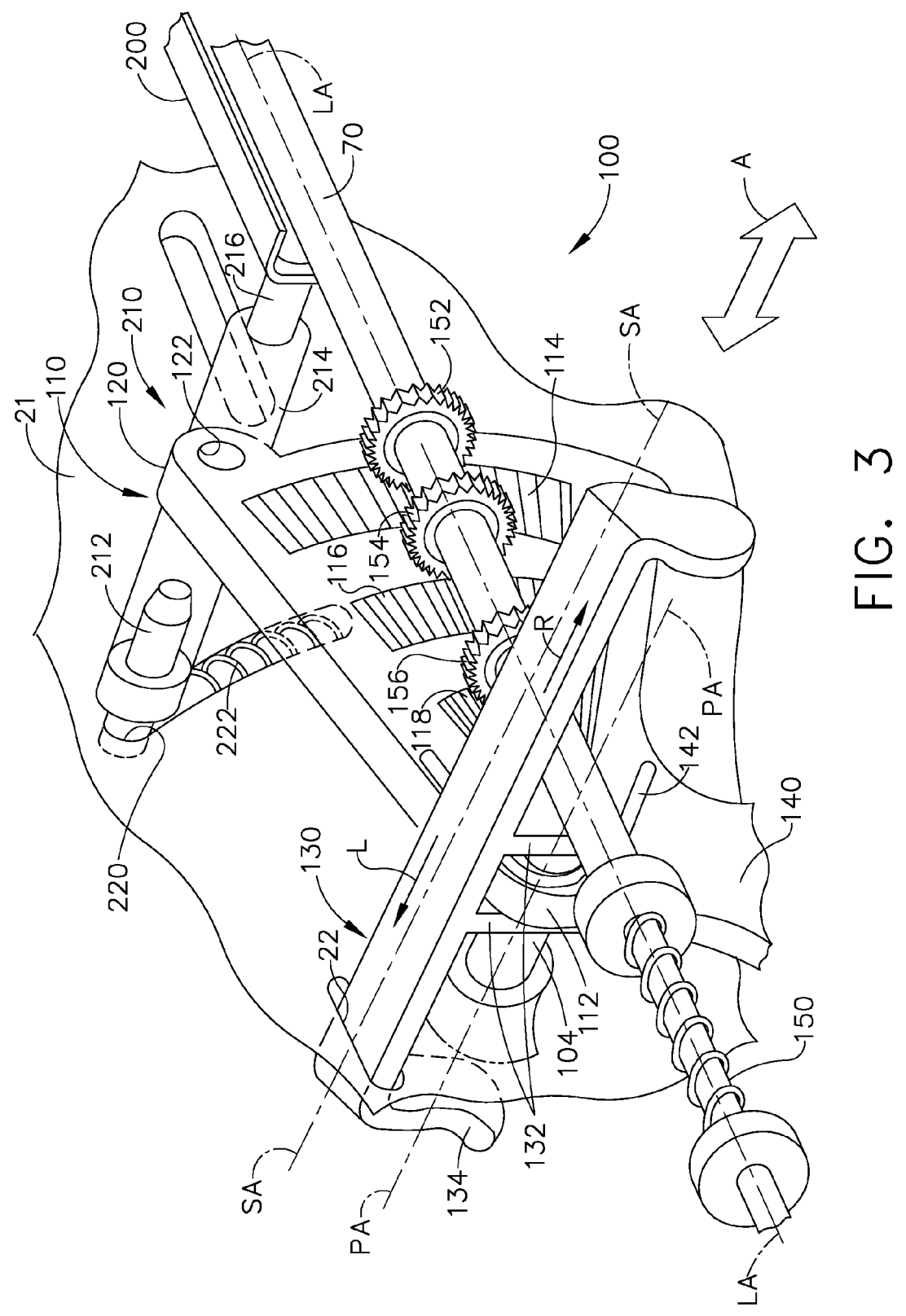
Figure 3A:
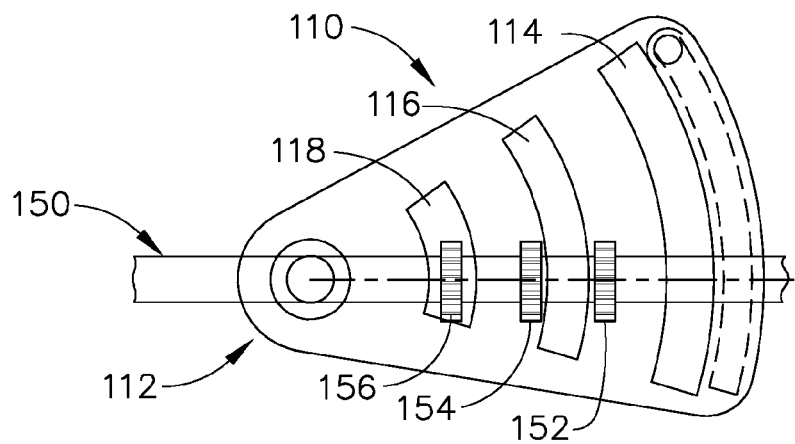
FIGS. 3A-3C are side views of a gear plate embodiment and rotary drive shaft embodiment of the present invention.
Figure 3B:
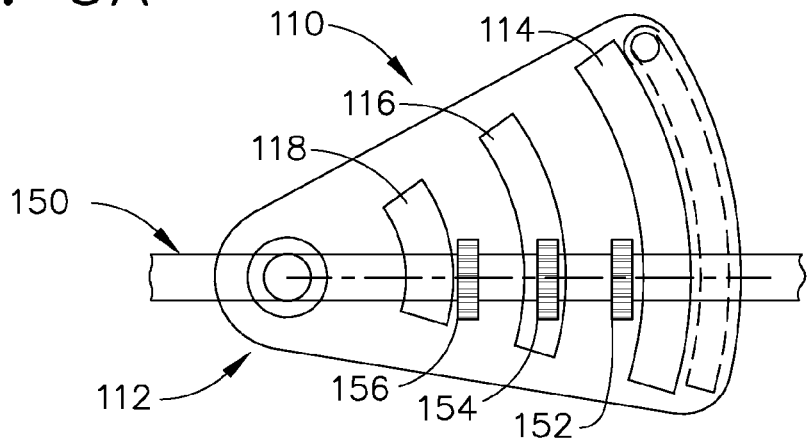
Figure 3C:
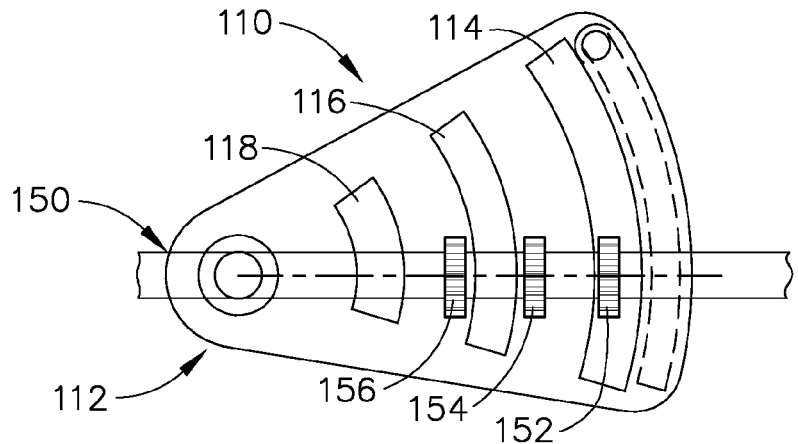

Various embodiments of the modular surgical instrument 10 include a unique and novel transmission or actuation system that facilitates the selective application of a variety of different axial and rotary motions to a particular surgical tool head attached thereto. Referring to FIGS. 2 and 3, one form of actuation system 100 includes a gear plate 110 that is pivotally supported in the handle assembly 20 for selective pivotal travel about a pivot axis PA-PA that is substantially transverse to the instrument's longitudinal axis LA-LA. The gear plate 110 may be pivotally supported within the handle assembly 20 on a pivot shaft 104 that extends between the handle case segments 21. As will be discussed in further detail below, the gear plate 110 is also laterally movable on the pivot shaft 104 from a first rotary drive position to a second axial drive position by a first drive selector switch 130 that is slidably-supported between the handle case segments 21. As can be seen in FIG. 3, the first drive selector switch 130 is provided with two downwardly protruding clevis arms 132 that are configured to receive a proximal end portion 112 of the gear plate 110 therebetween. The first drive selector switch 130 extends through slots 22 in the handle case members 21 and have down turned end portions 134 to enable the user to slide the first drive selector switch 110 laterally back and forth (arrow "A" in FIG. 3) within the handle assembly 20 along a selector axis SA-SA that is substantially transverse to the longitudinal axis LA-LA. An "actuator" in the form of a firing trigger 140 is attached to, or otherwise integrally formed with, the gear plate 110 such that the gear plate 110 may be selectively pivoted about the pivot axis PA-PA by squeezing the firing trigger 140 toward the handle assembly 20. The term "actuator" may also encompass a portion of a robotic system configured to apply the requisite actuation motion to the gear plate 110.

As can be further seen in FIG. 2, the gear plate 110 is configured to operably interact with a rotary drive shaft 150 that extends through the outer shaft casing 70 of the elongated shaft assembly 60 and is rotatably supported therein. In various embodiments the gear plate 110 has a first gear rack 114, a second gear rack 116, and a third gear rack 118 formed thereon. See FIGS. 3A-3C. The rotary drive shaft 150 has a first pinion gear 152 that is adapted for selective meshing engagement with the first gear rack 114 and a second pinion gear 154 that is adapted for selective meshing engagement with the second gear rack 116 and a third pinion gear 156 that is adapted for selective meshing engagement with the third gear rack 118. As will become further apparent as the present Detailed Description proceeds, each gear rack 114, 116, 118 defines a discrete amount of rotary travel that may be applied to the rotary drive shaft 150. For example, the first gear rack 114, when in meshing engagement with the first pinion gear 152, may facilitate an application of a first amount of rotary travel to the rotary drive shaft 150 upon application of an actuation motion to the firing trigger 140. For example, the first gear rack 114 may facilitate a first amount of rotary travel of approximately 0.70" when the firing trigger 140 is pivoted from a starting position to an ending position. The second gear rack 116, when in meshing engagement with the second pinion gear 154, facilitates a second range of rotary travel to the rotary drive shaft 150. For example, the second gear rack 116 may facilitate a second amount of rotary travel of approximately 1.41" when the firing trigger 140 is pivoted from a starting position to an ending or fully depressed position. The third gear rack 118, when in meshing engagement with the third pinion gear 156, facilitates a third amount of rotary travel of approximately 2.11" when the firing trigger 140 is pivoted from a starting position to an ending or fully depressed position. It will be understood, however, that other numbers and lengths of gear rack and pinion gear arrangements could conceivably be employed to provide other ranges of rotary motion without departing from the spirit and scope of the present invention.

Also in various handle assembly embodiments, a torsion spring 142 is employed to bias the tiring trigger 140 to the unactuated position shown in FIG. 1. Thus, in various embodiments, once the surgeon releases the firing trigger 140, the spring 142 returns the firing trigger 140 to the unactuated position and, in doing so, applies a reverse rotary motion to the rotary drive shaft 150. Various forms of known trigger safety arrangements such as those disclosed in U.S. Pat. No. 7,506,791, entitled "Surgical Stapling Instrument With Mechanical Mechanism For Limiting Maximum Tissue Compression", the disclosure of which is herein incorporated by reference in its entirety, may also be employed.

The rotary drive shaft 150 further has a proximal end 160 that is movably supported within the handle assembly for rotary and axial travel therein. In one embodiment, for example, the proximal end 160 of the rotary drive shaft 150 is configured to support a bearing assembly 162 thereon that is constrained to move in axial tracks 170 formed in the handle cases 21. See FIG. 2. The bearing assembly 162 facilitates rotation of the rotary drive shaft 150 about the longitudinal axis LA-LA while also facilitating its axial travel within the handle assembly 20 and the outer shaft casing 70 of the shaft assembly 60. As can be seen in FIG. 2, a compression spring 164 serves to axially bias the rotary drive shaft 150 in the distal direction "DD".

As can also be seen in FIGS. 2-6, the rotary drive shaft 150 is hollow and has a distal end portion 180 that is configured to operationally mate with various forms of surgical tool heads attached thereto. As will be discussed in further detail below, the distal end portion 180 has an actuator flange 182 formed thereon that is oriented for engagement by a proximal end of the particular surgical tool head or adapter arrangement coupled thereto. Thus, when a particular surgical tool head is coupled to the shaft assembly 60, its distal end contacts the actuator flange 182 to bias the rotary drive shaft 150 in the proximal direction.

Figure 4:
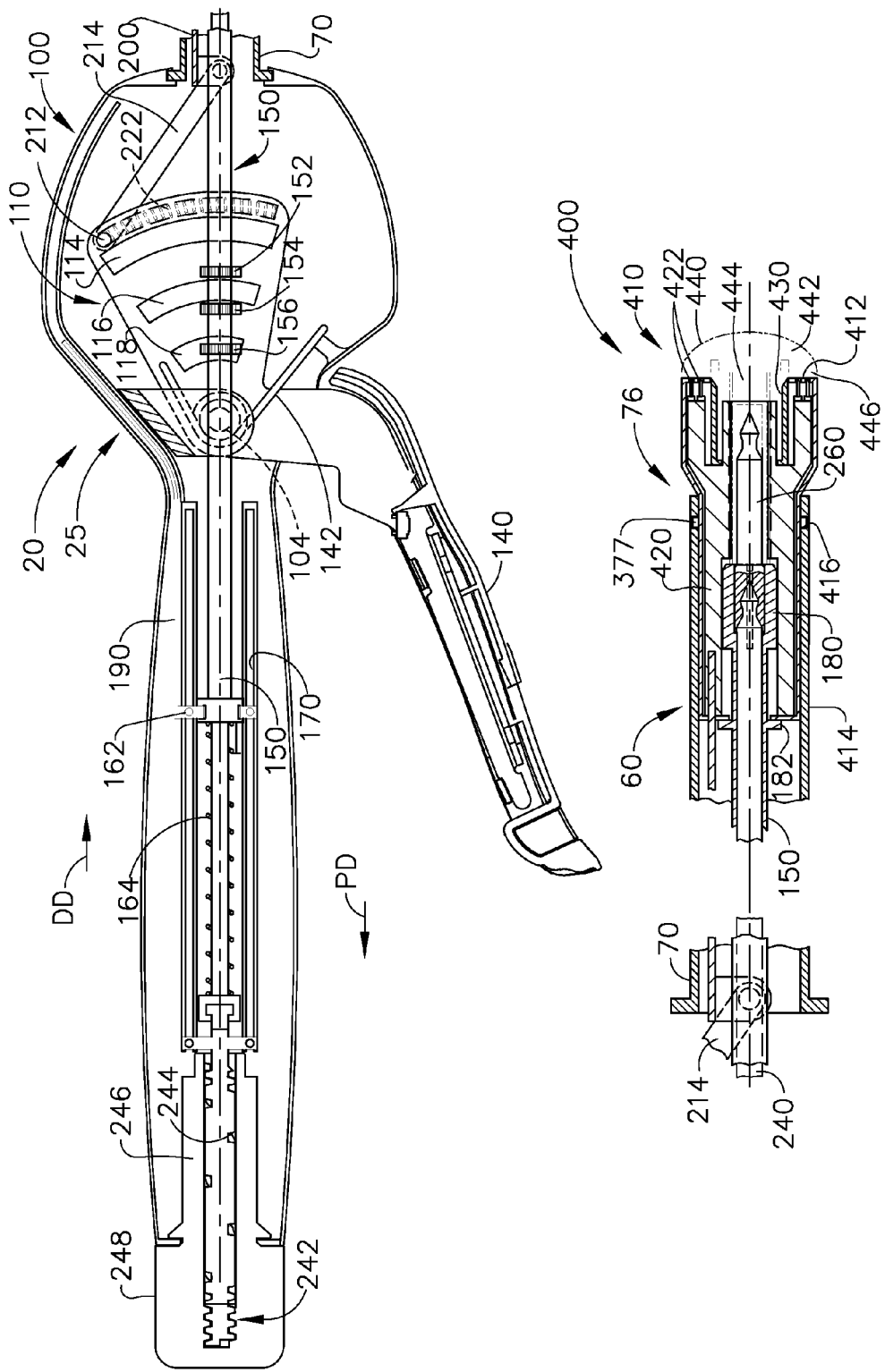
FIG. 4 is another cross-sectional view of the modular surgical instrument embodiment of and surgical tool head of FIG. 2 with an anvil (shown in phantom lines) attached thereto.

Also in various embodiments, the handle assembly 20 may have a window or opening 25 therein (FIG. 1) that facilitates viewing by the surgeon of an indicator member 190. In various embodiments, the indicator member 190 may comprise a tape member that is flexible enough to axially travel back and forth within the handle assembly 20 and be viewable through the window or opening 25. The tape member 190 is attached to the bearing assembly 162 as can be seen in FIGS. 2 and 4 and has indication indicia thereon that corresponds to the gear rack 114, 116, 118 that is engaged with its corresponding pinion gear 152, 154, 156, respectively. For example, the indicator indicia may comprise a picture, drawing, diagram, model identification number, etc. of the particular surgical tool head that requires the corresponding amount of discrete rotary travel of the rotary drive shaft 150 for actuation purposes.

The Axial Drive Systems

The instrument 10 further includes axial drive arrangements for selectively applying axial actuation motions to the various surgical tool heads attached to the shaft assembly 60. As was discussed above, a first drive selector switch 130 is configured to engage the proximal end portion 112 of the gear plate 110. Such arrangement permits the first drive selector switch 130 to be used to laterally move the gear plate 110 on the pivot shaft 104 between a first rotary drive position wherein an application of an actuation motion to the firing trigger 140 results in the application of a rotary drive motion to the rotary drive shaft 150 and a second axial drive position wherein an application of an actuation motion to the firing trigger 140 results in the application of an axial drive motion to an axial drive bar 200. More specifically and with reference to FIGS. 2-4, the axial drive bar 200 is coupled to an axial drive linkage 210 that is configured to releasably interface with the gear plate 110. As can be seen in FIG. 3, the gear plate 110 has an engagement lug 120 formed thereon that has a hole 122 that is sized to receive a first engagement pin 212 that protrudes from the axial drive linkage 210. The axial drive bar 200 is pinned to a linkage bar 214 by a pin 216 that extends through the linkage bar 214 into a slot 218 in one of the handle cases 21. As can be most particularly seen in FIG. 3, the first engagement pin 212 is also attached to the linkage bar 214 and protrudes therethrough into a second slot 220 in the handle case 21. A compression spring 222 is supported within the slot 220 to bias the pin 212 within the slot 220 to the starting position shown in FIG. 3. The axial drive bar 200 has a distal end 201 that is configured to engage a corresponding portion of the particular surgical tool head that has been coupled to the modular surgical instrument 10 to apply the requisite amount of axial-drive motion thereto.

Thus, to actuate the axial drive bar 200, the surgeon laterally moves the first drive selection switch 130 in the "L" direction to bring the pin 212 into the hole 122 in the gear plate attached lug 120. This action also moves the gear plate 110 to the axial drive position wherein all of the gear racks 114, 116, 118 are out of meshing engagement with their corresponding pinion gears 152, 154, 156 on the rotary drive shaft 150 and the gear plate 110 is in driving engagement with the axial drive bar 200. Thereafter, the surgeon may depress the firing trigger 140 to drive the axial drive bar 200 distally within the outer shaft casing 70 of the shaft assembly 60. When the surgeon releases the firing trigger 140, the springs 222 and 142 bias the gear plate 110, axial drive bar 200 and firing trigger 140 back to the starting position.

As will be discussed in further detail below, various of the surgical tool head embodiments of the present invention require rotary actuation motions to be applied to various portions of the tool head that are axially displaced from each other. Such axial displacement can be relatively small and may be accomplished without completely de-meshing one of the pinion gears 152, 154, 156 from its respective rack gear 114, 116, 118 so that activation of the firing trigger 140 results in the application of rotary motion to the rotary drive shaft 150. In at least one embodiment, a second axial drive switch 230 is employed. In various forms, the second axial drive switch 230 comprises a slider switch that can be slid between multiple positions which correspond to various axial positions of the rotary drive shaft 150. The slide switch 230 may include, for example, a clevis-type arrangement that permits the rotary drive shaft 150 to rotate relative thereto and serves to apply an axial motion to the rotary drive shaft 150 to move it axially within the handle assembly 20 and outer casing 70 of the shaft assembly 60. See FIG. 1.

Tool Component Acquisition and Operational Adjustment Drive System

Various embodiments of the modular surgical instrument 10 of the present invention include a tool acquisition shaft 240 that axially extends through the rotary drive shaft 150 and is independently movable relative thereto. In various embodiments, the proximal end portion 242 of the tool acquisition shaft 240 has a series of helical threads 244 thereon that is configured to rotatably interface with a closure nut portion 246 interfacing with an adjustment knob 248 located on the proximal end of the handle assembly 20. Such adjustment knob and closure nut arrangements are known in the art and will not be described in further detail herein. See, e.g., U.S. Pat. No. 7,506,791, the disclosure of which has been herein incorporated by reference. Thus, rotation of the adjustment knob 248 relative to the handle assembly 20 will result in the axial movement of the tool acquisition shaft 240 within the rotary drive shaft 150.

Surgical Tool Heads

As is apparent from the foregoing description, various forms of the modular surgical instrument 10 are well-suited for actuating a variety of different forms of surgical tool heads that may be required, for example, during a single surgical operation—particularly those devices/tool heads that are used to perform different surgical procedures or actions within the colon. Such surgical tool heads may be provided in a kit form wherein the kit includes at least two different surgical tool heads for use with a modular surgical instrument 10. In various embodiments, each surgical tool head has an outer casing that has an attachment stem portion that is sized to be received within the distal end 76 of the outer shaft casing 70 of the shaft assembly 60. The distance in which the attachment stem portion extends into the outer shaft casing 70 will dictate the axial position of the rotary drive shaft 150 and ultimately which pinion gear 152, 154, 156 is brought into meshing engagement with its corresponding gear rack 114, 116, 118 thereby dictating the amount of rotary drive motion applied to the rotary drive shaft 150 upon actuation of the firing trigger 140. Further understanding of this unique feature may be gleaned from reference to FIG. 7.

Figure 7:
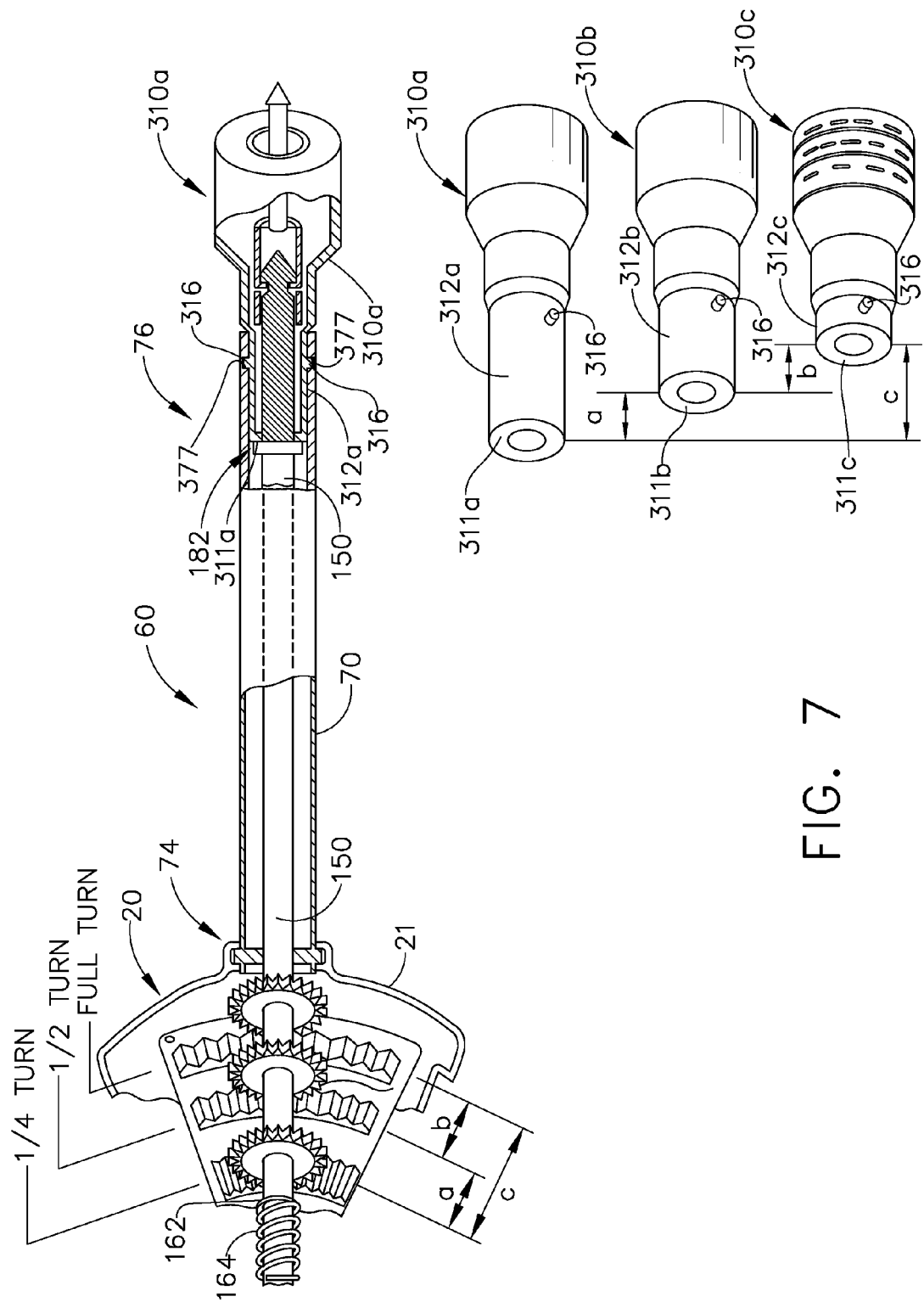
FIG. 7 is another partial cross-sectional view of the handle and shaft assembly of FIG. 6 and three different surgical tool head embodiments of the present invention.
Figure 8:
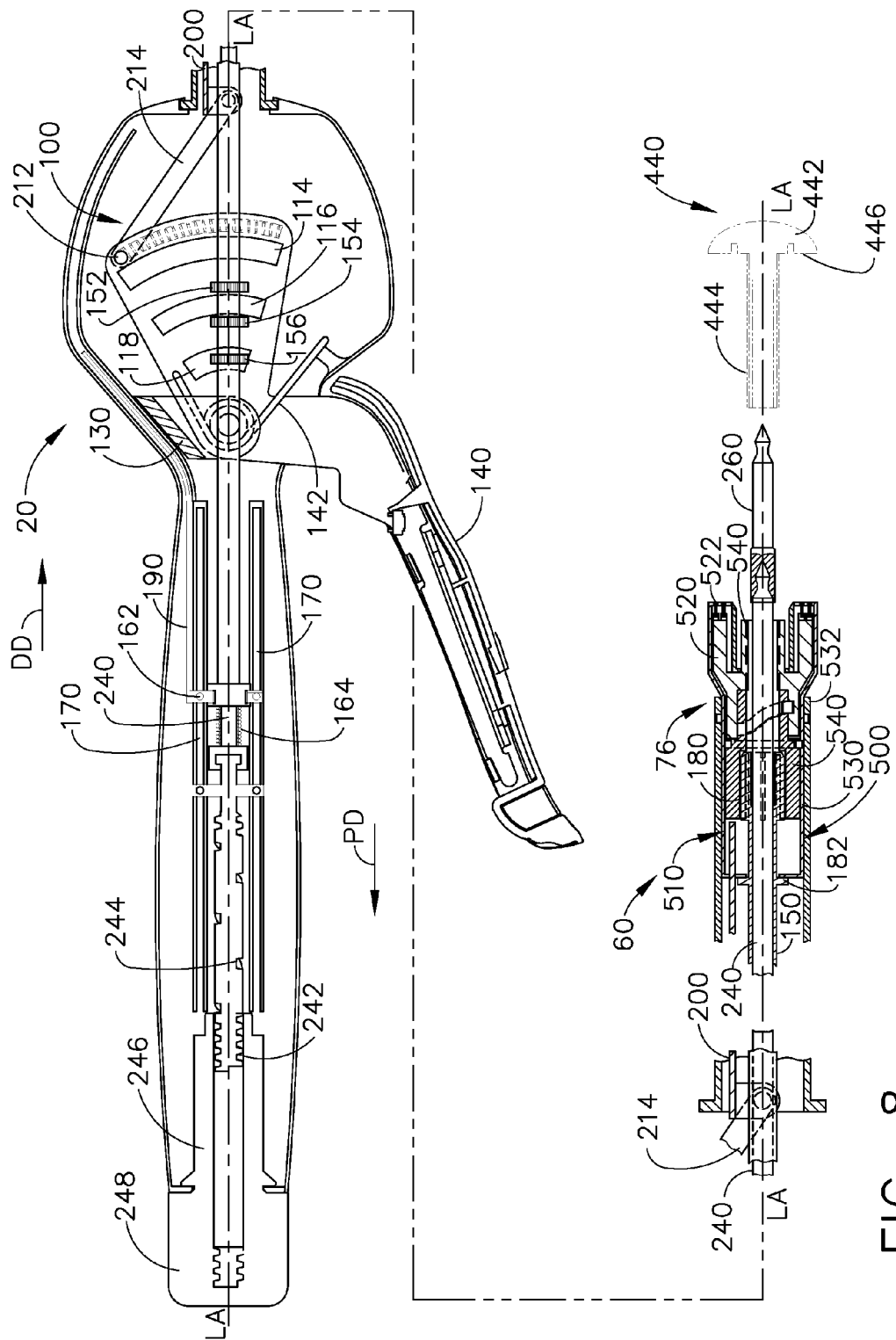
FIG. 8 is a cross-sectional view of one form of a modular surgical instrument embodiment of the present invention attached to another surgical tool head embodiment of the present invention.
Figure 11:
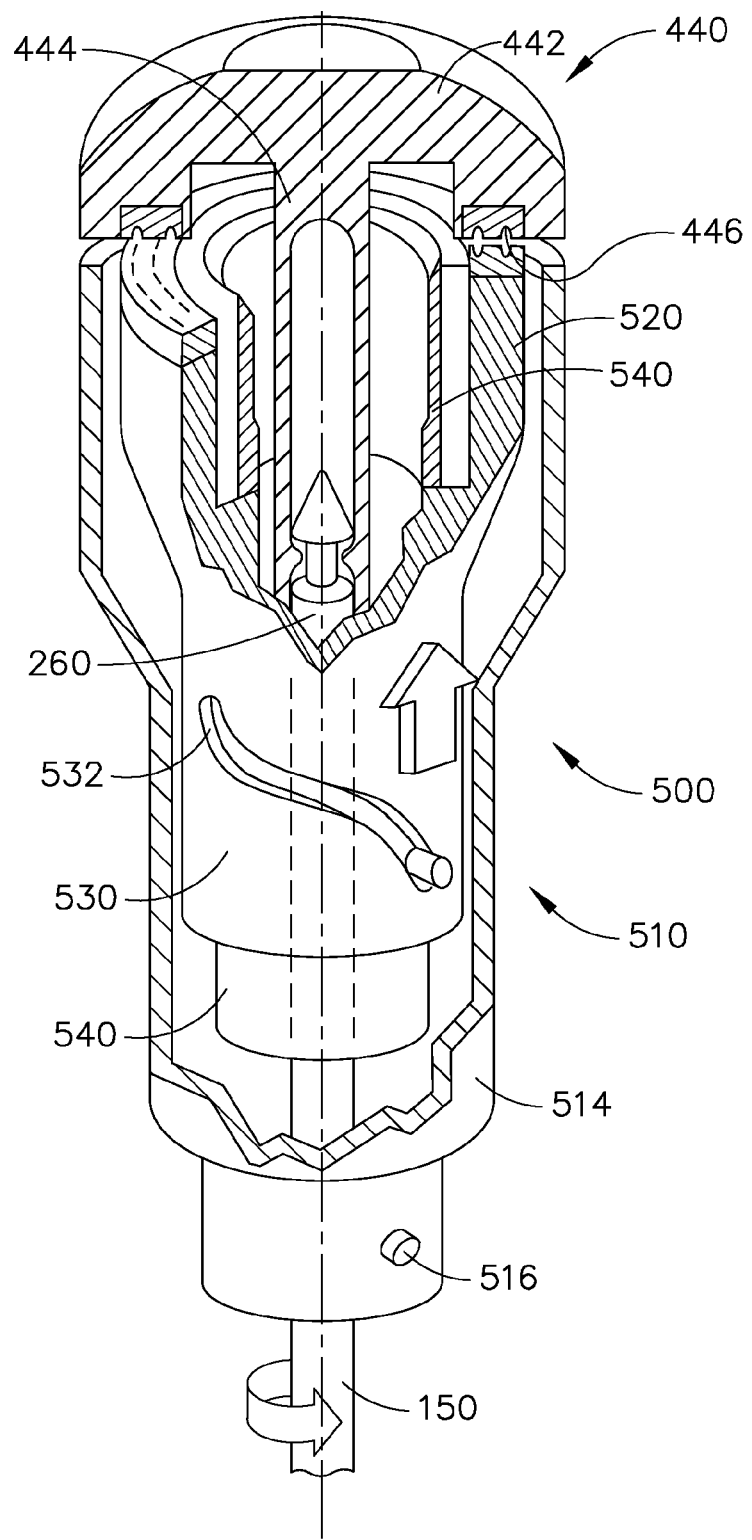
FIG. 11 is a partial cross-sectional perspective view of the surgical tool head depicted in FIGS. 8 and 9.
Figure 12:
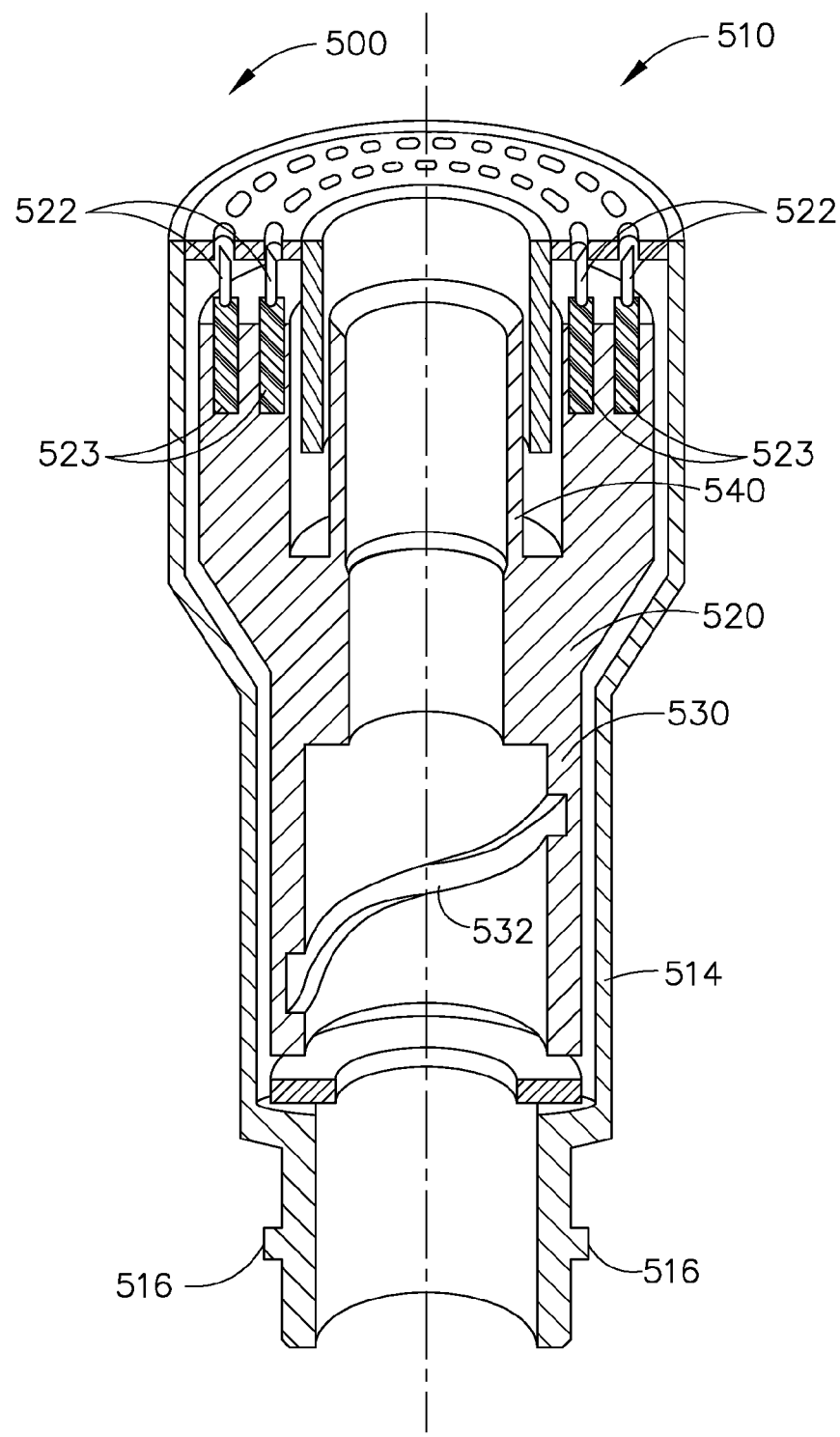
FIG. 12 is a cross-sectional view of the surgical tool head of FIG. 11.

FIG. 7 illustrates, in general form, three different forms of surgical tool heads 310a, 310b, 310c that each require three different amounts of rotary drive motion for actuation thereof. For example, tool head 310a requires ¼ turn of rotary drive motion to actuate. Tool head 310b requires ½ turn of rotary motion to actuate. Tool head 310c requires one full turn of rotary drive motion to actuate. As can also be seen in that Figure, tool head 310a has an attachment stem 312a that is configured to be inserted into the shaft assembly 60. Thus, when the attachment stem 312a is fully seated in the distal end 76 of the outer shaft casing 70, the end 311a of the attachment stem 310a engages the actuation flange 182 on the rotary drive shaft 150 and biases the rotary drive shaft 150 in the proximal direction "PD'" to bring the pinion gear 156 into meshing alignment with its corresponding gear rack 118. Likewise, tool head 310b has an attachment stem 312b that is shorter than attachment stem 312a by distance "a" which corresponds to the distance between the gear rack 118 and 116 as shown. Thus, when the attachment stem 312b is fully seated in the distal end 76 of the outer shaft casing 70, the end 311b of the attachment stem 312b engages the actuation flange 182 and biases the rotary drive shaft 150 in the proximal direction "PD'" to bring the pinion gear 154 into meshing alignment with its corresponding gear rack 116. Likewise, tool head 310c has an attachment stem 312c that is shorter than attachment stem 312a by distance "c" which corresponds to the distance between gear racks 118 and 114 and is shorter than attachment stem 312b by distance "b" which corresponds to the distance between the gear racks 116 and 114 as shown. Thus, when the attachment stem 312c is fully seated in the distal end 76 of the outer shaft casing 70, the end 311c of the attachment stem 312a engages the actuation flange 182 on the rotary drive shaft 150 and biases the rotary drive shaft 150 in the proximal direction "PD'" to bring the pinion gear 152 into meshing alignment with gear rack 114.

Various surgical tool head embodiments of the present invention also employ a "bayonet-type" attachment configuration to attach the surgical tool head to the shaft assembly 60. In particular, as can be seen in FIG. 7, each of the attachment stems 312a, 312 b, and 312c are provided with diametrically-opposed outwardly protruding pins 316. To attach a surgical tool head to the shaft assembly 60, the user aligns the pins 316 with corresponding bayonet-type slots 377 provided in the distal end 76 of the outer shaft casing 70. See FIG. 6. Once the pins 316 are aligned with their respective slots 377, the user inserts the attachment stem portion into the distal end 76 of the outer shaft casing 70 and, when seated therein, rotates the surgical tool head slightly to seat the pins 316 into their respective bayonet slots 377. In alternate embodiments, the pins may be provided on the outer shaft casing and the slots may be provided in the attachment stems.

Referring to FIGS. 2, 4, 5, and 5A, there is shown a surgical tool head 400 that may be effectively used in connection with the various embodiments of the surgical instruments 10 of the present invention. In this embodiment, the surgical tool head 400 comprises a circular stapler head 410 that only requires axial actuation motion for cutting and stapling tissue. As can be seen in those Figures, the circular stapler head 410 has an outer casing 412 that has an attachment stem portion 414 that is sized to be seated into the distal end 76 of the outer shaft casing 70. Attachment pins 416 protrude from the attachment stem 414 and are configured to be received within the bayonet slots 377 in the outer shaft casing 70. A circular staple driver 420 is movably supported within the outer casing 412. The staple driver 420 operably supports a plurality of surgical staples 422 therein in a known fashion. A tissue cutting member 430 is concentrically supported with the staple driver 420.

Figure 5:
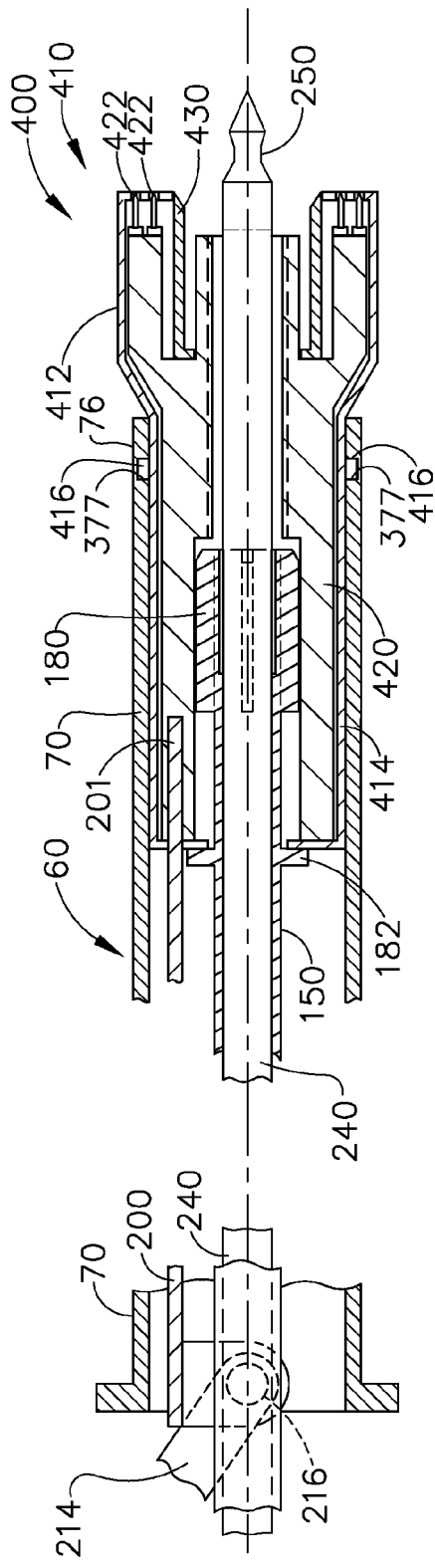
FIG. 5 is a cross-sectional view of the shaft assembly and surgical tool head depicted in FIGS. 2 and 4.
Figure 5A:
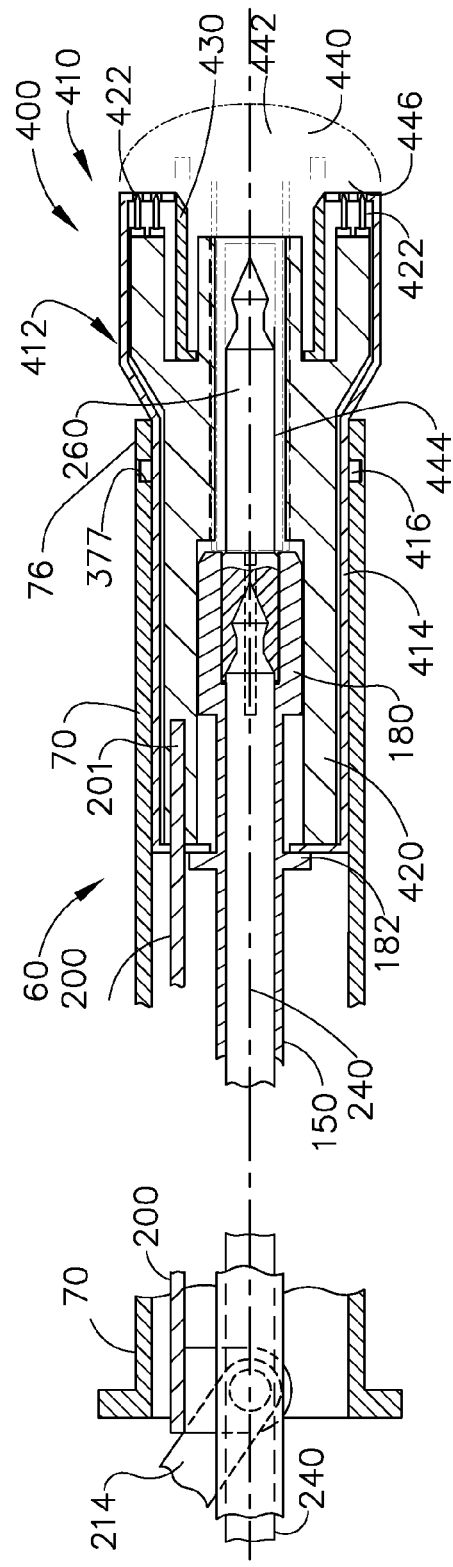
FIG. 5A is another cross-sectional view of the shaft assembly and surgical tool head depicted in FIG. 5 with an anvil (shown in phantom lines) attached thereto.
Figure 6:
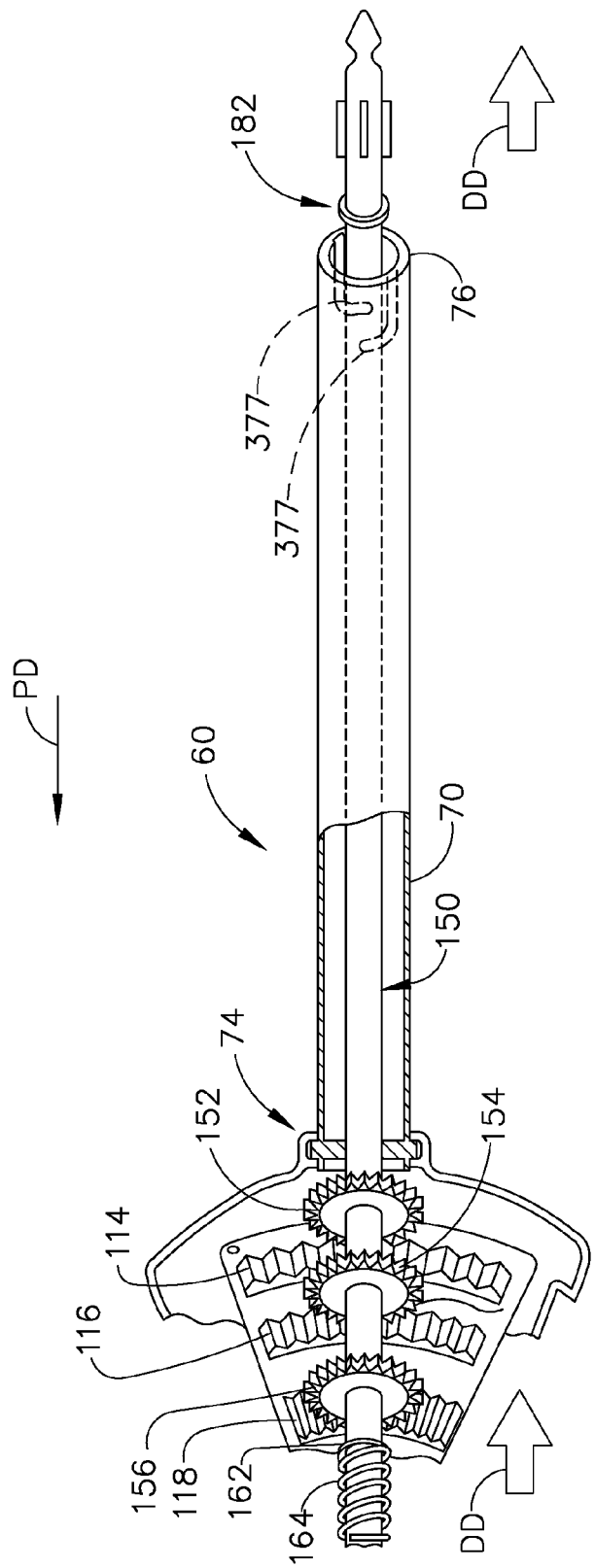
FIG. 6 is a partial cross-sectional view of the handle and shaft assembly of the modular surgical instrument of FIGS. 2 and 4.

In use, the circular stapler head 410 must be used in conjunction with an anvil 440 to form the staples therein. FIGS. 2, 4, and 5A illustrate (in broken lines) a conventional circular stapler anvil 440. Those of ordinary skill in the art will appreciate, however, that any of the various collapsible anvil arrangements disclosed in the various patent applications identified above that are presently owned by the assignee of the subject application and which have been incorporated by reference, as well as other anvil arrangements, may be employed. The depicted anvil 440 includes an anvil head 442 that is attached to an anvil stem 444. The anvil head 442 has a staple-forming surface 446 formed thereon that is adapted for confronting relationship with the surgical staples in the staple head 410.

Use of the surgical tool head 400 will now be described. Prior to installing the surgical tool head 400 onto the shaft assembly 60 of the modular surgical instrument 10, the user may bias the first drive selector switch 130 to move the gear plate 110 out of driving engagement with the rotary drive shaft 150 and into driving engagement with the axial drive bar 200. Thus, when the attachment stem 414 of the surgical tool head 400 is inserted into the distal end 76 of the outer shaft casing 70, in at least one embodiment, the rotary drive shaft 150 may be biased axially in the proximal direction without regard to the meshing alignment between the pinion gears 152, 154, 156 and the gear racks 114, 116, 118. In such circumstances, the stem 414 of the tool head 400 can contact the flange 182 extending from the rotary drive shaft 150 and push the drive shaft 150 axially against the biasing force applied by spring 164, as described above. In certain other embodiments, the rotary drive shaft 150 may be biased axially in the proximal direction by the attachment stem 414 without first moving the gear plate 110 out of driving engagement with the gears 152, 154, 156. In at least one such embodiment, the proximal end and/or distal end of each gear 152, 154, 156 may each include a beveled and/or radiused surface which can facilitate the alignment and/or realignment of the gears 152, 154, 156 with their respective gear racks 114, 116, 118, in the event that this is desirable. If the axial motion of the drive bar 200 is desired without the rotation of the rotary drive shaft 150, the gear plate 110 can be disengaged from the drive shaft via selector switch 130 as described above. In any event, the attachment stem 414 of the surgical tool head 400 can be seated in the outer shaft casing 70 and locked in position using the bayonet-type connection arrangement described above. Furthermore, when the surgical tool head 400 is attached to the shaft assembly 60, the distal end 201 of the axial drive bar can 200 seatingly engage the circular stapler driver 420. See FIGS. 2, 4, 5, and 5A. Prior to or after securing the tool head 400 to the shaft assembly 60, in certain embodiments, the user can rotate the control knob 248 at the proximal end of the handle assembly 20 to distally advance the distal end 250 of the adjustment shaft 240 and to enable the user to install a trocar shaft extension 260 thereon. In at least one embodiment, the trocar shaft extension 260 is configured to removably snap onto the distal end 250 of the adjustment shaft 240.

In use, the anvil 440 is introduced into the portion of colon to be cut and stapled using any suitable techniques including any conventional surgical techniques, any of the techniques described in the aforementioned patent applications, or any of the techniques disclosed herein. In order to assemble the anvil 440 to the surgical instrument 10, as described above, the user can insert the portion of the modular surgical instrument 10 supporting the surgical tool head 400 into the colon through the patient's anus and into the portion of the colon to be resected. The surgeon can then manipulate the modular surgical instrument 10 to bring the trocar shaft extension 260 into retaining engagement with the anvil stem 444. Once the anvil stem 444 is attached to the trocar shaft extension 260, the user then rotates the adjustment knob 248 to move the anvil head 442 towards the staple head 410 to capture the tissue to be cut and stapled therebetween. Once the surgeon has moved the anvil head 442 into its final position, the user then squeezes the firing trigger 140 which drives the axial drive bar 200 distally. As the axial drive bar 200 is driven distally, the circular staple driver 420 is driven towards the anvil head 442 thereby driving the surgical staples 422 supported therein into forming engagement with the underside 446 of the anvil head 440 and the cutting knife 430 through the captured tissue. Once the cutting and stapling action has been completed, the user may release the firing trigger 140 to permit the springs 222 and 142 to return the axial drive bar 200 and the firing trigger 140 to the starting position. Thereafter, the surgeon may withdraw the modular surgical instrument 10 from the patient.

Figure 13:
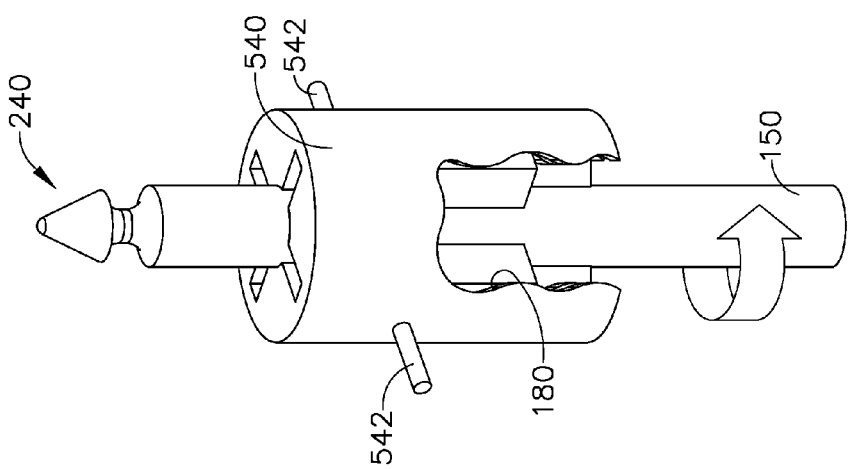
FIG. 13 is a partial perspective view of a portion of the rotary drive shaft and an adapter cap embodiment of the present invention.

FIGS. 8, 9, 11, and 12 illustrate another surgical tool head 500 that may be effectively used in connection with the various embodiments of the modular surgical instrument 10 of the present invention. In this embodiment, the surgical tool head 500 comprises another form of circular stapler head 510. This surgical tool head embodiment requires the application of a rotary drive motion thereto to cause the surgical tool head to cut and staple tissue. As can be seen in FIGS. 8, 9, 11, and 12, the circular stapler head 510 has an outer casing 512 that has an attachment stem portion 514 that is sized to be seated into the distal end 76 of the outer shaft casing 70. Attachment pins 516 protrude from the attachment stem 514 and are configured to be received within the bayonet slots 377 in the outer shaft casing 70. A circular staple driver 520 is movably supported within the outer casing 512. The staple driver 520 operably supports a plurality of surgical staples 522 therein on driver 520 or support members 523 in a known fashion. A tissue cutting member 541 is concentrically attached to the staple driver 520. As can also be seen in FIGS. 11 and 12, the staple driver 520 has a stem portion 530 that has at least one and preferably a pair of helical drive slots 532 therein. The drive slots 532 are configured to receive corresponding drive pins 542 therein that protrude from an adapter cap 540. As can be seen in FIG. 10, the distal end 180 of the rotary drive shaft 150 has a splined outer surface 181 or is fitted with fins for non-rotatably interfacing with the adapter cap 540. Thus, when the user inserts the attachment stem 514 into the distal-end 76 of the outer shaft casing 70, the adapter cap 540 slides over the distal end portion 180 of the rotary drive shaft 150 such that rotation of the rotary drive shaft 150 results in rotation of the adapter cap 540. See FIG. 13.

Use of the surgical tool head 500 will now be described. Prior to installing the surgical tool head 500 onto the shaft assembly 60 of the modular surgical instrument 10, the user may bias the first drive selector switch 130 on the handle assembly 20 to move the gear plate 110 out of driving engagement with the rotary drive shaft 150. The attachment stem 514 of the surgical tool head 500 is inserted into the distal end 76 of the outer shaft casing 70 and is affixed thereto in the manner described above. Thus, when the attachment stem 514 of the surgical tool head 500 is inserted into the distal end 76 of the outer shaft casing 70, in at least one embodiment, the rotary drive shaft 150 may be biased axially in the proximal direction without regard to the meshing alignment between the pinion gears 152, 154, 156 and the gear racks 114, 116, 118. In such circumstances, the stem 514 of the tool head 500 can contact the flange 182 extending from the rotary drive shaft 150 and push the drive shaft 150 axially against the biasing force applied by spring 164, as described above. In certain other embodiments, the rotary drive shaft 150 may be biased axially in the proximal direction by the attachment stem 514 without moving the gear plate 110 out of driving engagement with the gears 152, 154, 156. In at least one such embodiment, the proximal end and/or distal end of each gear 152, 154, 156 may each include a beveled and/or radiused surface which can facilitate the alignment and/or realignment of the gears 152, 154, 156 with their respective gear racks 114, 116, 118, as appropriate, when the rotary drive shaft 150 is displaced relative to the gear plate 110. In this embodiment, the circular stapling head 510 may require a ½ rotary turn, for example, to cut and staple tissue. Thus, in this embodiment, the attachment stem 514 is sized to position the rotary drive shaft 150 such that the pinion gear 154 is in alignment with gear rack 116. In the event that the gear plate 110 had been previously displaced by the selector switch 130, the surgeon may move the selector switch 130 to bring the gear rack 116 into meshing engagement with the pinion gear 154. Prior to or after securing the surgical tool head 500 to the shaft assembly 60, similar to the above, the user may rotate the control knob 248 to distally advance the distal end 250 of the adjustment shaft 240 and to enable the user to install a trocar shaft extension 260 thereto. The trocar shaft extension 260 is configured to removably snap onto the distal end 250 of the adjustment shaft 240.

The anvil 440, for example, is then attached to the trocar shaft extension 260 and is brought into confronting relationship with the staple driver 520 as described above. Once the surgeon has moved the anvil head 442 into the final position, the user then squeezes the firing trigger 140 which rotates the rotary drive shaft 150 and the adapter cap 540 thereon. As the adapter cap 540 rotates, the pins 542, by virtue of their engagement with the slots 532 in the staple driver 520, drive the staple driver 520 distally. Such axial motion causes the surgical staples 422 to be driven into forming engagement with the underside 446 of the anvil head 442 and the cutting knife 541 to be driven through the captured tissue. Once the cutting and stapling action has been completed, the user may release the firing trigger 140 to permit the springs 142, 222 to return the axial drive bar 200 and the firing trigger 140 to the starting position. Thereafter, the surgeon may withdraw the modular surgical instrument 10 and surgical tool head 500 from the patient.

Figure 16:
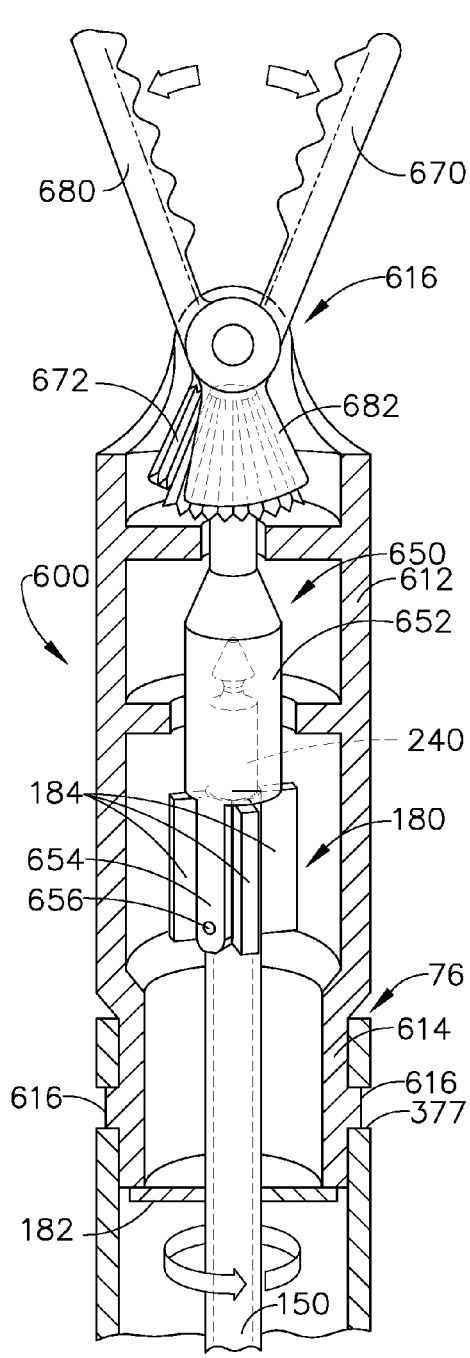
FIG. 16 is a partial cross-sectional view of another surgical tool head embodiment of the present invention with the movable jaws thereof in an open position.
Figure 17:
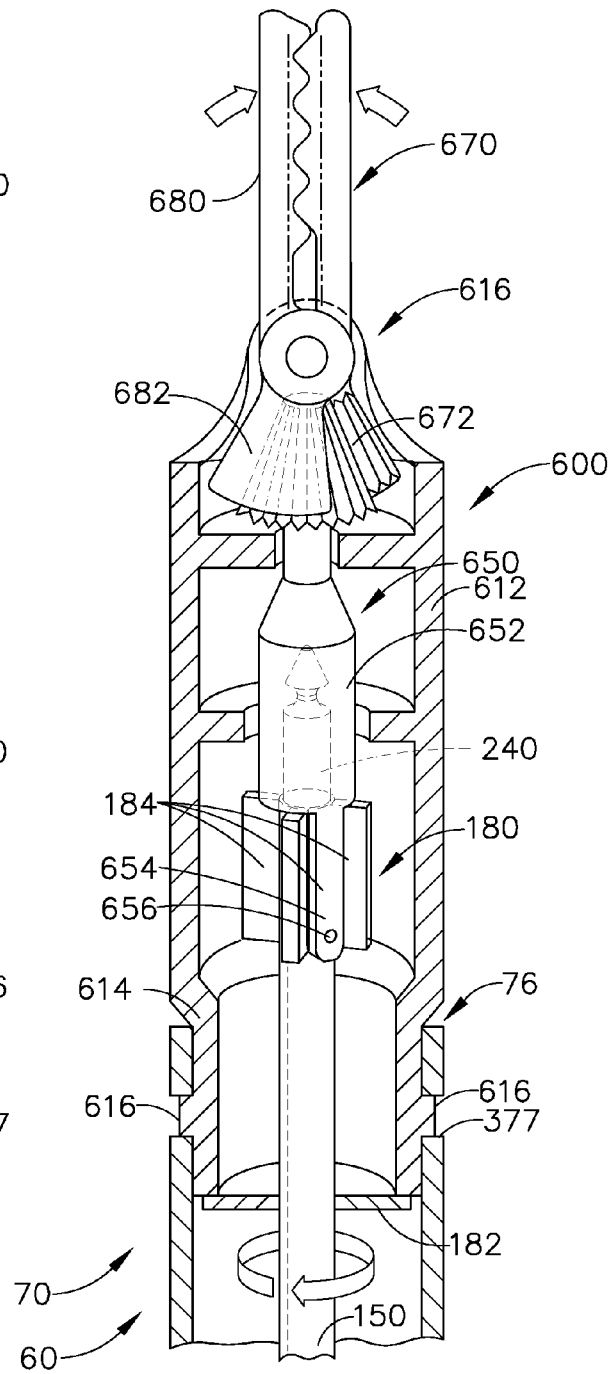
FIG. 17 is another partial cross-sectional view of the surgical tool head embodiment of FIG. 16 with the movable jaws thereof in a closed position.

FIGS. 16 and 17 illustrate another surgical tool head embodiment 600 that may be effectively used in connection with various embodiments of the modular surgical instruments 10 of the present invention. In this embodiment, the surgical tool head 600 comprises a grasper head 610. This embodiment requires the application of a rotary drive motion to actuate the two movable jaws 670, 680 thereof. As can be seen in those Figures, the grasper head 610 has an outer casing 612 that has an attachment stem portion 614 that is sized to be seated into the distal end 76 of the outer shaft casing 70. Attachment pins 616 protrude from the attachment stem 614 and are configured to be received within the bayonet slots 377 in the outer shaft casing 70. The first and second movable jaws 670, 680 are pivotally pinned to the distal end 616 of the casing 612 for pivotal travel about a common pivot axis between an open position (FIG. 16) and a closed position (FIG. 17). The first movable jaw 670 has a first gear portion 672 and the second movable jaw 680 has a second gear portion 682.

Figure 15:
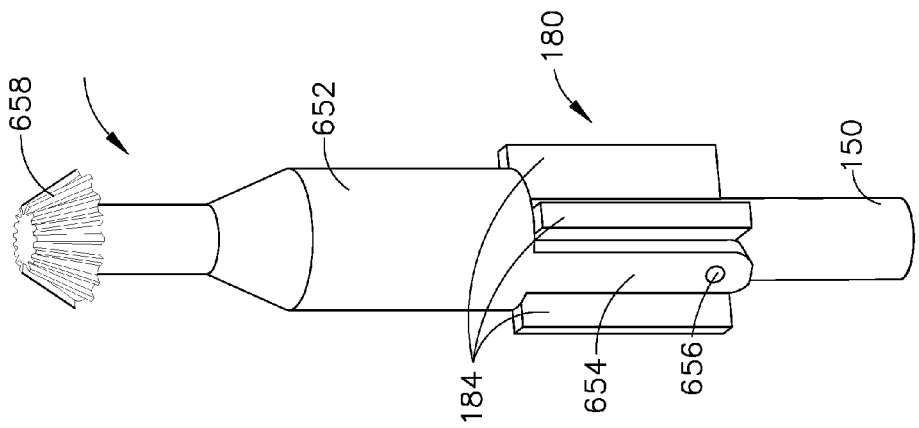
FIG. 15 is an assembled view of the rotary drive shaft and gear drive adapter shaft embodiment of FIG. 14.
Figure 14:
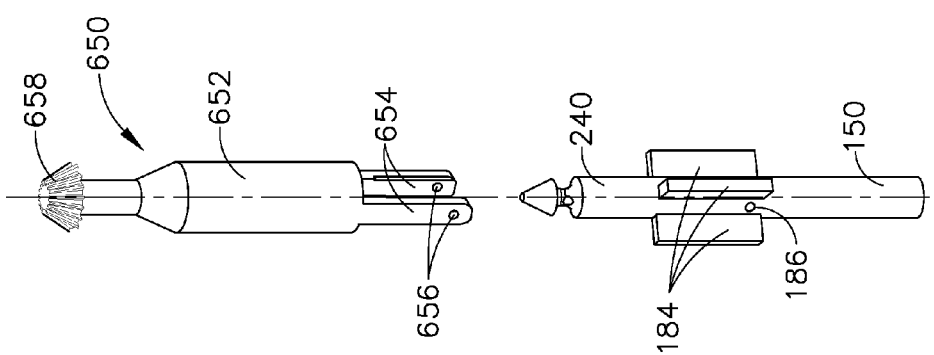
FIG. 14 is an exploded perspective view of a rotary drive shaft embodiment and a gear drive adapter shaft embodiment of the present invention.

As can be seen in FIG. 14, the distal end 180 of the rotary drive shaft 150 has a plurality of (four) fins 184 protruding therefrom for attachment with a gear drive adapter shaft 650. As can be seen in FIGS. 14 and 15, the gear drive adapter shaft 650 has a body portion 652 that has two attachment arms 654 protruding therefrom. Each attachment arm 654 has a hole or dimple 656 therein that is adapted to retainingly engage a corresponding decent 186 formed on the distal end portion 180 of the rotary drive shaft 150. In addition, the distal end of the gear drive adapter shaft 650 has a drive gear 658 formed thereon adapted to meshingly engage the gear portions 672 and 682 on the first and second movable jaws 670, 680 respectively.

Use of the surgical tool head 600 will now be described. Prior to installing the surgical tool head 600 onto the shaft assembly 60 of the modular surgical instrument 10, the user may bias the first drive selector switch 130 on the handle assembly 20 to move the gear plate 110 to a neutral position out of driving engagement with the rotary drive shaft 150. The attachment stem 614 of the surgical tool head 600 is inserted into the distal end 76 of the outer shaft casing 70 and is affixed thereto in the manner described above. In this embodiment, to move the jaws 670, 680 between the open and closed positions, the gear drive adapter shaft 650 may require a ¼ rotary turn, for example. Thus, the attachment stem 614 is sized to position the rotary drive shaft 150 such that the pinion gear 154 is in alignment with gear rack 116. Thereafter the surgeon may move the first drive selector switch 130 to bring the gear rack 116 into meshing engagement with the pinion gear 154. However, as indicated above, the rotary drive shaft 150 may also be moved axially relative to the gear plate 110 without first moving the gear plate 110 to the neutral position. Prior to securing the surgical tool head 600 to the shaft assembly 60, the user rotates the control knob 248 on the proximal end of the handle assembly 20 to proximally advance the distal end 250 of the adjustment shaft 240 to its proximal-most position. When the attachment stem 614 is inserted into the distal end 76 of the outer shaft casing 70, the gear drive adapter shaft 650 is coupled to the distal end 180 of the rotary drive shaft 150 in the above described manner. The user may then rotate the gear drive adapter shaft 650 to move the jaws 670, 680 to the closed position by squeezing the firing trigger 140. When the user releases the firing trigger, a reverse rotary motion will be applied to the gear drive adapter shaft 650 to pivot the jaws 670, 680 to the open position.

FIGS. 18-20 illustrate another surgical tool head embodiment 700 that may be effectively used in connection with the various embodiments of the modular surgical instruments 10 of the present invention. In this embodiment, the surgical tool head 700 comprises a grasper head 710. This embodiment requires the application of a rotary drive motion to actuate the two movable jaws 770, 780 thereof. As can be seen in those Figures, the grasper head 710 has an outer casing 712 that has an attachment stem portion 714 that is sized to be seated into the distal end 76 of the outer shaft casing 70. Attachment pins 716 protrude from the attachment stem 614 and are configured to be received within the bayonet slots 377 in the outer shaft casing 70. The first and second movable jaws 770, 780 are pivotally pinned to the distal end 716 of the casing 712 for pivotal travel about a common pivot axis between an open position (FIG. 18) and a closed position (FIG. 19). The first movable jaw 770 has a first actuator rod 772 protruding therefrom and the second movable jaw 780 has a second actuator rod 782 protruding therefrom.

This embodiment employs a rotary adapter member 790 that has a central aperture 792 shaped to non-rotatably receive the distal end portion 180 of the rotary drive shaft 180 therein. See FIG. 20. When installed as shown in FIGS. 18 and 19, the first actuator rod 772 extends into a first arcuate actuation slot 794 and the second actuator rod 782 extends into a second arcuate actuation slot 796 in the rotary adapter member 790. Thus, when the user rotates the rotary drive shaft 150 in the above-described manners, the rotary adapter 790 is also rotated which drives the first and second movable jaws 770, 780 to the closed position by virtue of the interaction between the first and second actuator rods 772, 782 and their respective actuation slots 784, 796, respectively. When the user releases the firing trigger a reverse rotary motion will be applied to the rotary adapter 790 to pivot the jaws 770, 780 to the open position.

FIG. 21 illustrates another surgical tool head embodiment 800 that may be effectively used in connection with the various embodiments of the modular surgical instruments 10 of the present invention. In this embodiment, the surgical tool head 800 comprises a circular stapler head 810 that has an outer casing 812 that supports a circular staple cartridge 820 therein. The anvil has been omitted from the Figure for clarity. However, the reader will understand that, except for the differences noted below, the circular stapler head 810 may otherwise operate in the same manner as the stapling heads described above. The circular staple cartridge 820 movably supports an outer circular array 822 of staple drivers 824 and an inner circular array 826 of staple drivers 827. Each staple driver 824, 827 supports one or more surgical staples 828 thereon. This embodiment requires the application of a rotary drive motion to a rotary drive assembly 830 that is rotatably supported within the circular staple cartridge 830 and non-rotatably attached to the distal end 180 of the rotary drive shaft 150 in the above-mentioned manners. The rotary drive assembly 830 includes a driver member 832 that is attached thereto that supports an outer driver wedge 834 configured to drivingly engage the drivers 824 and an inner driver wedge 836 configured to drivingly engage the drivers 826 as the rotary drive assembly 830 is rotated. Once the stapler head 810 has been attached to the shaft assembly 60 in the above-described manner, the user may apply rotary motion to the rotary drive shaft 150 and rotary drive assembly 830. This embodiment requires a full turn of rotary motion. Thus, the attachment stem 814 of the circular stapler head 810 is sized to move the rotary drive shaft 150 such that the pinion gear 152 is brought into meshing alignment with the gear rack 114. Rotary motion is then applied to the rotary drive shaft 150 and rotary drive assembly 830 by depressing the firing trigger 140. As the rotary drive assembly 830 is rotated about the longitudinal axis LA-LA, the outer drive wedge 834 sequentially contacts the outer drivers 824 to sequentially drive the surgical staples 828 supported thereon axially into forming contact with the anvil (not shown). Likewise, as the rotary drive assembly 830 is rotated about the longitudinal axis LA-LA, the inner drive wedge 836 sequentially contacts the inner drivers 826 to sequentially drive the surgical staples 828 supported thereon axially into forming engagement with the anvil. FIG. 22 illustrates a surgical tool head 800' that comprises a circular stapler head 810' that is substantially the same as the circular stapler head 810, except in that embodiment, the drive wedges 834, 836 are integrally formed in the rotary drive adapter 830'.

FIG. 23 illustrates surgical staples 828 that have been driven "horizontally" through an elastomeric retainer ring 850. In this context, the term "horizontally" means that the staples are driven in directions that are substantially transverse to the longitudinal axis LA-LA. During at least one surgical technique, the rectal tissue R can be pulled proximally into the distal end 76 of the outer shaft casing 70 and positioned along the inner sidewall thereof. In various circumstances, a grasper can be inserted upwardly through the outer shaft casing 70 and engaged with the rectal tissue R such that the rectal tissue can then be pulled downwardly into the shaft casing 70. In certain applications, the grasper can include an expandable portion, such as those described herein, for example, which is configured to expand outwardly and engage the rectal tissue. Once engaged with the tissue, the expandable portion of the grasper can be retracted inwardly prior to and/or as the expandable portion is being pulled into the outer shaft casing 70. Once the rectal tissue R has been suitably positioned, a tool head attached to the surgical instrument 10 can be inserted upwardly through the outer shaft casing 70 and positioned relative to the rectal tissue. In various embodiments, the tool head can comprise an annular staple cartridge including staple cavities and staple drivers which can be configured to eject the staples 828 laterally. In at least one such embodiment, the staples 828 and the staple drivers can be horizontally supported around the circumference of the staple cartridge and, likewise, the drive wedge(s) of the tool head and/or staple cartridge can be orientated horizontally to drivingly contact the staple drivers as the drive assembly is rotated.

Further to the above, in various embodiments, the staple cartridge can further comprise the elastomeric retainer ring 850 positioned around the outer surface of the staple cartridge wherein, as the staples 828 are deployed from the staple cartridge, the staples 828 can penetrate the retainer ring 850. In various other embodiments, the ring 850 can be positioned relative to the rectal tissue R before the tool head of the surgical instrument is positioned within the outer shaft casing 70. Once the tool head and staple cartridge are positioned, though, the staples 828 can be driven through the elastomeric retainer ring 850 into the distal end 76 of the outer shaft casing 70 and formed thereby. In at least one such embodiment, the distal end portion 76 of the outer shaft casing 70 may include a hardened anvil insert against which the staples can be deformed. In certain embodiments, the tool head and/or staple cartridge can comprise one or more drive wedges which are rotated about an axis in order to sequentially deploy the staples 828 from the staple cartridge. In certain other embodiments, the tool head and/or staple cartridge can include a cone shaped, or frustoconical, drive wedge which can be displaced distally along an axis and cam, or displace, the staple drivers and the staples 828 simultaneously. In any event, the arrangements described herein can deploy staples within a plane that is substantially perpendicular or substantially transverse to the longitudinal tool axis, although other embodiments are envisioned in which the staples are deployed within any other suitably-oriented plane, for example.

Further to the above, referring now to FIG. 24, a surgical instrument configured to deploy staples horizontally, laterally, radially, or traversely relative to the instrument axis may be used with or without a retaining ring. In such embodiments, the staples 828 can be deployed directly into the rectal tissue R. Whether or not a retaining ring is utilized, referring now to FIG. 25, a stiffening ring can be utilized to at least temporarily stiffen the staple rectal tissue. In various embodiments, a rigid ring 852 can be inserted through the outer shaft casing 70, for example, and fitted within the rectal tissue adjacent to the staple line in order to hold the overall shape of the rectum. In at least one embodiment, the rigid ring 852 can be comprised of metal, for example. Once the rigid ring 852 is no longer needed, a removal tool can be inserted through the rectum to pull the rigid ring 852 out of the surgical site.

Figure 27:
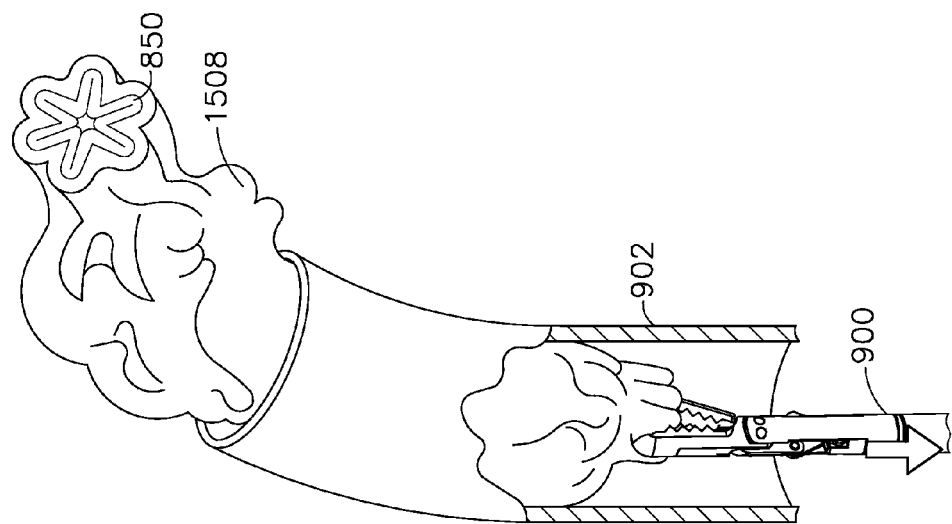
FIG. 27 is a partial cross-sectional perspective view of a severed portion of the colon being pulled through a tube inserted through the rectum.
Figure 26:
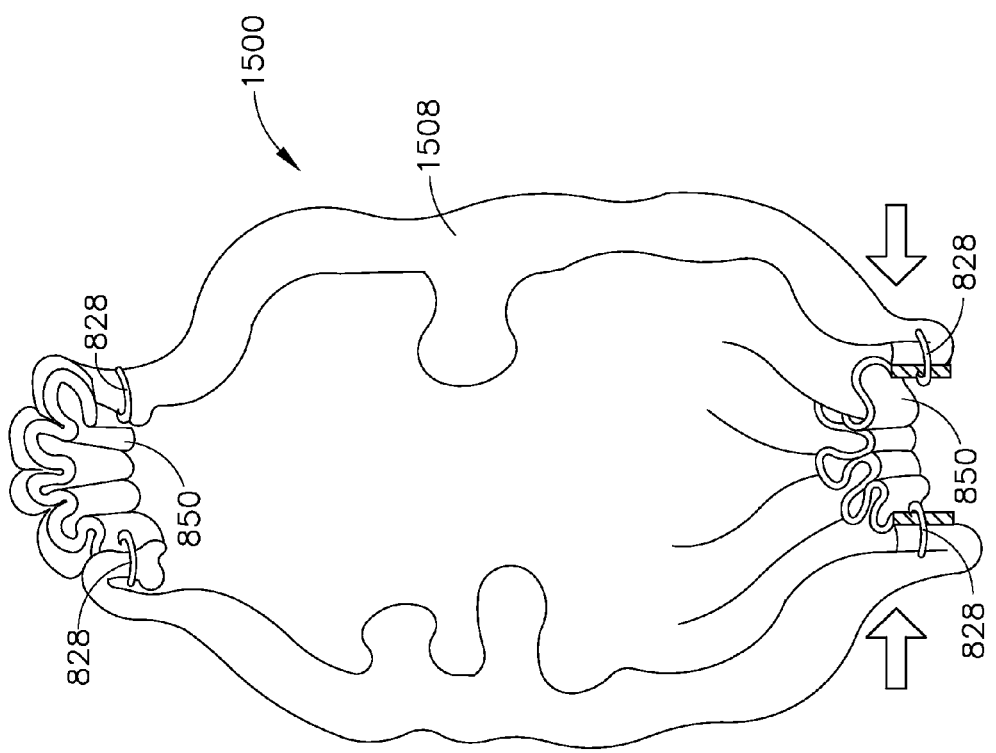
FIG. 26 illustrates a colon portion wherein the elastic rings disclosed in FIGS. 23-25 have been attached to the ends of the colon portion and are in a collapsed state.
Figure 28:
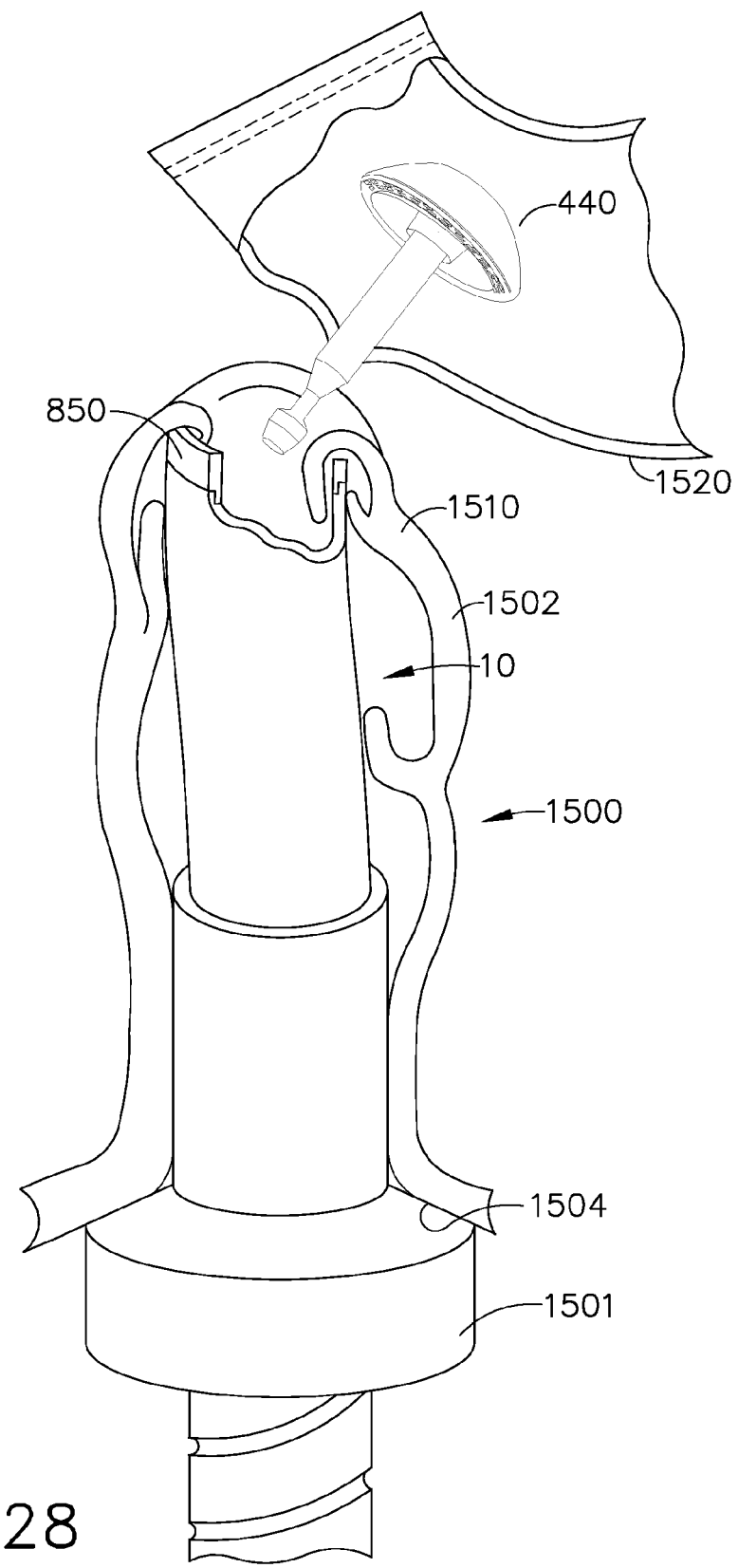
FIG. 28 is a partial perspective view of portions of a patient's colon after the diseased portion has been removed through a port installed in the rectum.

FIG. 26 depicts a diseased specimen 1508 of the colon 1500 after the elastomeric rings 850 have been stapled into each end of the specimen 1508 and the metal rings (if used) have been removed. As can be seen therein, the elastomeric rings 850 serve to bunch up the ends of the diseased specimen 1508 which can reduce the likelihood of depositing diseased cells from inside of the specimen 1508 as it is being removed through the rectum. FIG. 27 illustrates use of a grasper head 900 to pull the diseased colon specimen 1508 through a tube 902 inserted into the rectum. FIG. 28 depicts the colon segments 1502 and 1520 after the specimen or diseased portion 1508 of the colon has been removed. As can be seen in that Figure, a conventional anvil 440 has been inserted through a distal portion 1520 of the colon 1500. The surgical instrument 10 with a horizontal stapling head of the type described above has been inserted through a port 1501 installed into the patient's anus 1504.

Various embodiments of the modular surgical instrument 10 may be used in connection with other forms of surgical tool heads that may be employed to uniformly grip and acquire portions of the colon which facilitates better visualization of the portion of the colon to be transected. Such devices may also be used to ensure that the transection is made substantially perpendicular to the colon. In one embodiment, the surgical tool head 1000 comprises an expandable universal port 1010. See FIGS. 29-32. The universal port 1010 includes an outer shaft portion 1012 that has an attachment stem 1014 that is configured to be attached to the distal end 76 of the outer shaft casing 70 of a modular surgical instrument 10 of the various types and constructions described above. See FIG. 29. However, in other embodiments, the outer shaft portion 1012 may comprise a portion of a dedicated installation tool. In one embodiment, a rotary drive shaft extension 1020 is non-rotatably attached to the distal end portion 180 of the rotary drive shaft 150 in the various manners described above. The rotary drive shaft extension 1020 has a rotary drive gear 1022 attached to its distal end. In this embodiment, only a small amount of rotation may be required to actuate the first and second ring stages of the universal port 1010. Thus, the attachment stem portion 1014 may be sized relative to the flange 182 on the rotary drive shaft 150 such that the pinion gear 156 and gear rack 118 may be brought into meshing alignment and remain in meshing alignment as the rotary drive shaft 150 is axially moved in the distal direction. Such axial movement brings the rotary drive gear 1022 of the rotary drive shaft extension 1020 into meshing engagement with each of the three ring stages of the universal port 1010 as will be described in further detail below.

Figure 29:
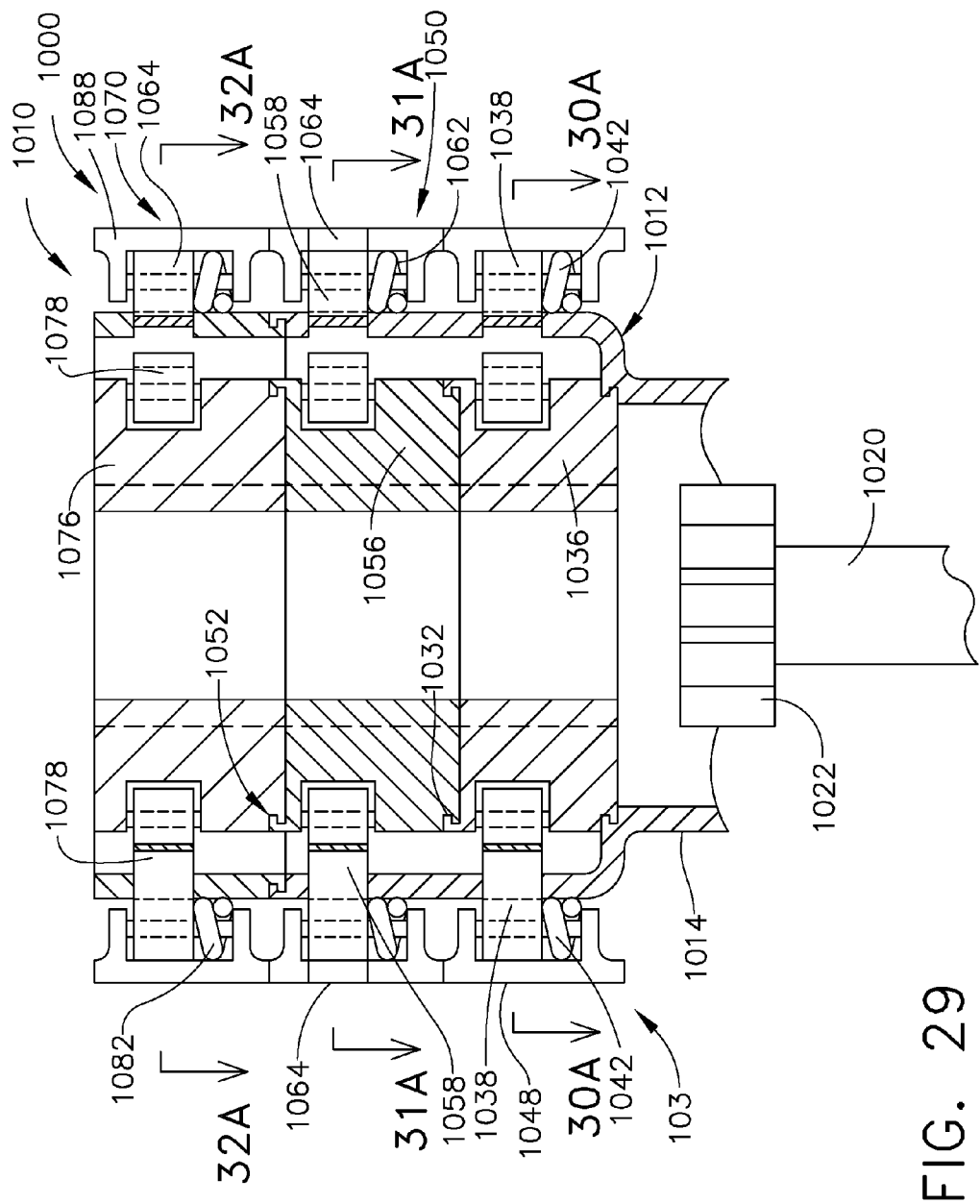
FIG. 29 is a partial cross-sectional view of a universal port member embodiment of the present invention.
Figure 30A:
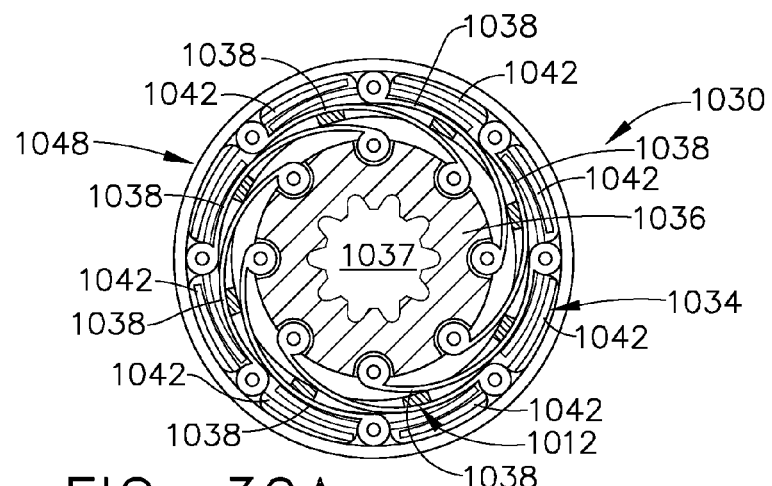
FIG. 30A is a top cross-sectional view of a first ring stage of the universal port member of FIG. 29 taken along line 30A-30A in FIG. 29.
Figure 30B:
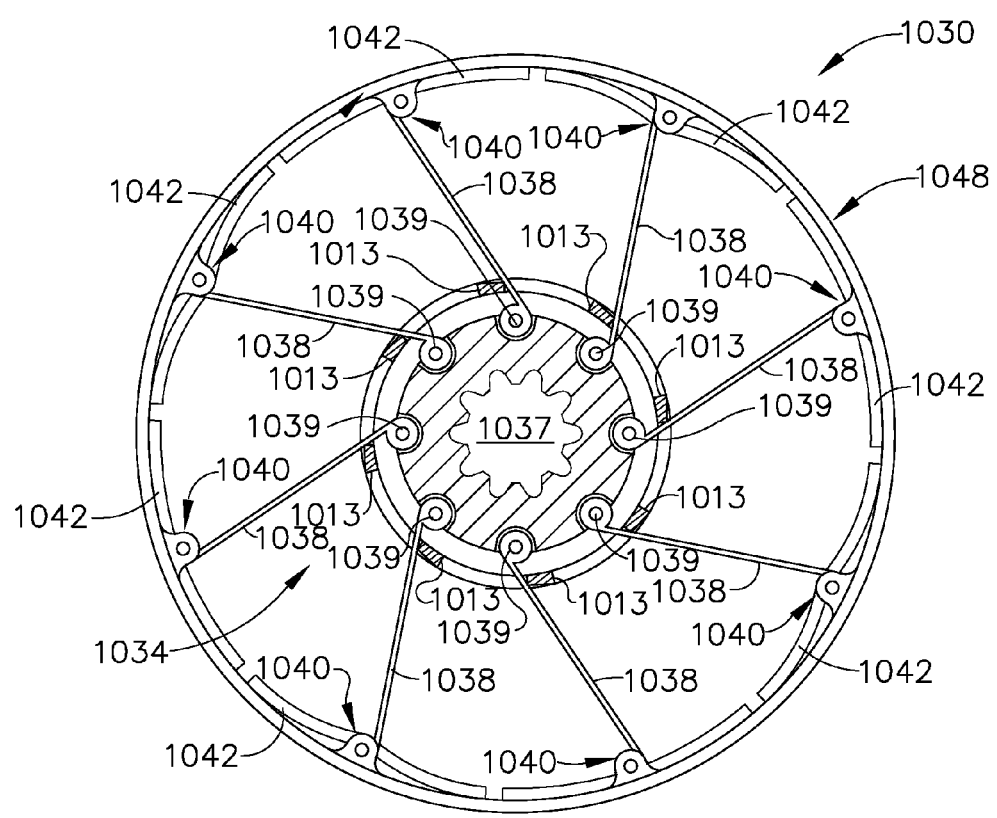
FIG. 30B is another top cross-sectional view of the first ring stage of FIG. 30A in an expanded orientation.

As can be seen in FIG. 29, the universal port 1010 has a first ring stage 1030 that is coupled to a second ring stage 1050 with an attachment feature 1032 that permits relative rotation between the first ring stage 1030 and the second ring stage 1050. The universal port 1010 further has a third ring stage 1070 that is coupled to the second ring stage 1059 by an attachment feature 1052 that permits relative rotation of those components. In at least one embodiment, the first ring stage 1030 is intended to expand the colon. In the depicted embodiment, the first ring stage 1030 includes an expandable first hub assembly 1034 that has an elastomeric outer ring 1048 supported thereon. As can be seen in FIGS. 30A and 30B, the first hub assembly 1034 includes a first central gear hub 1036 that has central gear-receiving aperture 1037 therein that is configured to receive the drive gear 1022 therein. Attached to the first central gear hub 1036 are a plurality of radially extending first spring arms 1038. Each spring arm 1038 has an inner end 1039 that is pivotally pinned to the first central gear hub 1036 and extends through a corresponding opening 1013 in the outer shaft portion 1012. See FIG. 30B. As can be further seen in FIG. 30B, each spring arm 1038 has an outer end 1040 that has a spring member 1042 pivotally pinned thereto. FIG. 30A illustrates the first hub assembly 1034 in a collapsed orientation. Upon application of a rotary motion thereto, the hub assembly 1034 opens to the deployed or expanded orientation depicted in FIG. 30B.

Figure 31A:
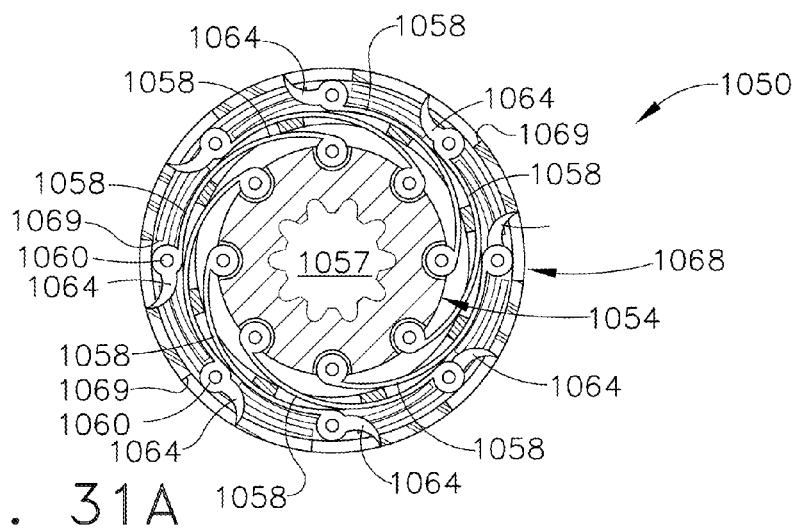
FIG. 31A is a top cross-sectional view of a second ring stage of the universal port member of FIG. 29 taken along line 31A-31A in FIG. 29.
Figure 31B:
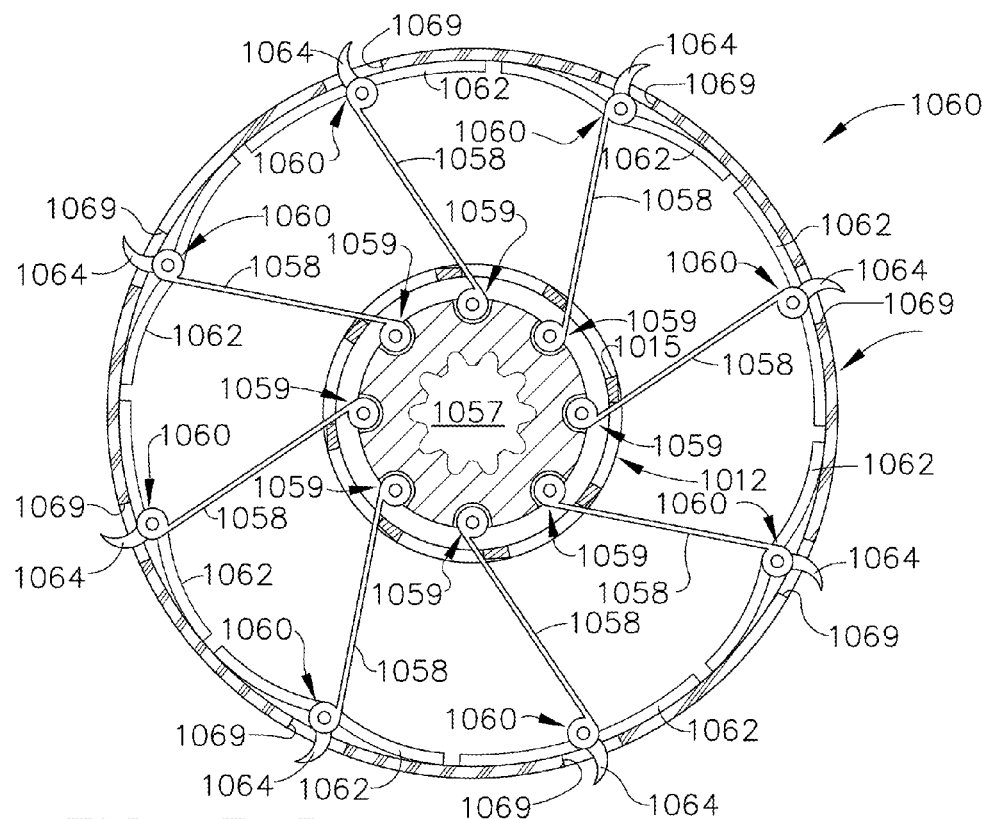
FIG. 31B is another top cross-sectional view of the second ring stage of FIG. 31A in an expanded orientation.

As indicated above, the second ring stage 1050 is attached to the first ring stage 1030 by attachment feature 1032 that permits rotation of the second ring stage 1050 relative to the first ring stage 1030. In the depicted embodiment, the second ring stage 1050 includes an expandable second hub assembly 1054 that has a second elastomeric outer ring 1068 supported thereon. As can be seen in FIGS. 31A and 31B, the second hub assembly 1054 includes a second central gear hub 1056 that has central gear-receiving aperture 1057 therein that is configured to receive the drive gear 1022 therein. Attached to the second central gear hub 1056 is a plurality of radially extending second spring arms 1058. Each second spring arm 1058 has an inner end 1059 that is pivotally pinned to the second central gear hub 1056 and extends through a corresponding opening 1015 in the outer shaft portion 1012. See FIG. 31B. As can be further seen in FIG. 31B, each spring arm 1058 has an outer end 1060 that has a spring member 1062 pivotally pinned thereto. In addition, each spring arm 1058 has a tissue gripping barb 1064 attached thereto that, when deployed, extend through openings 1069 in the second elastomeric outer ring 1068. FIG. 31A illustrates the second hub assembly 1054 in a collapsed orientation. Upon application of a rotary motion thereto, the second hub assembly 1054 opens to the deployed or expanded orientation depicted in FIG. 31B. As the spring arms 1058 move to the expanded orientation, the barbs 1064 are caused to rotate outward.

Figure 32A:
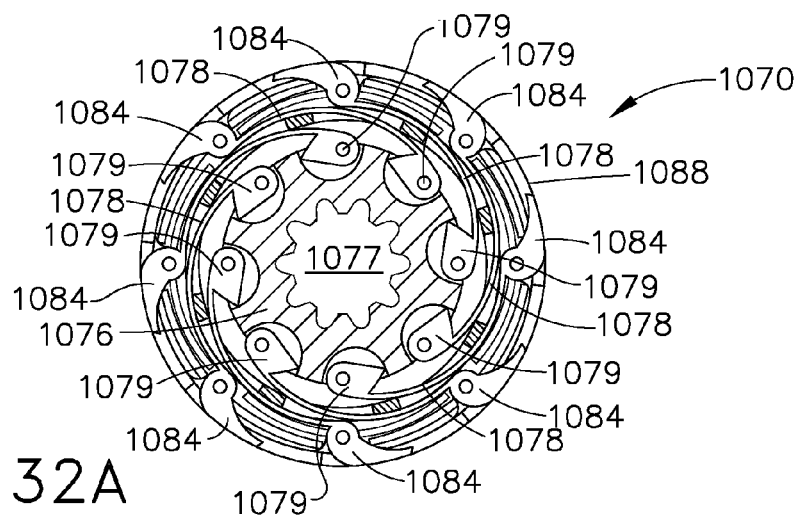
FIG. 32A is a top cross-sectional view of a third ring stage of the universal port member of FIG. 29 taken along line 32A-32A in FIG. 29.
Figure 32B:
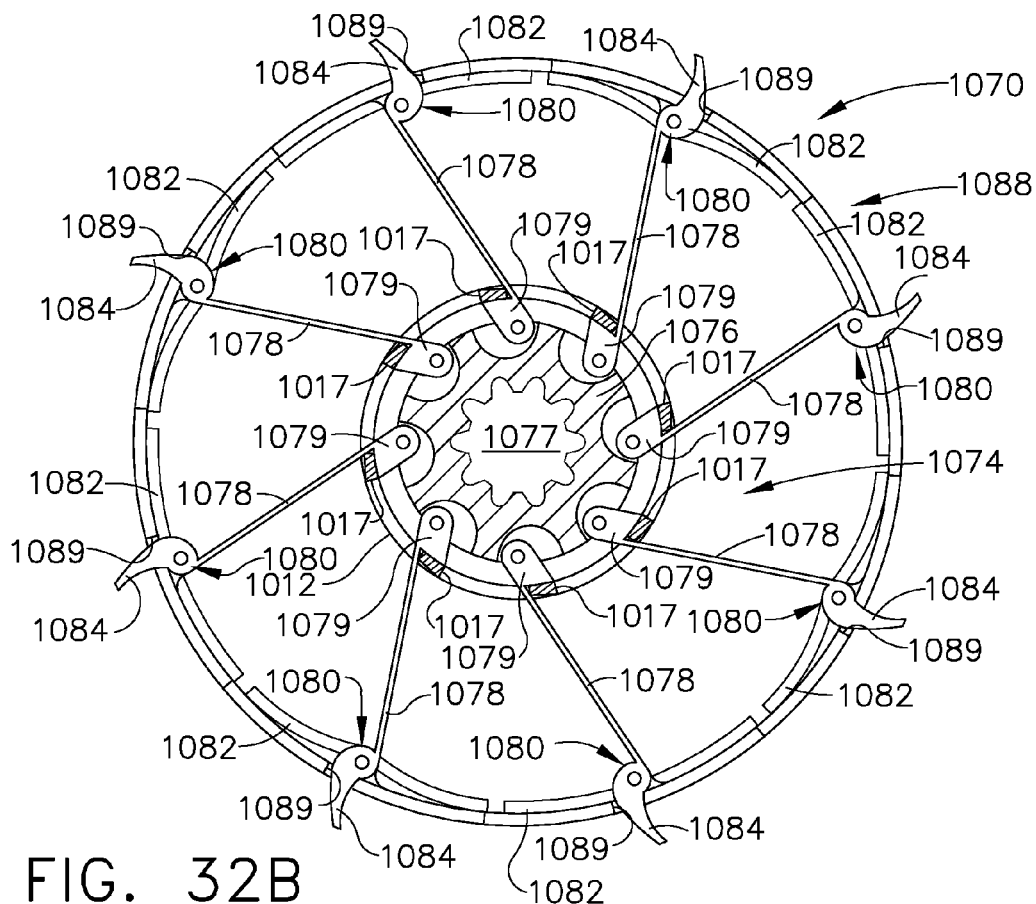
FIG. 32B is another top cross-sectional view of the third ring stage of FIG. 32A in an expanded orientation.

As indicated above, the third ring stage 1070 is attached to the second ring stage 1050 by attachment feature 1052 that permits rotation of the third ring stage 1070 relative to the second ring stage 1050. In the depicted embodiment, the third ring stage 1070 includes an expandable third hub assembly 1074 that has a third elastomeric outer ring 1088 supported thereon. As can be seen in FIGS. 32A and 32B, the third hub assembly 1074 includes a third central gear hub 1076 that has central gear-receiving aperture 1077 therein that is configured to receive the drive gear 1022 therein. Attached to the third central gear hub 1076 is a plurality of radially extending third spring arms 1078. Each third spring arm 1078 has an inner end 1079 that is pivotally pinned to the second central gear hub 1076 and extends through a corresponding opening 1017 in the outer shaft portion 1012. See FIG. 32B. As can be further seen in FIG. 32B, each spring arm 1078 has an outer end 1080 that has a spring member 1082 pivotally pinned thereto. In addition, each spring arm 1078 has a tissue cutting blade 1084 attached thereto that, when deployed, extend through openings 1089 in the third elastomeric outer ring 1088. FIG. 32A illustrates the third hub assembly 1074 in a collapsed orientation. Upon application of a rotary motion thereto, the third hub assembly 1074 opens to the deployed or expanded orientation depicted in FIG. 32B. As the spring arms 1078 move to the expanded orientation, the cutting blades 1084 are caused to rotate outward through the openings 1089. The inner end 1079 of each spring arm 1078 is configured to lockingly engage the shaft 1012 through the corresponding opening 1017 when in the expanded position, such that upon application of a rotary motion thereto (in a counterclockwise direction in FIG. 32B), the spring arms 1078 lock in the extended position and do not collapse when the tissue cutting blades 1084 engage the tissue to be severed.

Operation of the universal port 1010 will now be described. When used in connection with an embodiment of the surgical instrument 10, the surgeon may rotate the control knob 248 to distally advance the distal end 250 of the adjustment shaft 250 to enable the user to install the rotary drive shaft extension 1020 thereon. The rotary drive shaft extension 1020 is configured to removably snap onto or otherwise removably engage the distal end 250 of the adjustment shaft 240. After the rotary drive shaft extension 1020 has been attached, the universal port 1010 is attached to the distal end 76 of the outer shaft casing 70. In particular, the attachment stem 1014 is seated in the outer shaft casing 70 and locked in position using the bayonet-type connection arrangement described above. Prior to inserting the attachment stem 1014 into the distal end 76 of the outer shaft casing 70, the first drive selector switch 130 is moved to disengage the gear plate 110 out of driving engagement with the rotary drive shaft 150 in the manner described above. When the attachment stem 1014 is fully seated within the shaft assembly 60, the rotary drive gear 1022 on the distal end of the rotary drive shaft extension 1020 is brought into meshing engagement with the opening 1037 in the first hub portion 1036. Once the universal port 1010 has been attached to the shaft assembly 60, the first drive selector switch 130 is actuated to bring the gear rack 118 into meshing engagement with the pinion gear 156. The universal port 1010 may then be introduced into the rectum portion 1502 of the colon 1500 through the patient's anus 1504 to the desired deployment position.

Once the universal port 1010 has been positioned in the desired location within the colon 1500, the surgeon may then expand the first ring stage 1030 by squeezing the firing trigger 140. Such action will apply a first rotary motion to the first hub assembly 1034 causing it to move to the expanded orientation shown in FIG. 30B to thereby expand the first outer ring 1048 into expanding contact with the corresponding inner wall portion of the colon 1500. Once the first ring stage 1030 has been expanded, the user may then slide the second axial drive switch 230 to move the rotary drive shaft 150 distally to bring the drive gear into meshing engagement with the second hub portion 1056 of the second ring stage 1050. Such movement of the rotary drive shaft 150 does not disengage the pinion gear 156 from the rack gear 118. Once the drive gear 1022 has meshingly engaged the second hub portion 1056, the surgeon may once again squeeze the firing trigger 140 to impart a second rotary drive motion to the second hub portion 1056. Such action will apply a second rotary motion to the second hub assembly 1056 causing it to move to the expanded orientation shown in FIG. 31B to thereby expand the second outer ring 1068 and deploy the barbs 1064 into retaining engagement with the corresponding portion of the colon 1500 to retain the universal port 1010 in that location. Thereafter, the user may then slide the second axial drive switch 230 to move the rotary drive shaft 150 distally to bring the drive gear 1022 into meshing engagement with the third hub portion 1076 of the third ring stage 1070. Such movement of the rotary drive shaft 150 does not disengage the pinion gear 156 from the rack gear 118. Once the drive gear 1022 has meshingly engaged the third hub portion 1076, the surgeon may once again squeeze the firing trigger 140 to impart a third rotary drive motion to the third hub portion 1076. Such action will apply a third rotary motion to the third hub assembly 1076 causing it to move to the expanded orientation shown in FIG. 32B to thereby expand the third outer ring 1088 and deploy the cutting blades 1064 outwardly through the adjacent colon tissue. As the third ring stage 1070 is rotated, the cutting blades 1064 sever the colon at that location. While the above-described operation of the universal port 1010 employs the use of the modular surgical instrument 10 of various embodiments of the present invention, other embodiments may employ a dedicated tool for actuation of the ring stages of the universal port in the manners described above without departing from the spirit and scope of various embodiments of the present invention.

Figure 33:
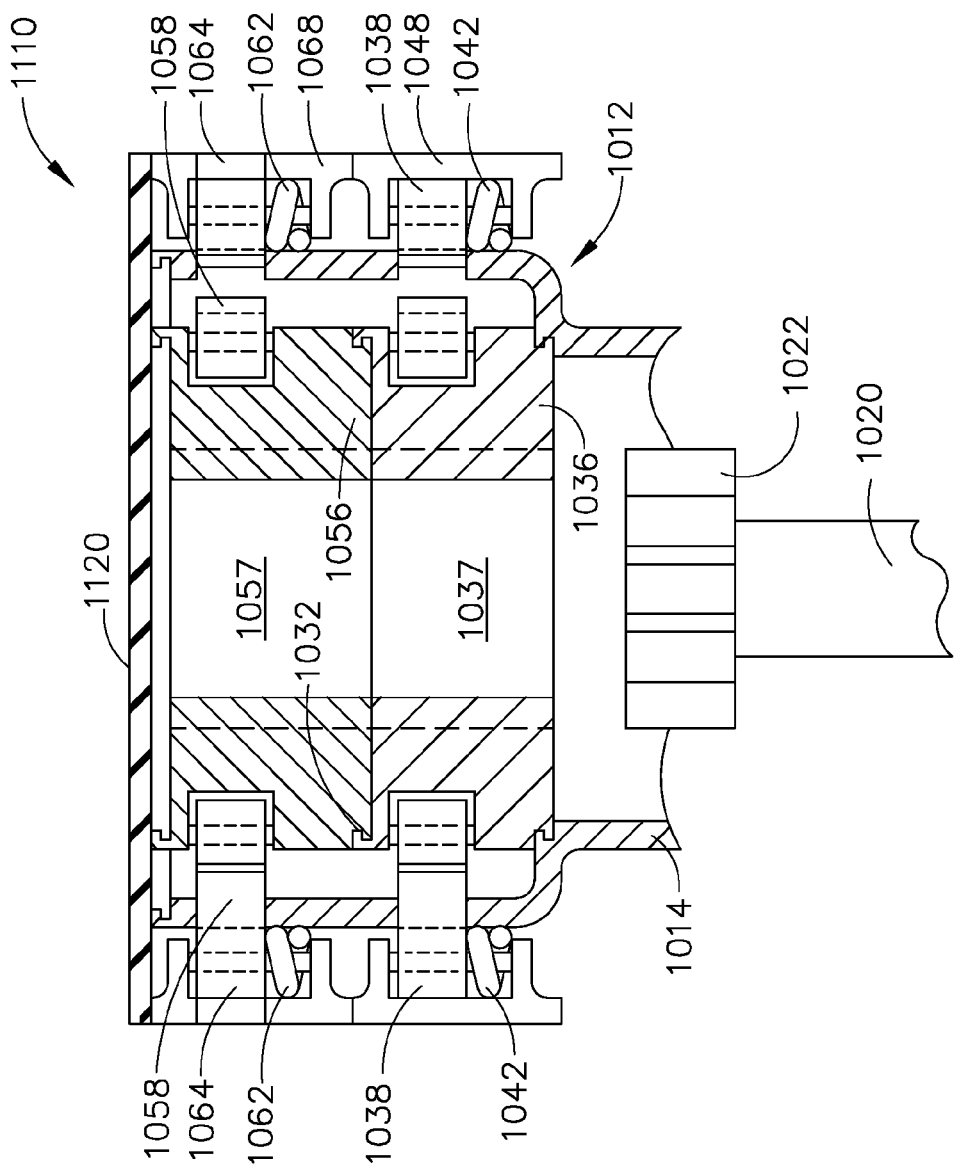
FIG. 33 is a cross-sectional view of another universal port embodiment of the present invention.

FIG. 33 illustrates another universal port embodiment 1110 that only employs two of the ring stages employed by universal port 1010. For example, as shown, the embodiment 1110 illustrates use of the first and second ring stages 1030, 1050 that operate in the same manner described above. However, other embodiments contemplate use of the second and third ring stages 1050, 1070. In either case, the universal port 1110 may be fitted with an occlusion cover to prevent infiltration of tissue into the portion of the colon in which the universal port 1110 has been installed. For example, in one embodiment, the distal-most ring stage (either 1050 or 1070) has a diaphragm assembly 1120 attached thereto. FIG. 33A illustrates a centrally disposed segmented diaphragm assembly 1120. In alternative embodiments, a cover or cap 1121 may be attached to the distal-most ring stage (either 1050 or 1070) as shown in FIG. 33B.

Figure 34:
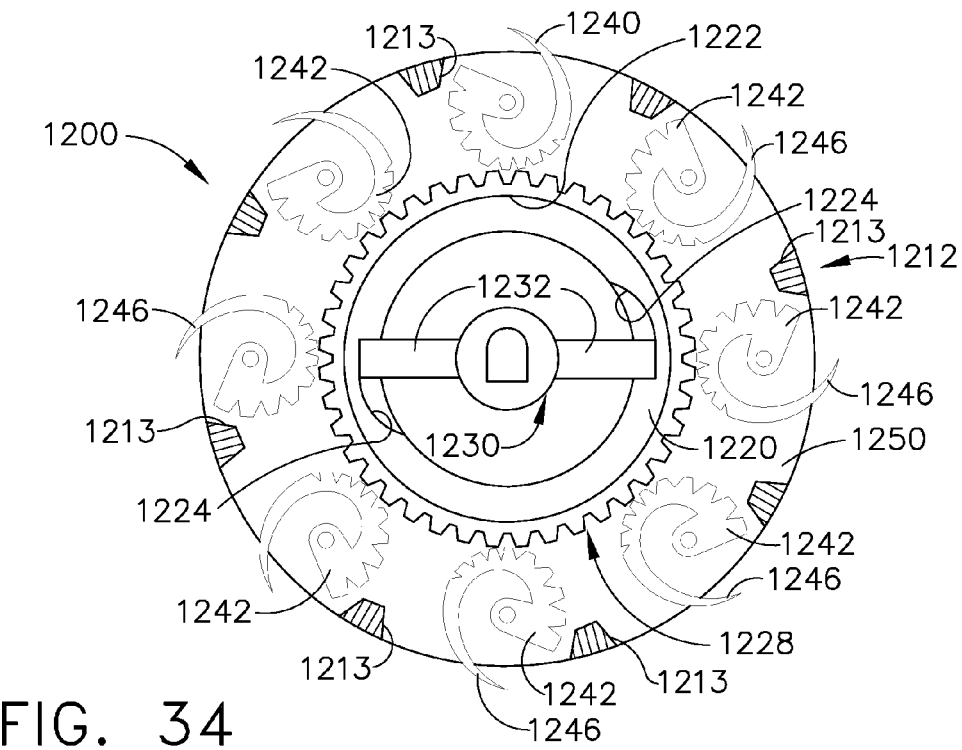
FIG. 34 is a top cross-sectional view of another surgical tool head embodiment of the present invention.
Figure 35:
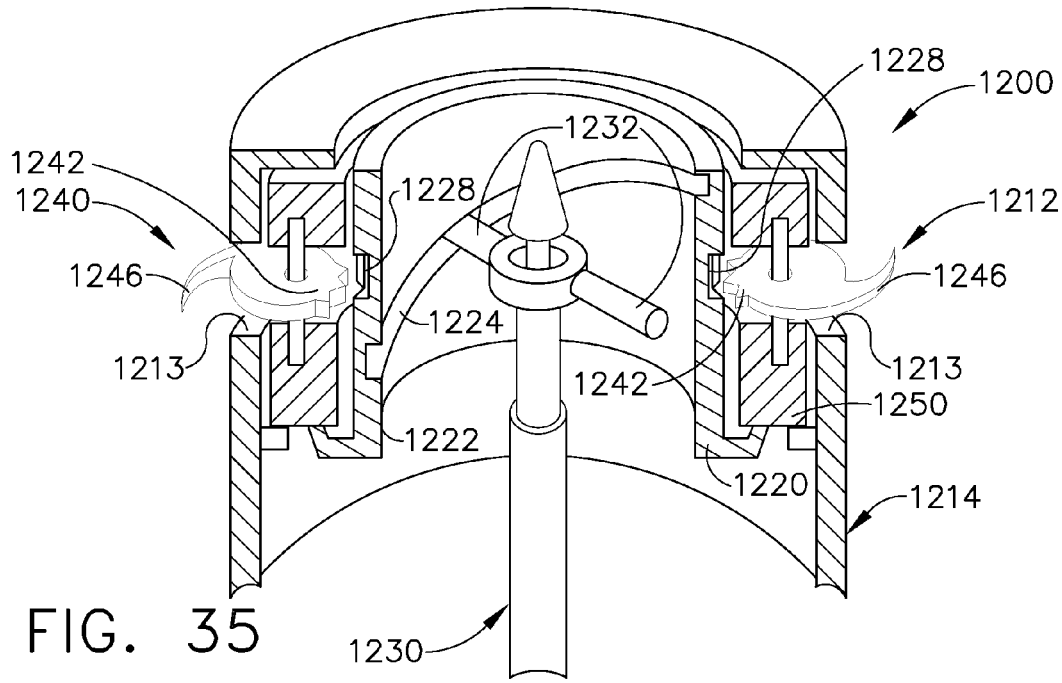
FIG. 35 is a partial cross-sectional elevational view of the surgical tool head embodiment of FIG. 34.

FIGS. 34 and 35 illustrate yet another universal port embodiment 1200 of the present invention that may be used in connection with the surgical instrument 10 or with another dedicated instrument capable of applying axial actuation motions thereto. In the depicted embodiment, the universal port 1200 includes an annular port body or outer casing 1212 that has a stem portion 1214 that is configured for removable attachment to the distal end 76 of the outer shaft casing 70 of an embodiment of the surgical instrument 10 in the above-described manner. A deployment drive assembly in the form of a rotary drive hub 1220 is rotatably supported within the outer casing 1212. As can be seen in FIG. 34, the rotary drive hub 1220 has an inner bore wall 1222 that has a pair of helical slots 1224 therein. The slots 1224 are configured to receive a corresponding actuator pin 1232 that is attached to a drive shaft extension 1230 that is attached to the adjustment shaft 240 employing any of the above-described or similar attachment arrangements. Thus, by distally advancing the drive shaft extension 1230 by rotating the control knob 248, the rotary drive hub 1220 is rotated about the longitudinal axis LA-LA by virtue of the interaction between the actuator pins 1232 and helical slots 1224.

As can be seen in FIGS. 34 and 35, a drive gear 1228 is formed around the outer circumference 1126 of the rotary drive hub 1220. The drive gear 1228 is supported to meshingly engage with a gear portion 1242 on a plurality of tissue barb assemblies 1240 that are each rotatably supported on an annular support ring 1250 as shown. The tissue barb assemblies 1240 have a hook portion 1246 thereon that are adapted to hookingly engage the colon when the universal port 1200 has been deployed therein. Each hook portion 1246 is configured to protrude through a corresponding opening 1213 in the outer casing 1212. Thus, application of the axial drive motion to the adjustment shaft 240 ultimately causes the rotary drive hub 1220 to rotate and deploy the hook portions 1246 into the adjacent colon tissue.

Figure 36:
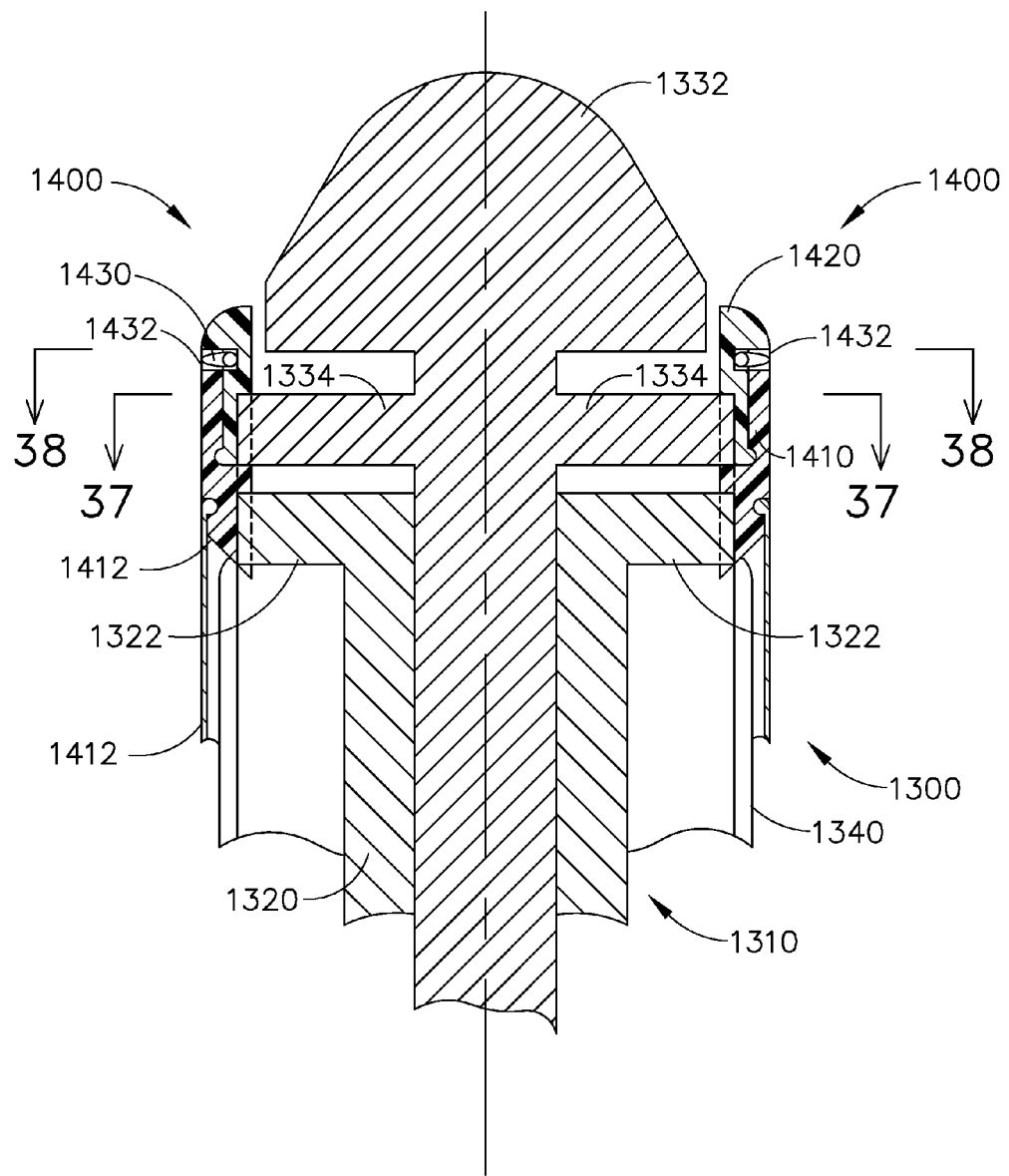
FIG. 36 is a partial cross-sectional view of another universal port embodiment of the present invention in connection with an installation tool.
Figure 37:
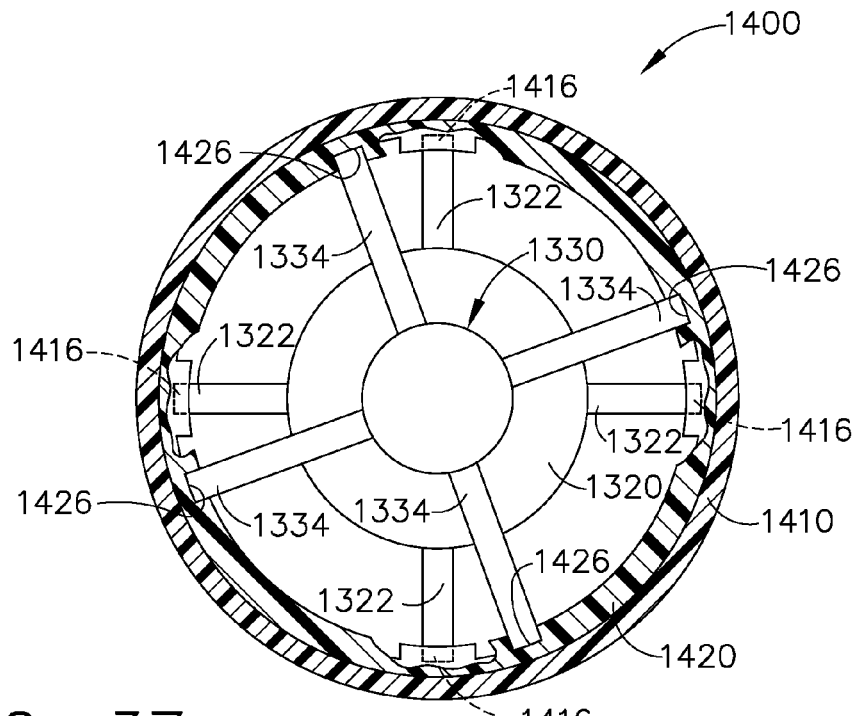
FIG. 37 is a top cross-sectional view of the universal port and installation tool embodiments of FIG. 36 taken along line 37-37 in FIG. 36.
Figure 38:
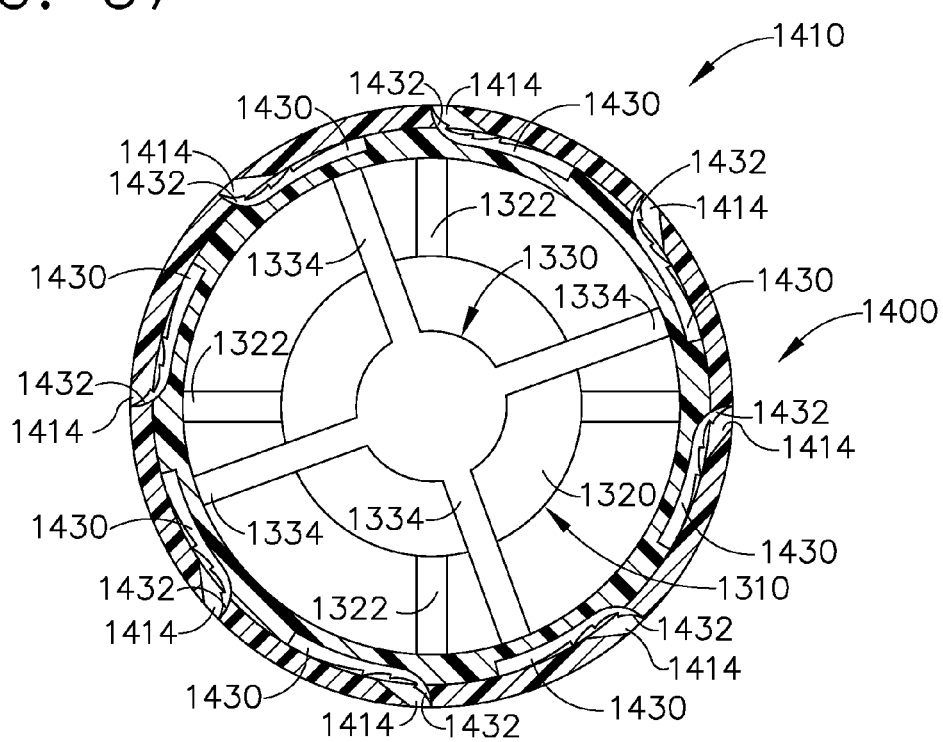
FIG. 38 is a top cross-sectional view of the universal port and installation tool embodiments of FIGS. 36 and 37 taken along line 38-38 in FIG. 36.
Figure 39:
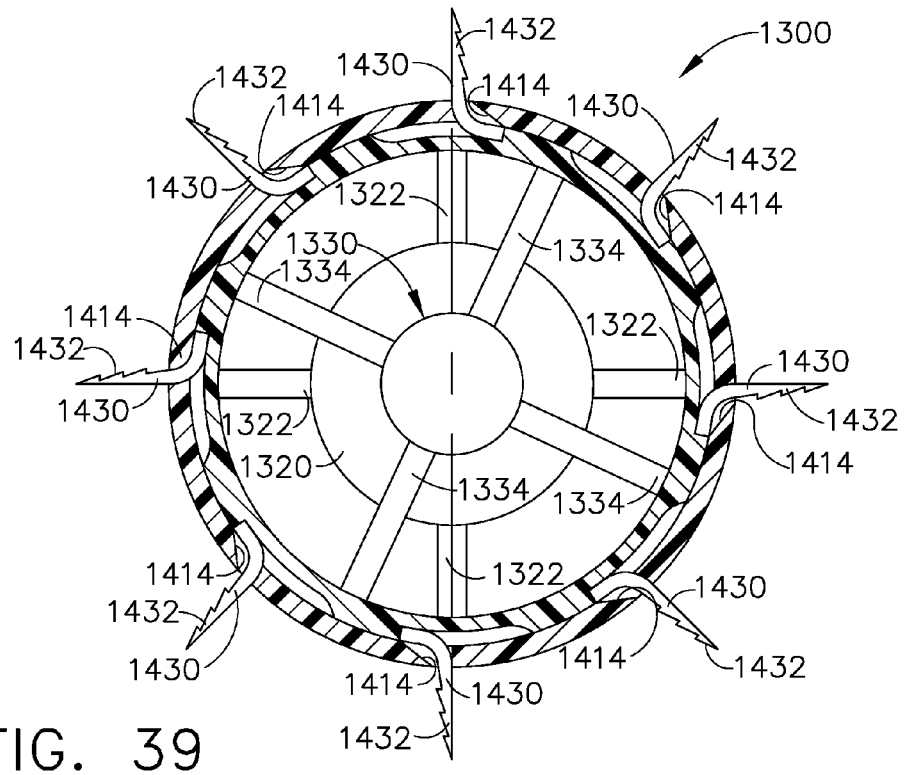
FIG. 39 is a top cross-sectional view of the universal port and installation tool embodiments of FIGS. 36-38 with the tissue retaining barbs in a deployed position.
Figure 40:
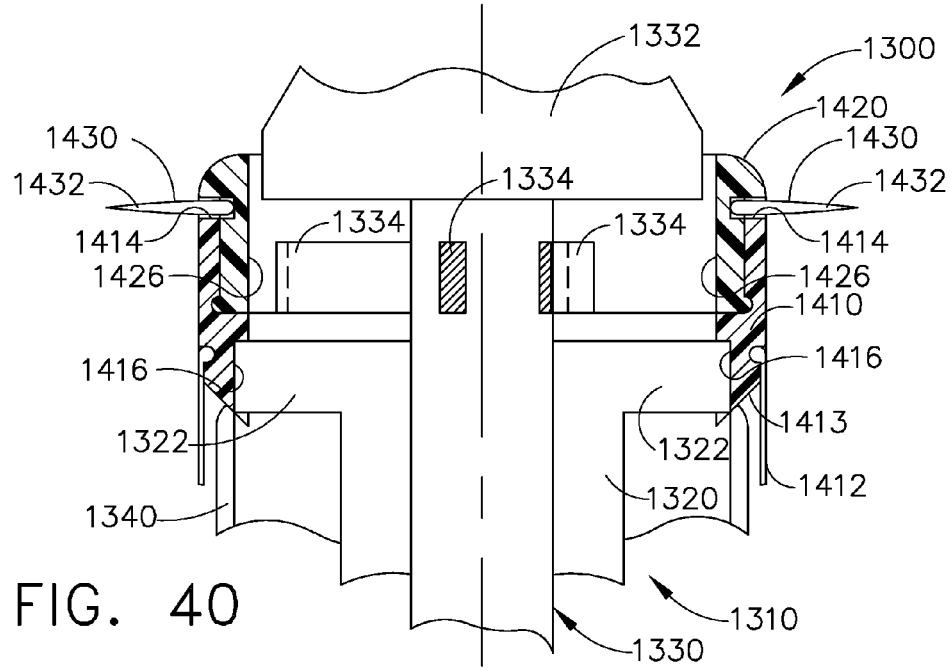
FIG. 40 is a side cross-sectional view of the universal port and installation tool embodiments as depicted in FIG. 39.

FIGS. 36-40 illustrate another universal port embodiment 1400 of the present invention that may be used in connection with an embodiment of the modular surgical instrument 10 or with a dedicated instrument 1310 that has a hollow support shaft 1320 that rotatably supports a rotary drive shaft assembly 1330 therein. Additionally, FIGS. 36 and 40 illustrate use the surgical instrument 1310 with a hollow support or stiffening tube 1340, the purpose of which will be discussed in further detail below. As can be seen in FIGS. 36-40, the hollow support shaft 1320 has a plurality of first support arms 1322 protruding therefrom. The rotary drive shaft assembly 1330 has a substantially blunt distal end 1332 and a plurality of second arms 1334 radially extending therefrom. The drive shaft assembly 1330 is rotatably supported within the support shaft 1320 and is configured to interface with a handle or other source of rotary motion.

In various embodiments, the universal port 1400 has first annular port body in the form of an outer ring portion 1410 and a second annular port body in the form of an inner ring portion 1420. In at least one form, the inner and outer ring portions 1410, 1420 are fabricated from a rigid polymer or other suitable material and are attached together as shown to enable the outer ring 1410 to rotate relative to the inner ring 1420. A flexible sleeve 1412 is attached to the outer circumference of the first ring stage 1410 and extends beyond the proximal end 1413 thereof as shown and preferably is long enough to protrude out of the patient's anus. As will become further apparent as the present Detailed Description proceeds, the sleeve 1412 forms a passageway extending from the universal port 1400 which can make repeated insertions of various surgical instruments into the rectum easier and simpler and may also serve as a wound protector and shield for preventing contact between the extracted specimen and the rectum. Thus, the sleeve 1412 may minimize the likelihood of "seeding" and makes extraction of the diseased specimen easier. In various embodiments, the sleeve 1412 is fabricated from a puncture-resistant weave. In other embodiments, the sleeve has a plastic reducing spiral built therein which could provide the sleeve with "funnel-like" attributes to further the passage of large masses of tissue therethrough.

As can be seen in FIGS. 38 and 39, the inner ring 1420 has a plurality of barbed sutures 1430 spaced equally around its outer circumference. Each tissue barb 1430 has an end portion 1432 that extends into a corresponding slot 1414 in the outer ring portion 1410. The slots 1414 are shaped such that when the universal port 1400 is in the un-deployed or insertion state, the end portion 1432 is substantially completely contained within the slot 1414 and when the inner ring 1420 is rotated relative to the outer ring 1410, the suture barbs 1430 are deployed therefrom as shown in FIGS. 39 and 40.

Figure 41A:
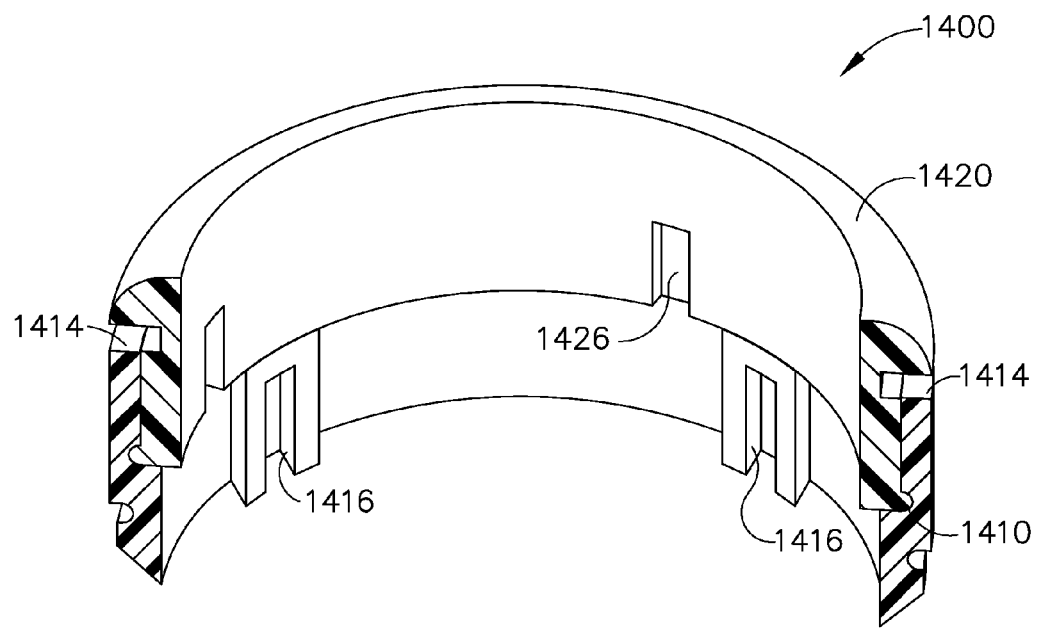
FIG. 41A is a cross-sectional view of the universal port of FIGS. 36-40.
Figure 41B:
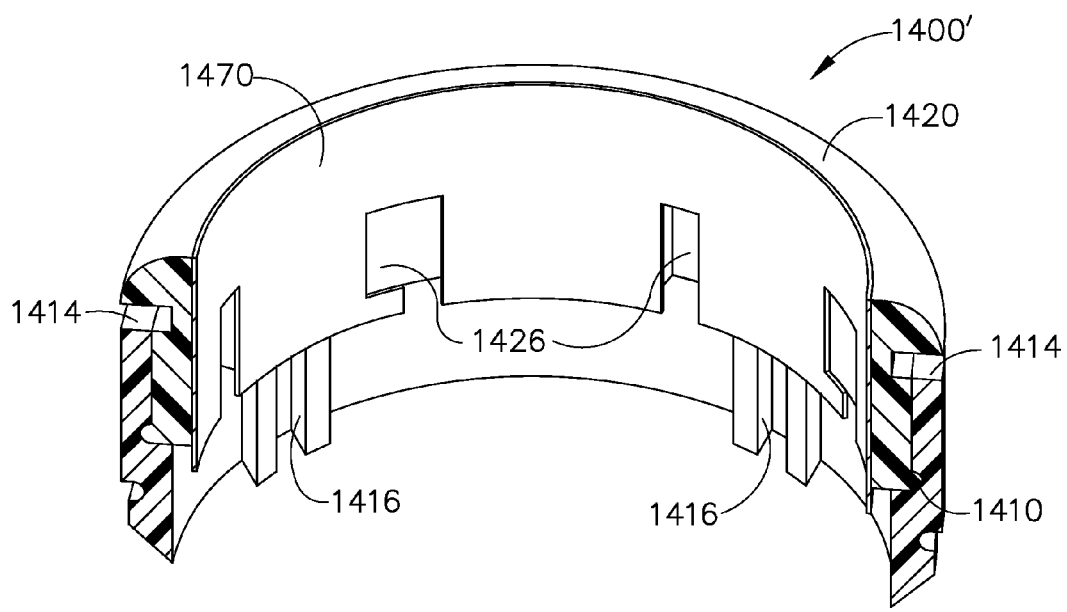
FIG. 41B is a cross-sectional view of a universal port in accordance with at least one alternative embodiment.

As indicated above, the hollow support shaft 1320 has a plurality of first support arms 1322 radially protruding therefrom and the rotary drive shaft assembly 1330 has a plurality of second support arms 1334 protruding therefrom. As can be seen in FIGS. 40 and 41, the ends of the first support arms 1322 are adapted to be received within corresponding closed end slot formations 1416 formed along the inner circumference of the outer ring 1410. Likewise, the ends of the second support arms 1334 are adapted to be received within corresponding closed end slot formations 1426 formed along the inner circumference of the inner ring 1420.

Figure 42:
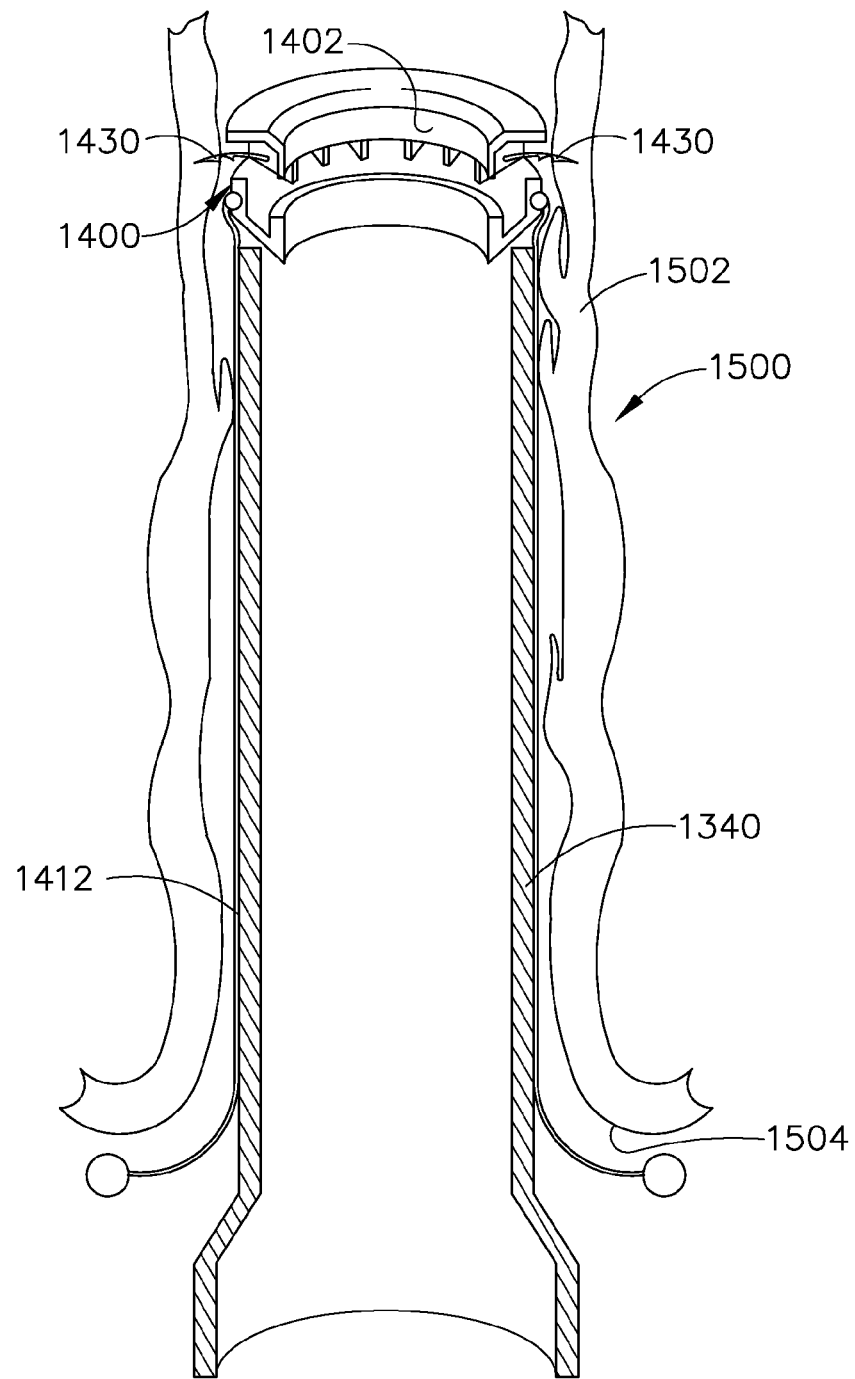
FIG. 42 is a partial cross-sectional view of a universal port embodiment of the present invention and insertion tube embodiment of the present invention positioned within the rectum.
Figure 43:
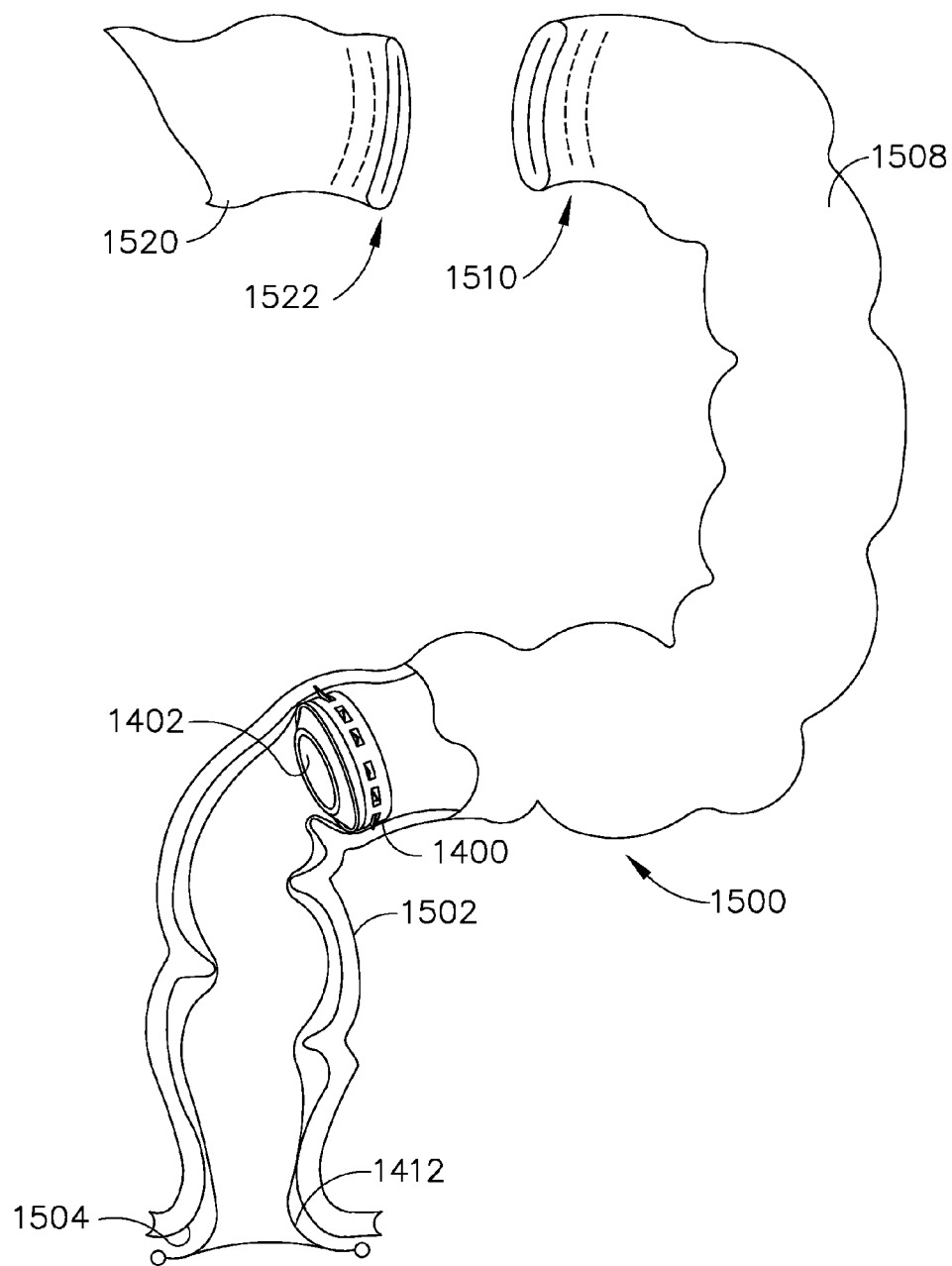
FIG. 43 illustrates a universal port embodiment of the present invention installed in the rectum and wherein a diseased portion of the colon has been severed from a distal portion of the colon.
Figure 44:
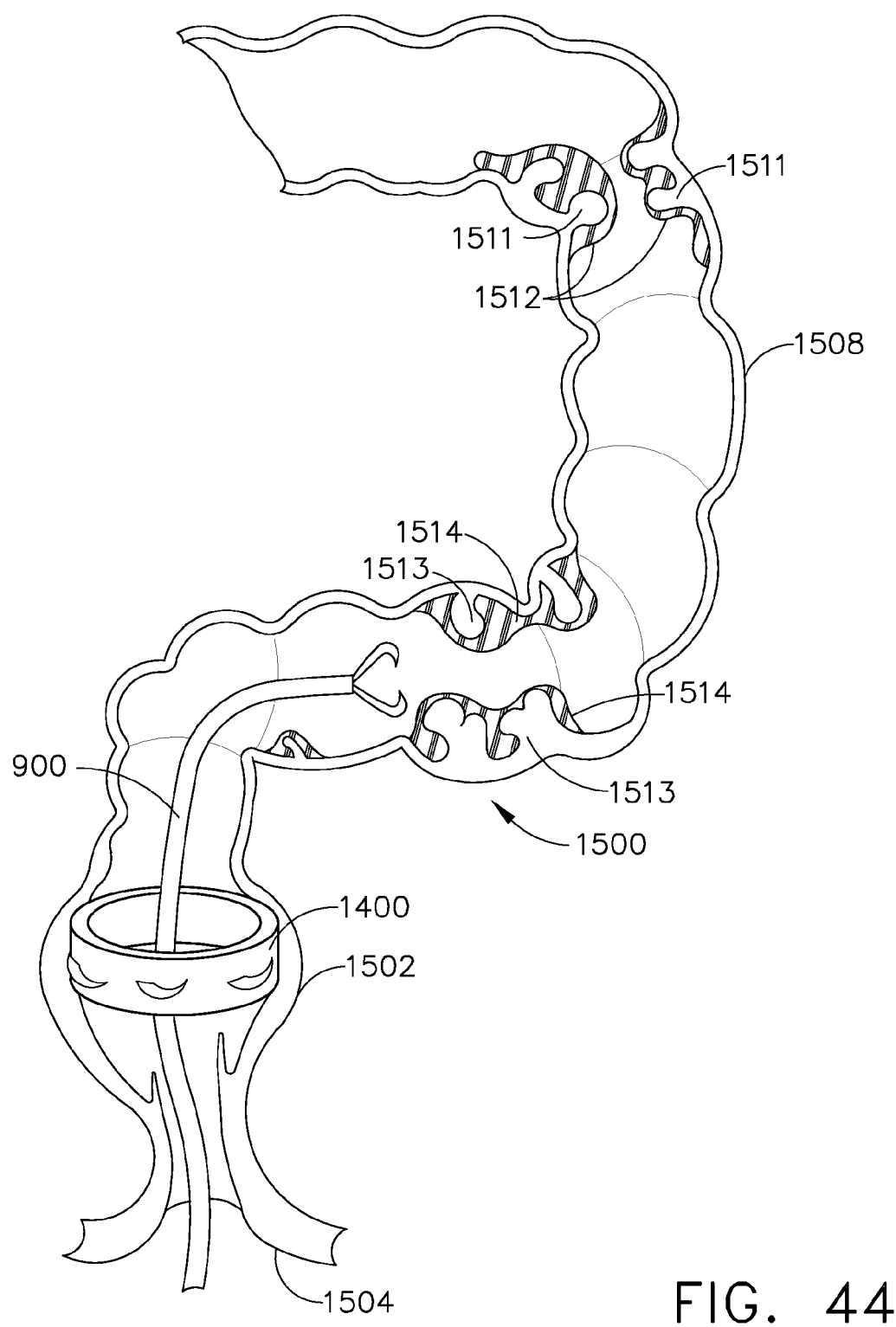
FIG. 44 illustrates use of a grasping instrument through a universal port embodiment of the present invention.

Use of the universal port 1400 will now be explained. Prior to insertion into the colon, the universal port 1400 is installed onto the tool 1310. In at least one embodiment, the support shaft 1320 and rotary drive shaft assembly 1330 are axially advanced into the open center area 1402 in the universal port 1400 such that the first support arms 1322 are seated in corresponding slot formation 1416 in the outer ring 1410 and the second support arms 1334 are seated in corresponding slot formations 1426 in the inner ring 1420. The hollow stiffening tube 1340 may be inserted over the support shaft 1320 to engage the bottom surface of the outer ring 1413. Once the universal port 1400 has been installed onto the tool 1310 and the stiffening tube 1340 installed as shown, the surgeon may then insert the assembly into the rectum portion 1502 of the colon 1500 through the anus 1504 to bring the universal port 1400 into the desired location within the rectum portion 1502. See FIG. 42. Once the surgeon has determined that the universal port 1400 is located in the desired position, a rotary actuation motion is applied to the rotary drive shaft assembly 1330 which rotates the inner ring 1420 relative to the outer ring 1410 and thereby deploys the suture barbs 1430 into the adjacent colon wall to affix the universal port 1400 thereto. Thereafter, the surgeon may then withdraw the surgical tool 1310 out through the stiffening tube 1340 leaving the universal port 1400 and stiffening tube 1340 in position as shown in FIG. 42. As can be seen in FIG. 42, the end of the flexible sleeve 1412 extends around the stiffening tube 1340 and out through the patient's anus 1504. The surgeon may then insert other instruments up through the stiffening tube 1340 (if retained in place) or through the flexible sleeve 1412 (if the stiffening tube 1340 has been removed) and through the opening 1402 in the universal port 1400 to gain access to the colon portions beyond. FIGS. 43 and 44 illustrate the universal port 1400 installed in the rectum 1502 after the stiffening tube 1340 has been removed. In FIG. 43, the diseased colon portion 1506 has been cut from the distal colon portion 1520. Both the end 1510 of the diseased portion 1508 and the end 1522 of the distal colon portion 1520 have been stapled shut. Those processes may be performed using the various surgical tools, stapling heads and anvil arrangements of various embodiments of the present invention or they could have been performed using a separate endocutter (not shown) that was inserted through additional ports or openings provided through the abdominal wall.

Figure 45:
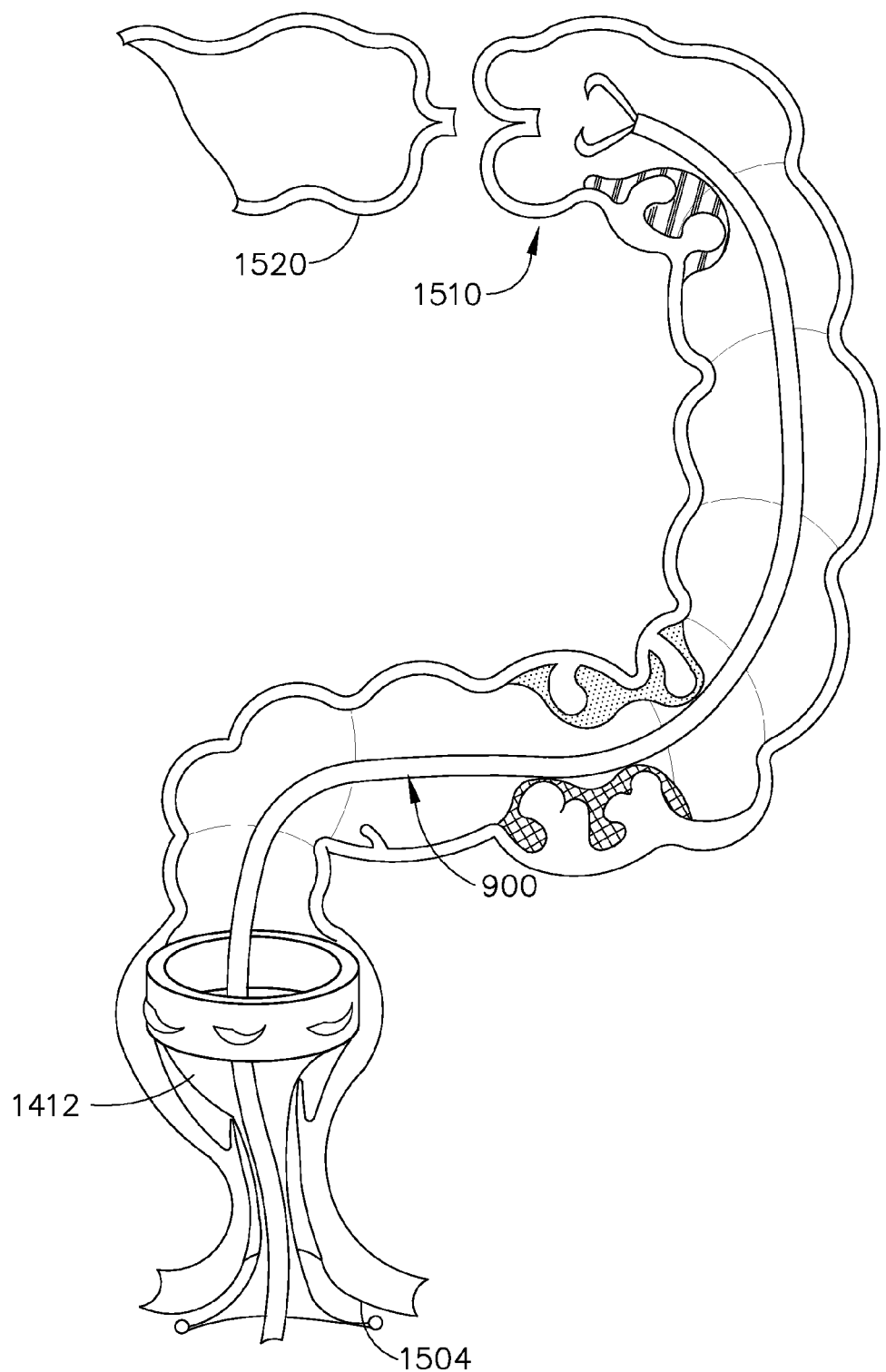
FIG. 45 is another view of the universal port and grasping instrument depicted in FIG. 44.
Figures 46, 47:
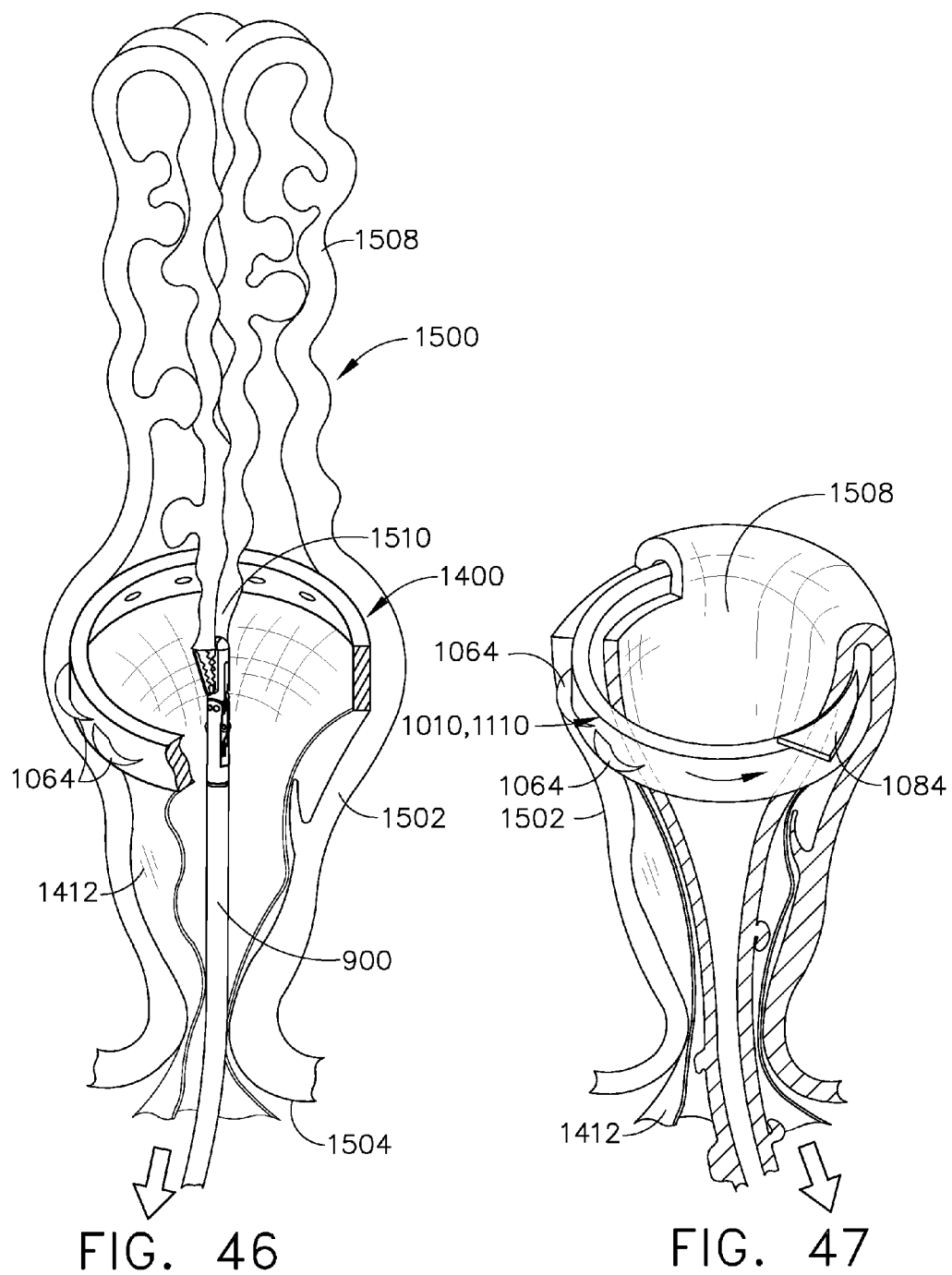
FIG. 46 is another view of the universal port of FIGS. 44 and 45 wherein the grasping instrument is being used to draw the diseased colon portion through the universal port.
FIG. 47 illustrates use of another universal port embodiment of the present invention within a colon wherein a diseased portion has been drawn therein and the tissue cutting members of the port have been deployed to sever the diseased portion from the rectum.
Figure 48:
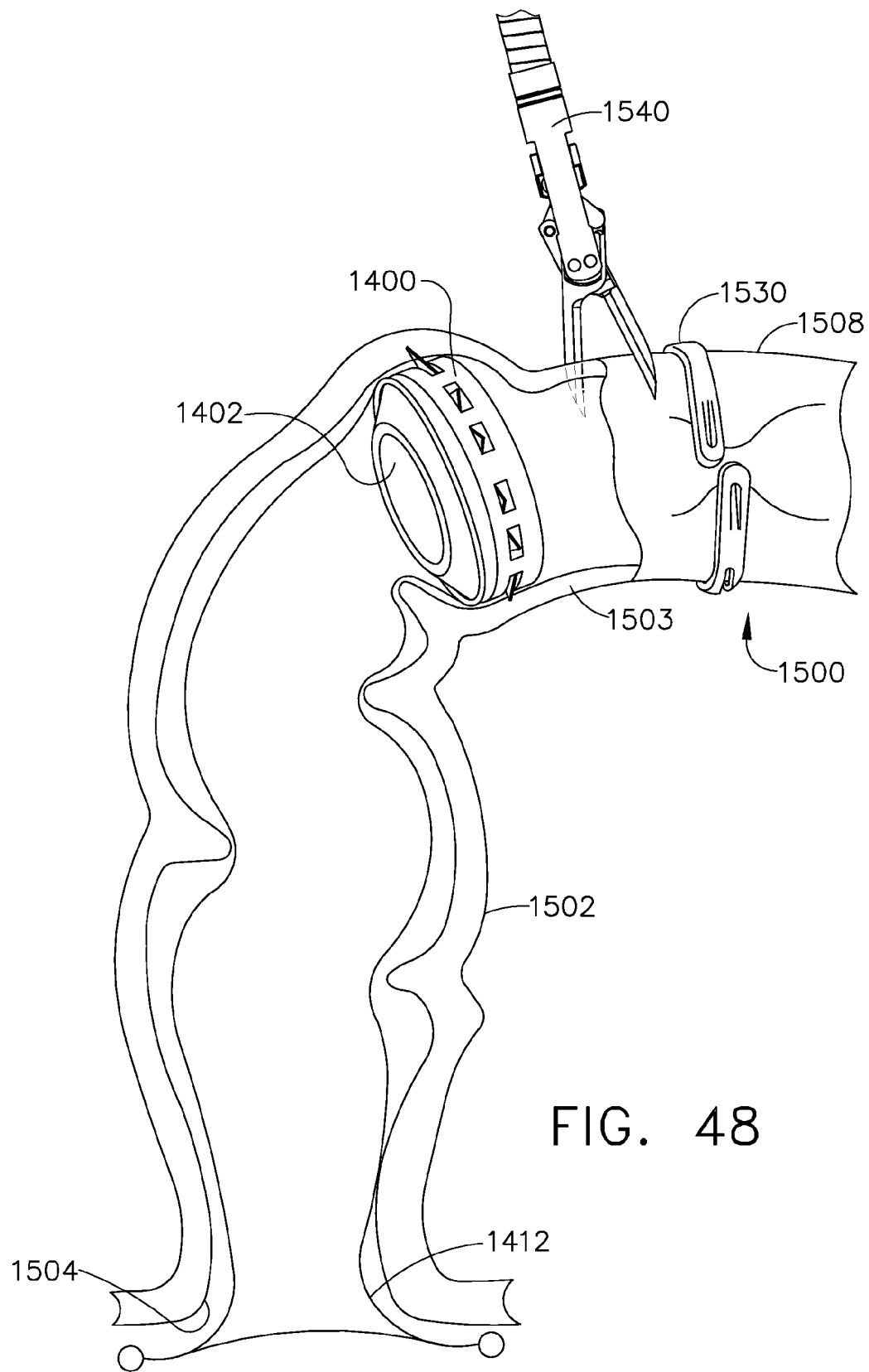
FIG. 48 is another view of a portion of a colon with a universal port embodiment of the present invention installed therein.

FIG. 44 illustrates use of a grasping instrument 900 in connection with the universal port 1400 that has been attached within the rectum 1502 of the colon 1500. In this Figure, the diseased portion 1508 of the colon 1500 has been cut from the distal portion and wax or other suitable material 1512 has been injected over some of the lesions 1511 and a web like covering material 1514 has been placed over other lesions 1513 to prevent seeding. FIG. 45 illustrates use of the grasping device to grab the end 1510 of the diseased portion 1508 to pull it back through the universal port 1400 as shown in FIG. 46. Thereafter, the diseased portion 1508 may be severed from the rectum 1502 by a conventional tissue cutting instrument that is inserted through another port or opening in the abdominal wall. FIG. 47 illustrates, in somewhat diagrammatic format, a similar arrangement wherein a universal port 1010 or 1110 has been used and the diseased portion 1508 has been pulled down therethrough. In that instance, the surgeon reattaches the surgical instrument 10 or installation tool to the universal port to activate the tissue cutting members 1084 thereof to sever the diseased portion 1508 from the rectum.

Figure 49:
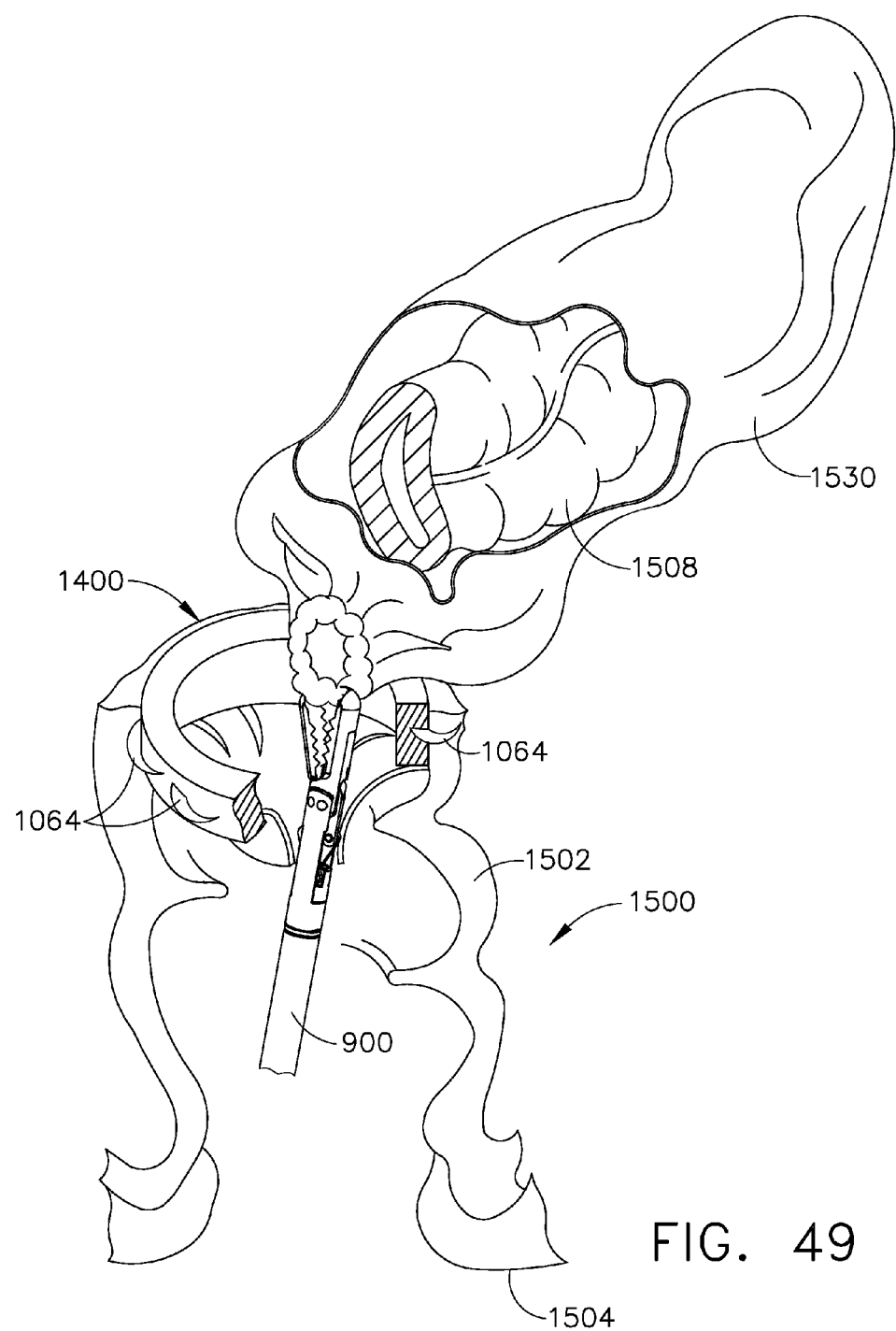
FIG. 49 is another view of the colon and universal port of FIG. 47 wherein a severed diseased portion has been inserted into a collection bag that is being drawn through the port with a grasping instrument.

In FIG. 44, a conventional metal clamp 1530 has been installed between the rectum portion 1502 and the diseased portion 1508. In the depicted embodiment, the surgeon is using a cutting instrument 1540 to cut the portion 1503 of the colon 1500 located between the universal port 1400 and the clamp 1530. Once the diseased portion 1508 has been separated from the rectum portion 1502, the surgeon may withdraw the severed diseased portion 1508 through the hole 1402 in the universal port 1400. The sleeve 1412 prevents the diseased portion 1508 from contaminating the rectum portion 1502 as it is removed through the anus 1504. Once the diseased portion 1508 of the colon 1500 has been removed, the surgical tools and tool heads disclosed herein may be inserted through the anus 1504 to re-attach the colon portion 1520 to the rectum 1502. In FIG. 49, the diseased portion 1508 has been placed into a pouch 1530 that was inserted through the universal port 1400.

Figure 50:
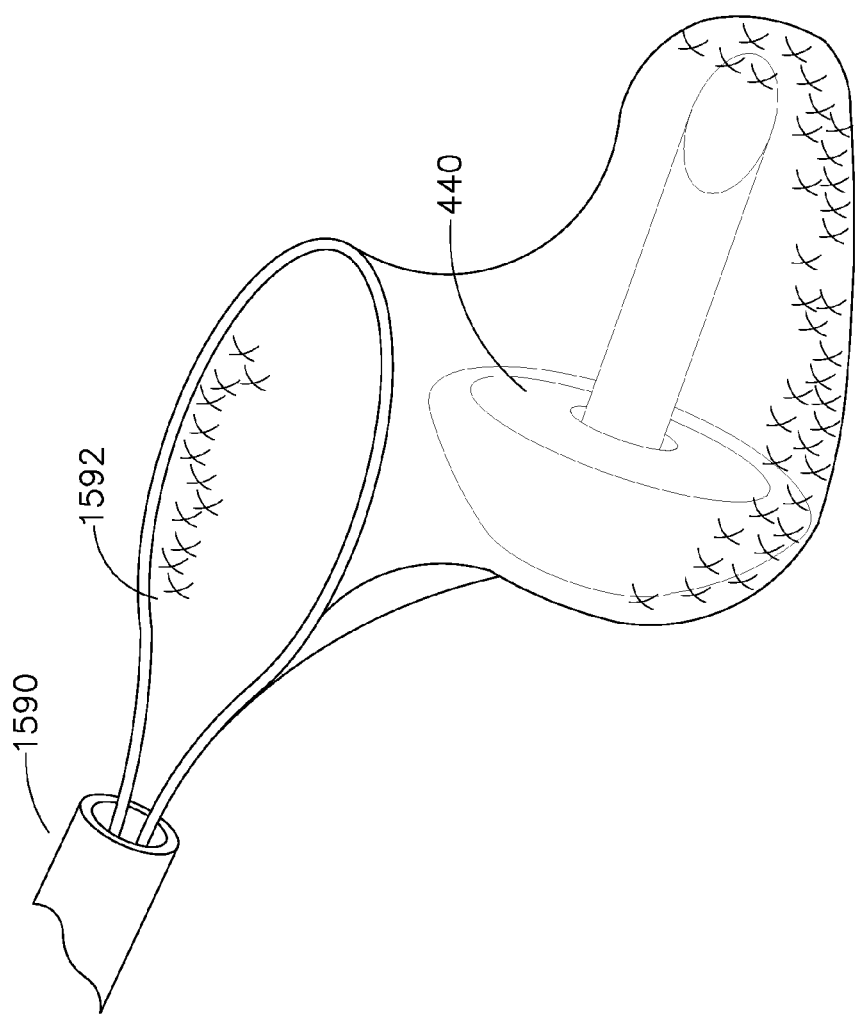
FIG. 50 is a partial perspective view of a retrieval instrument used to retrieve an anvil from the surgical site.

FIG. 50 illustrates one method of removing an anvil 440 from the surgical site after use. In this method, a retrieval instrument 1590 that has a deployable pouch portion 1592 is inserted through another opening or port provided through the abdominal wall. However, those or ordinary skill in the art will appreciate that the surgeon may introduce and remove an anvil 440 through the universal port 1400. In particular, it will be further appreciated that the various collapsible anvil arrangements disclosed in the previously incorporated patent applications are well-suited for this purpose.

Figure 51:
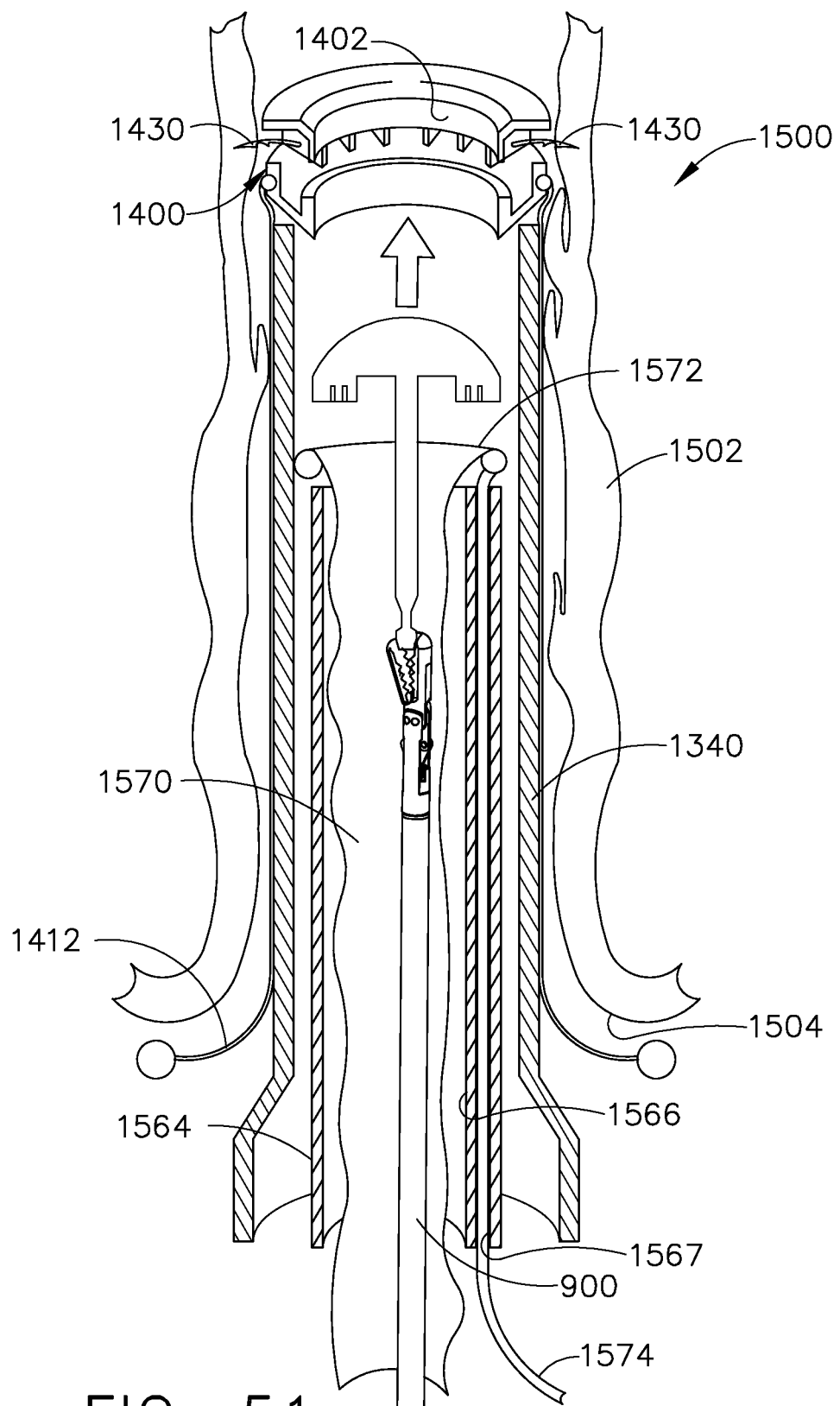
FIG. 51 is a partial cross-sectional view of a universal port embodiment of the present invention and insertion tube embodiment of the present invention positioned within the rectum with a retrieval tool embodiment of the present invention inserted therein to introduce an anvil into the surgical site.
Figure 52:
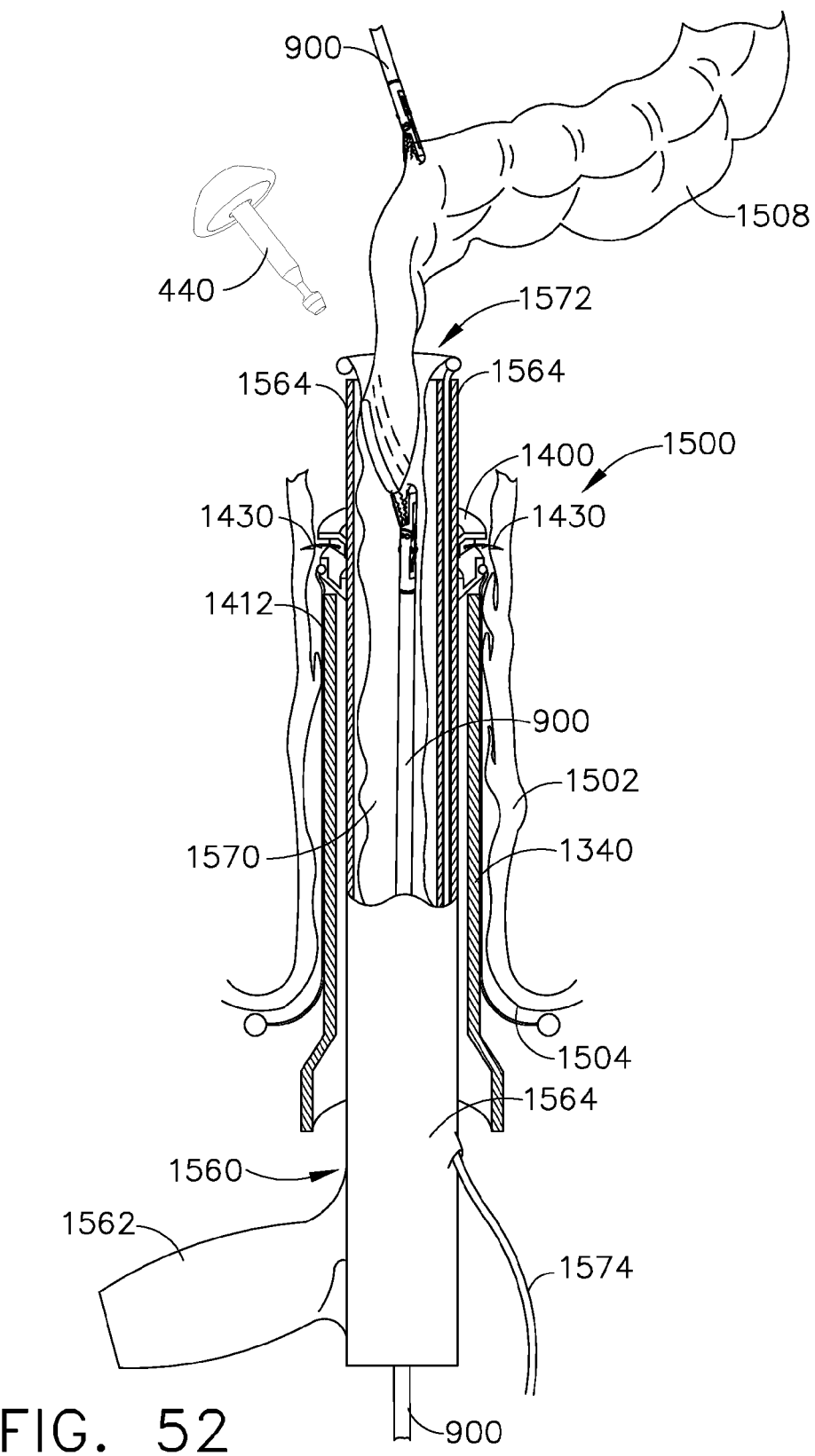
FIG. 52 is another view of the universal port, insertion tube and retrieval tool as depicted in FIG. 51 and wherein a diseased portion of the colon is being drawn into the retrieval tool by a grasping instrument inserted therethrough.

Turning to FIGS. 51 and 52, the universal port 1400 and the stiffening tube 1340 are particularly well-suited for use with a retrieval tool embodiment 1560 of the present invention. In various forms, the retrieval tool 1560 comprises a handle portion 1562 that has a hollow retrieval tube 1564 protruding therefrom that defines a conduit passage 1566 extending through the tool to facilitate the passage of tools therethrough. FIGS. 51 and 52 illustrate the passage of a grasping instrument 900 therethrough. Various embodiments further include a flexible sleeve 1570 that has a cinchable distal opening 1572 that is positioned on the distal end 1565 of the retrieval tube 1564. A cinch cord 1574 is attached to around the cinchable opening and extends through a passage 1567 in the retrieval tube 1564 as shown in FIG. 51. FIG. 51 also illustrates use of the retrieval tool 1560 and universal port 1400 for introducing an anvil 440 into the surgical site with a grasping instrument 900. FIG. 52 illustrates the withdrawal of the diseased specimen 1508 into the sleeve 1570 in the retrieval tool 1560. Once the specimen 1508 has been received within the sleeve 1570, the surgeon may cinch the opening 1572 closed by pulling on the cinch cord 1574.

Figure 53:
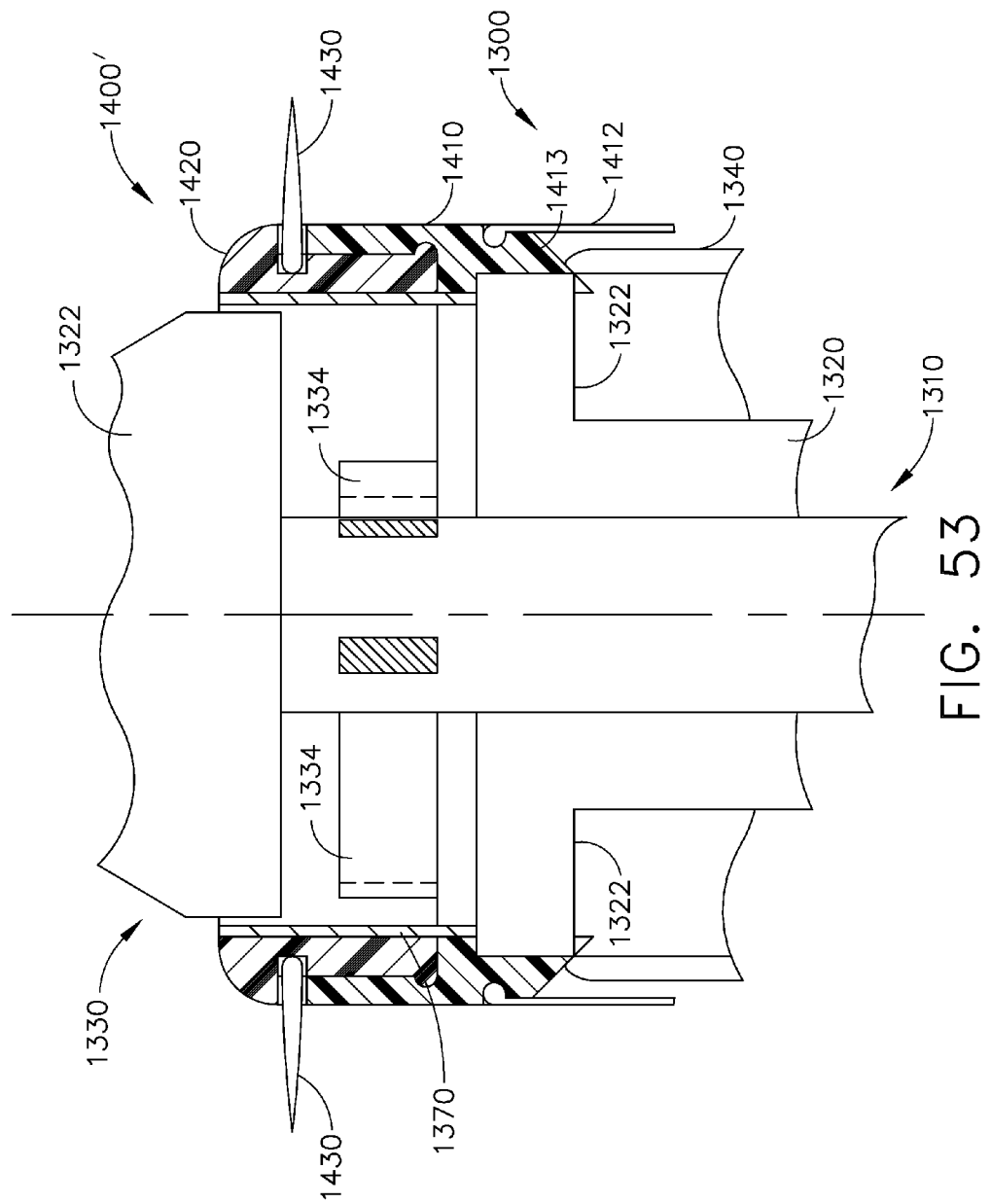
FIG. 53 is a partial cross-sectional view of another universal port embodiment of the present invention.

Referring again to FIG. 36, the outer ring portion 1410 and/or the inner ring portion 1420 of the universal port arrangement 1400 can be comprised of a rigid material. In at least one embodiment, the ring portion 1410 and/or the ring portion 1420 can be comprised of plastic, for example. FIG. 53 illustrates an alternative universal port arrangement 1400' that is substantially similar to universal port 1400, except that the inner and/or the outer ring portions 1410, 1420 are fabricated from an elastic material such as, for example, rubber. In such an embodiment, a rigid ring 1470 can be positioned within the universal port 1400' to retain the port 1400' in an expanded orientation during installation. In at least one embodiment, referring now to FIG. 41B, the rigid ring 1470 can be comprised of metal, for example, and can comprise slots 1476 which are sufficiently aligned with the slots 1426 defined in the inner ring 1420 such that the second arms 1334 of the tool 1310 can extend trough the slots 1476 into the slots 1426. In at least one such embodiment, the rigid ring 1470 can be sized and configured such that it is closely received within the inner ring portion 1420 in order to hold the ring portions 1410, 1420 in their configurations when the universal port arrangement 1400' is being positioned within the patient's rectum. Thereafter, the rigid ring 1470 can be removed from the port arrangement 1400. In at least one such embodiment, referring again to FIG. 41B, the rigid ring 1470 can comprise a slot 1479 which can be configured to be engaged by a withdrawal tool. In certain embodiments, the surgeon may insert a grasping instrument up through the patient's rectum and grasp the rigid ring 1470 once the tool 1310 has been disengaged and removed from the port arrangement 1400' and it is no longer desirable to pass objects through the universal port 1400'. In any event, once the rigid ring 1470 has been removed from the universal port 1400', the flexible rings 1410, 1420 can flex inwardly and assume a collapsed position, for example. See e.g., FIG. 26.

Figure 54:
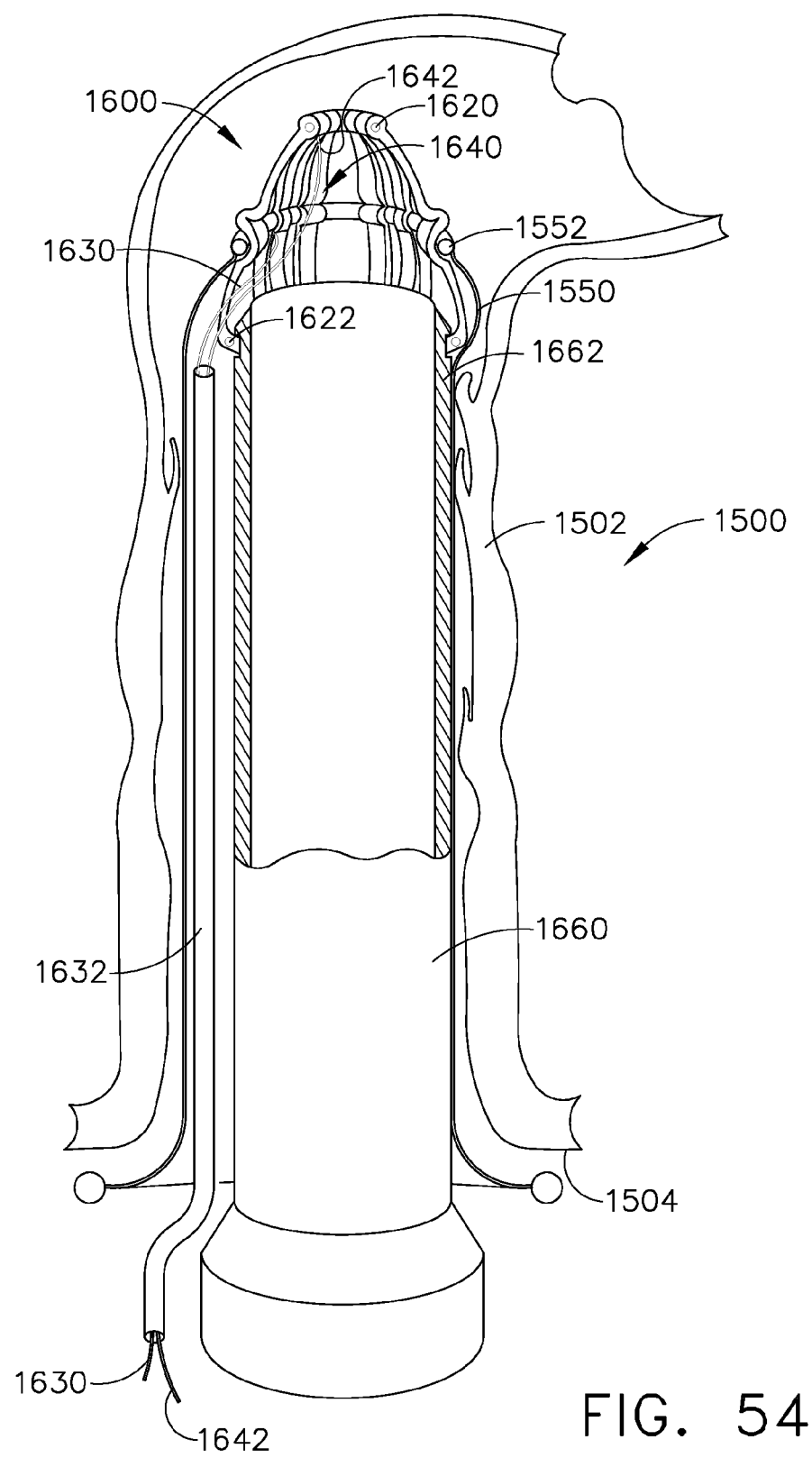
FIG. 54 is a partial cross-sectional view of another port embodiment of the present invention and insertion tube embodiment of the present invention positioned within the rectum.
Figures 55, 56:
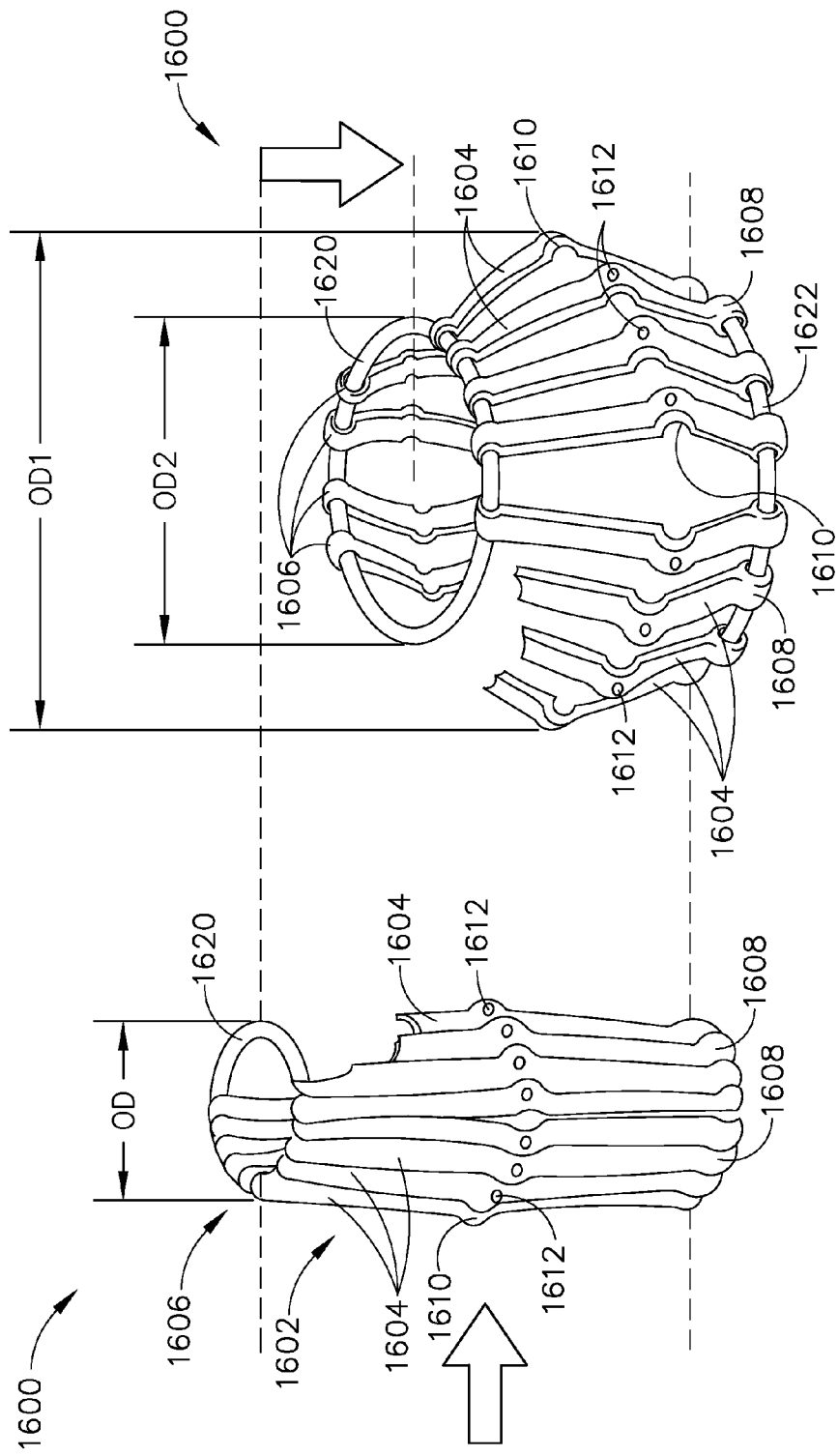
FIG. 55 is a perspective view of a portion of the port of FIG. 54 in a collapsed state.
FIG. 56 is another perspective view of the port of FIGS. 54 and 55 in an expanded state.
Figures 57, 58:
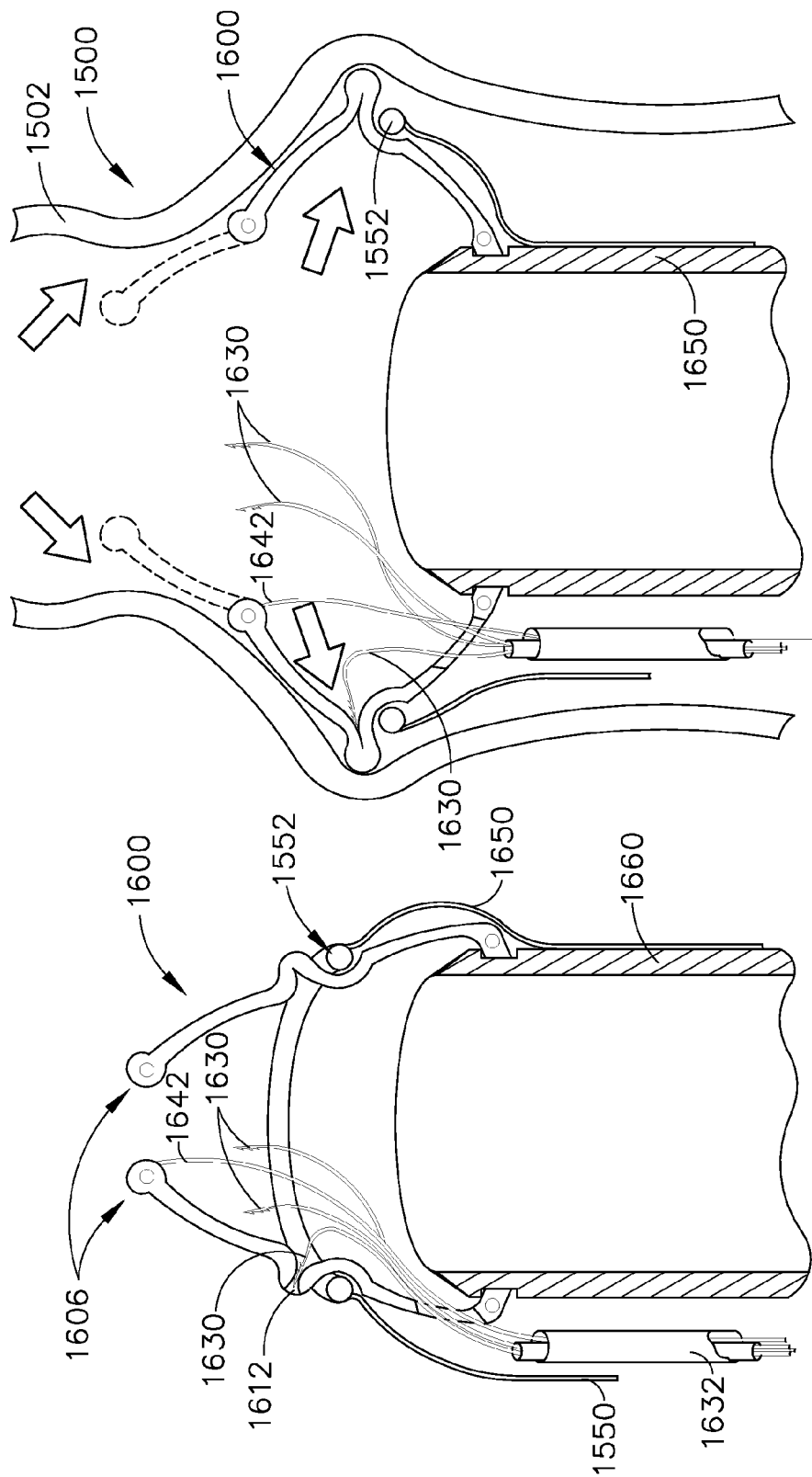
FIG. 57 is another partial cross-sectional view of the port and insertion tube embodiments of FIG. 54.
FIG. 58 is another partial cross-sectional view of the port and insertion tube of FIG. 57 inserted into a portion of the colon and illustrating deployment of the tissue retaining barbs into the colon.

FIGS. 54-60 illustrate another port 1600 embodiment of the present invention. As can be most particularly seen in FIGS. 55 and 56, the port 1600 has a body portion 1602 that is fabricated from a plurality of flexible slat member 1604. Each slat member 1604 has a distal end 1606 that is journaled on a distal ring 1620. Likewise, each slat member 1604 has a proximal end 1608 that is journaled on a proximal ring 1622. The proximal end portions 1608 are configured to releasably engage a distal end 1662 of a stiffening tube 1660. In particular, in at least one embodiment, a collection of bayonet-type slots 1664 are formed around the outer circumference of the distal end 1662 of the stiffening tube 1660. Such bayonet-type arrangement facilitates releasable attachment of the port 1600 by aligning the proximal end portions 1608 of the slat members 1604 with the slots 1664 and inserting the end portions 1608 and twisting to seat them in the slots 1604. FIG. 55 illustrates the port 1600 in its collapsed state. When in that state, the port 1600 has an outer diameter "OD" and when in an expanded state (FIG. 56), the port 1600 has an overall outer diameter "OD1". The ends of the member have an outer diameter of OD2. In one embodiment, for example, OD may be approximately 20 mm, OD1 may be approximately 65 mm and OD2 may be approximately 40 mm. However, other sizes may be employed.

As can be seen in FIGS. 55 and 56, each slat 1604 has a central portion 1610 that has a slight radius area formed therein and which has a barb deployment hole 1612 therethrough. A barbed surgical suture 1630 extends through each barb deployment hole 1612. The sutures 1630 extend through an actuator conduit 1632 as shown in FIG. 54. An actuator 1640, in the form of a tension cable 1642, is attached to the distal ring 1620. Also various embodiments employs a flexible sleeve 1650 that extends around the port body 1602 and is retained in position by an elastic band or ring 1552.

FIG. 54 illustrates use of the port 1600 and the hollow stiffening tube 1660. After the port 1600 has been attached to the distal end of the stiffening tube 1660, the sleeve 1550 is deployed to extend over the stiffening tube 1660 and the actuation conduit 1632. The entire device may then be inserted through the anus 1504 into the rectum portion 1502 of the colon 1500 and oriented in a desired position. As can be seen in FIG. 54, the sleeve 1550 also protrudes out through the anus 1504. Once the surgeon has located the port 1600 in the desired position, an actuation motion in the form of tension "T" is applied to the cable 1642 to expand the member 1600. As the port 1600 expands, the relatively stiff suture barbs 1630 protrude through the holes 1612 in the slats 1604 to engage the colon wall and thereby retain the port 1600 in position.

Figure 59:
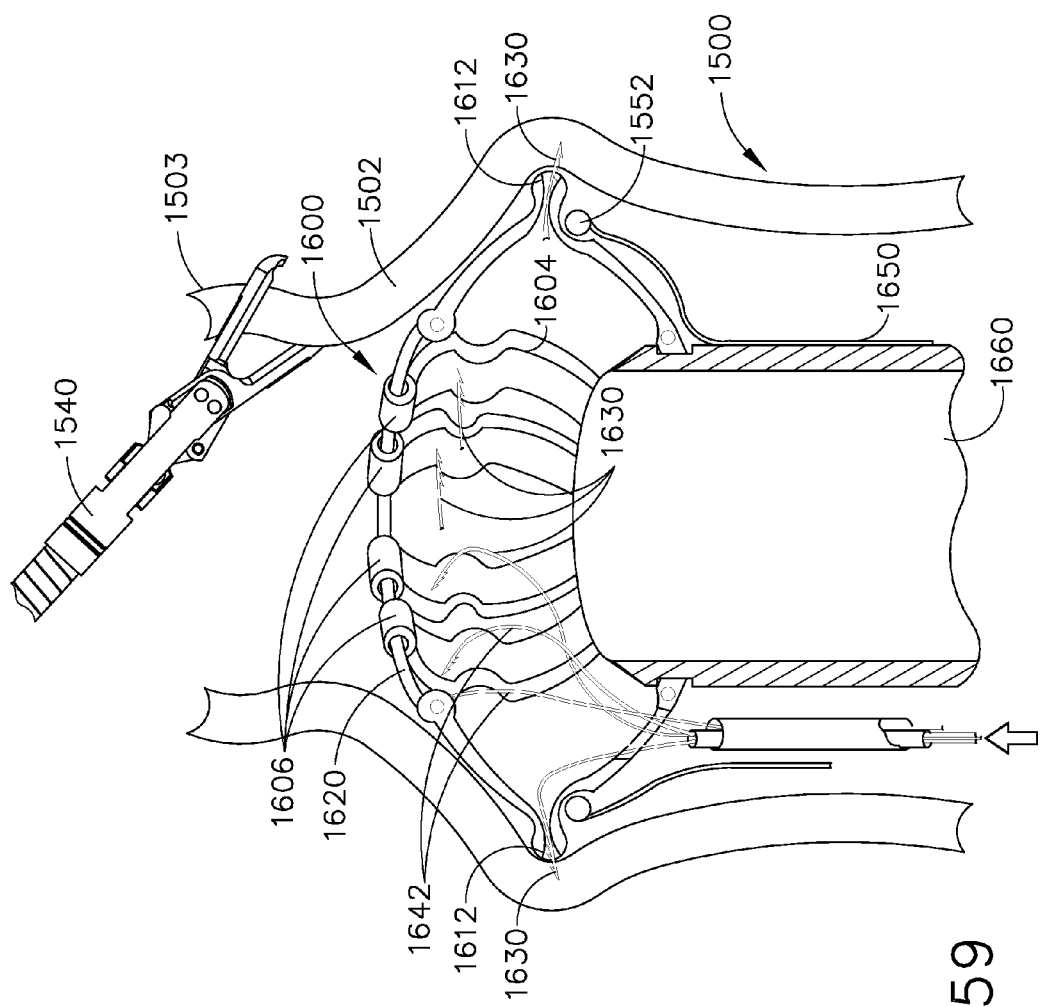
FIG. 59 is another partial cross-sectional view of the port and insertion tube of FIG. 57 deployed in a portion of the rectum and wherein a tissue cutting instrument is cutting a diseased portion of the colon from the rectum.
Figure 60:
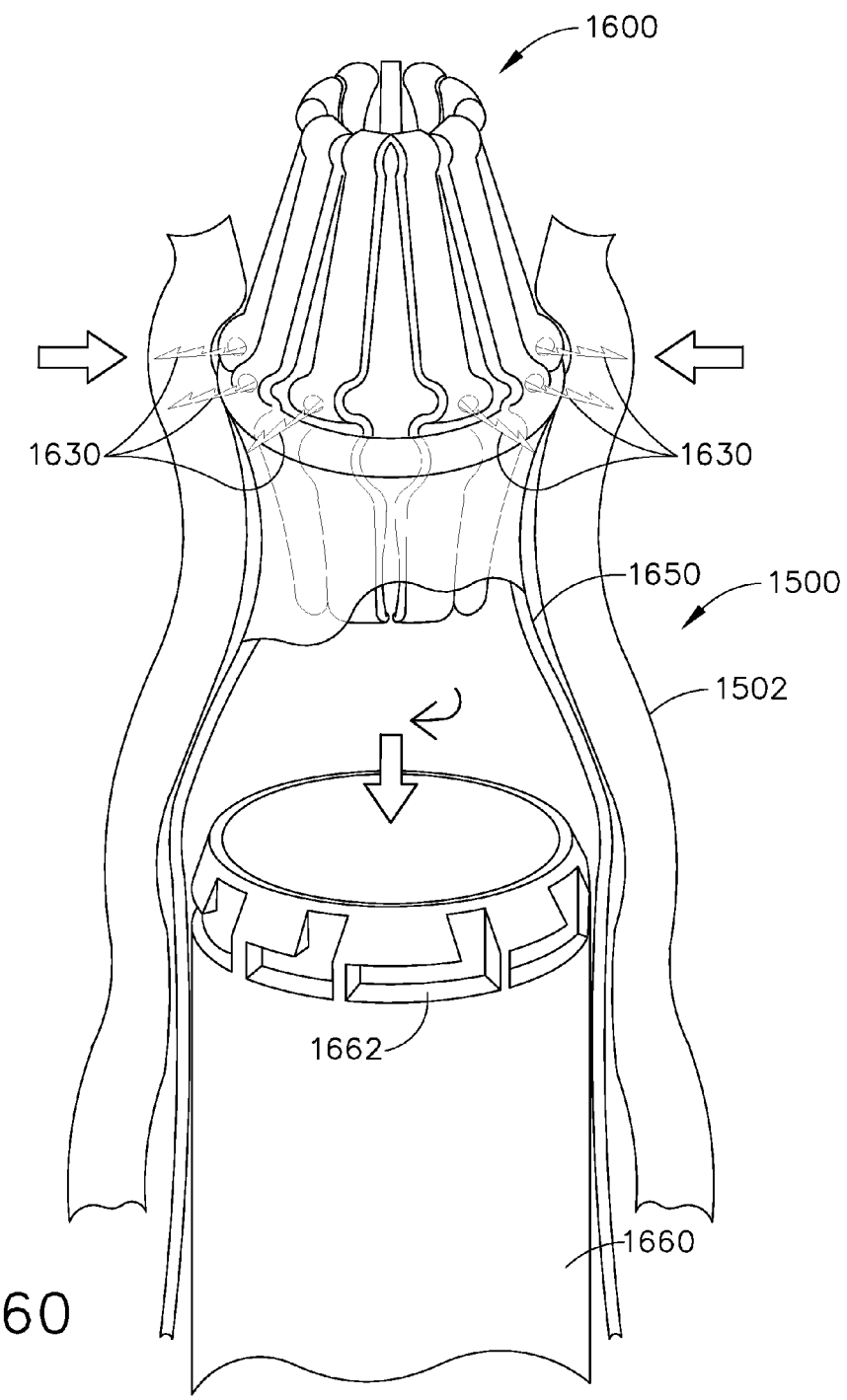
FIG. 60 is another view of the port and insertion tube of FIGS. 54-59 wherein the insertion tube has been detached from the port.

FIG. 59 illustrates use of a tissue cutting instrument 1540 to cut through the colon portion 1503 that extends between a metal clamp (not shown) and the port 1600. The surgeon may then sever the diseased portion in the various manners described above and remove them through the expanded port 1600 and out through the stiffening tube 1660. Thereafter, the surgeon may detach the stiffening tube 1660 from the port 1600 by applying a twisting motion to disengage the bayonet-type connection to enable the stiffening tube to be separated therefrom and pulled out of the anus leaving the sleeve 1650 attached to the port 1600. As can be seen in FIG. 60 the port 1600 is permitted to collapse to enable the rectum 1502 to return down to smaller diameter.

Figure 61:
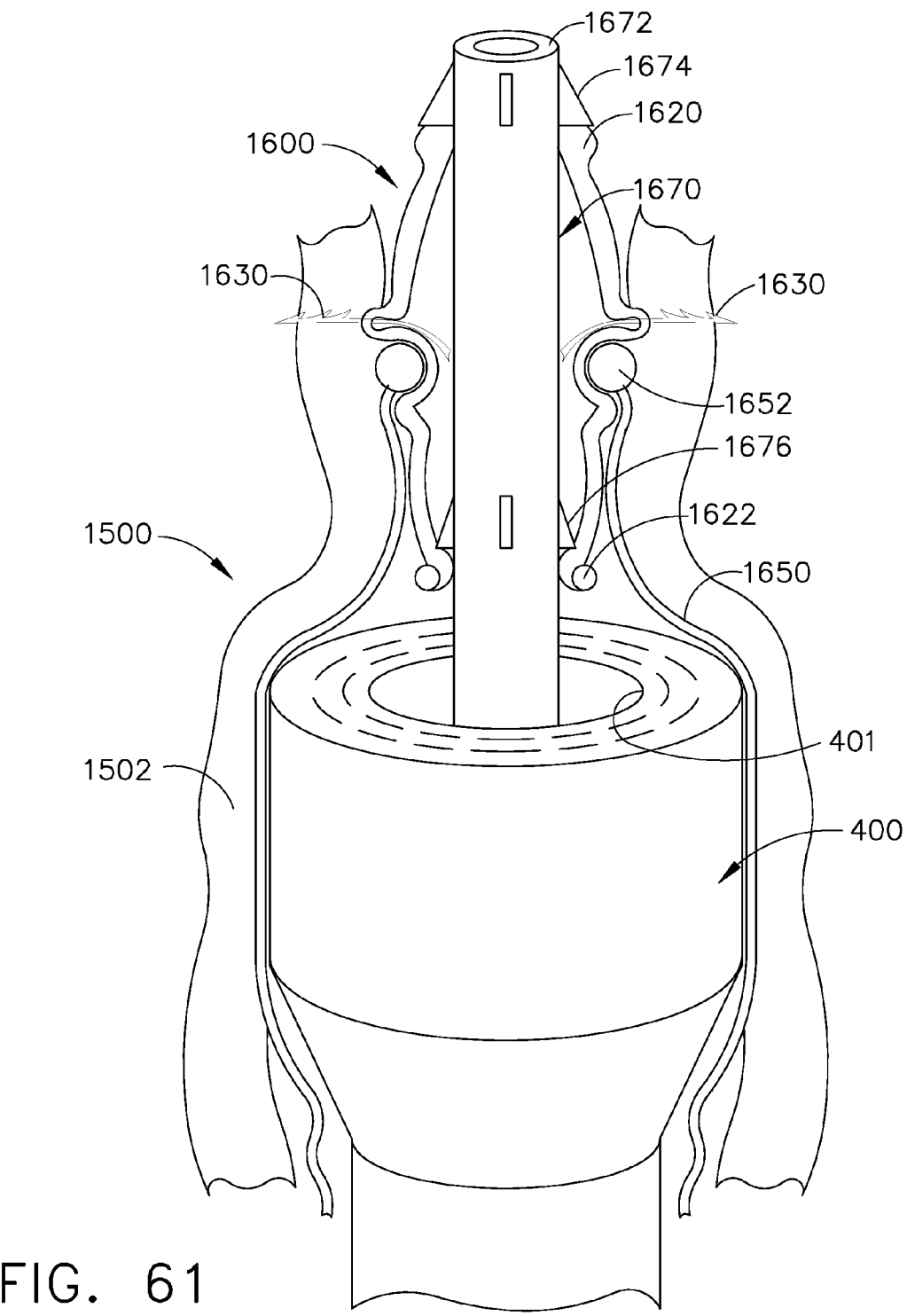
FIG. 61 is another view of the port of FIGS. 54-59 being draw into a circular stapling head embodiment of the present invention.

FIG. 61 illustrates one method of removing the port 1600 using the surgical tool 10 or other surgical circular stapler arrangement. In the depicted embodiment, a retraction adapter shaft 1670 is attached to the distal end 180 of the rotary drive shaft 150 using the various methods described above. The retraction adapter shaft 1670 has a plurality of distal retraction wedges 1674 radially extending from its distal end 1672. In addition, a plurality of proximal retraction wedges 1676 radially extend therefrom as shown in FIG. 61. Once the retraction adapter shaft 1670 has been attached as shown, the surgeon may insert the instrument into the rectum 1502 to the position shown in FIG. 61. As can be seen in that Figure, the distal retraction wedges 1674 are in retracting engagement with the distal ring 1620 and the proximal retraction wedges 1676 engage the proximal ring 1622. The surgeon may then use the slider switch 230 on the handle assembly 20 (FIG. 1) and, if necessary the control knob 248 to axially pull the rotary drive shaft 150 and the retraction adapter shaft 1670 proximally. Prior to pulling the adapter shaft 1670 proximally, the surgeon may attach an anvil onto the retraction adapter shaft 1670, such that the anvil gets pulled into position as the retraction adapter shaft 1670 pulls the port 1600 and attached colon tissue into the central area 401 in the stapling head 400 for example. Those or ordinary skill in the art will appreciate that such arrangement serves to draw the colon tissue into position for cutting and stapling. Thereafter, the stapling head 410 may be actuated as before.

Figure 63:
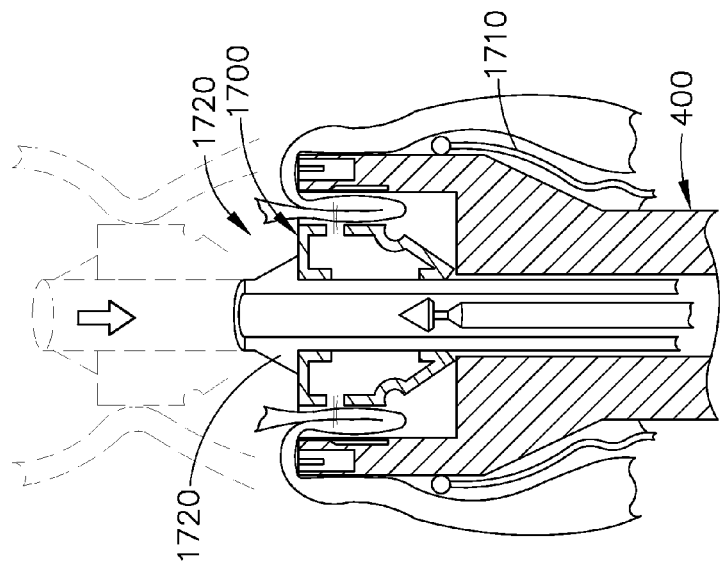
FIG. 63 a partial cross-sectional view of the circular stapling head and universal port of FIG. 62 wherein the universal port has been drawn into the circular stapling head.
Figure 62:
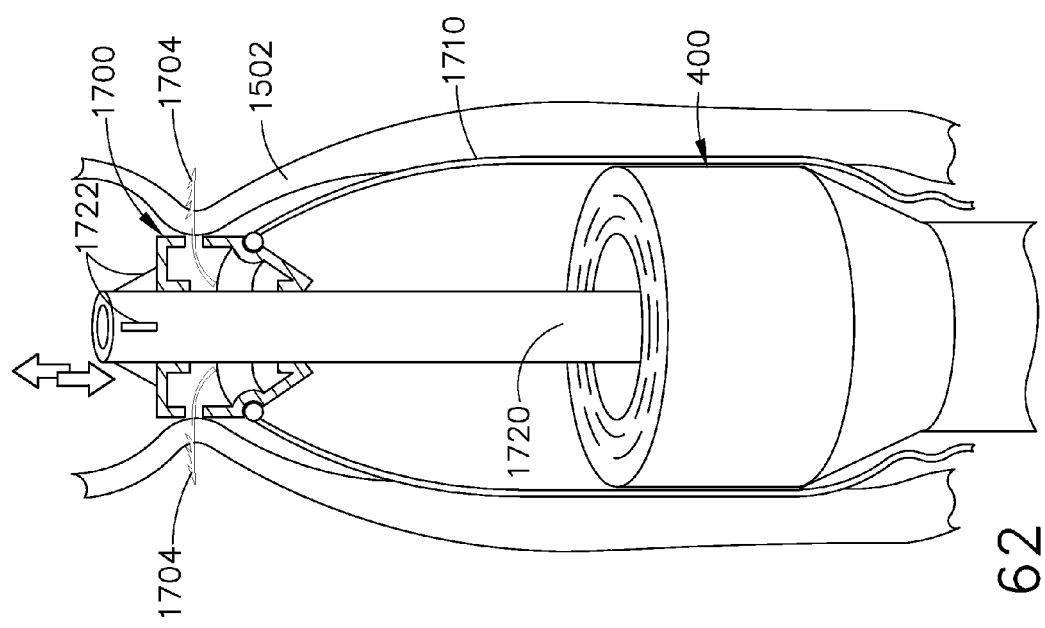
FIG. 62 is a partial perspective view of another universal port embodiment of the present invention installed within the colon and being engaged by a circular stapling head embodiment of the present invention.

FIGS. 62 and 63 illustrate an alternate port 1700 that has a body portion 1702 with a plurality of suture barbs 1704 protruding therefrom that has been attached to the rectum 1502 as shown. The port 1700 also has a flexible sleeve 1710 attached thereto. This embodiment also employs a retraction adapter shaft 1720 that has distal retraction wedges 1722 thereon. The surgical instrument 10 is otherwise used as described above to draw the port 1700 into the stapling head 400 as shown. As the port 1700 is drawn into the stapling head 400, the surgeon pulls on the sleeve 1710 such that it disengages from the port 1700 and assumes a position around the stapling head 400. See FIG. 63.

Figure 64:
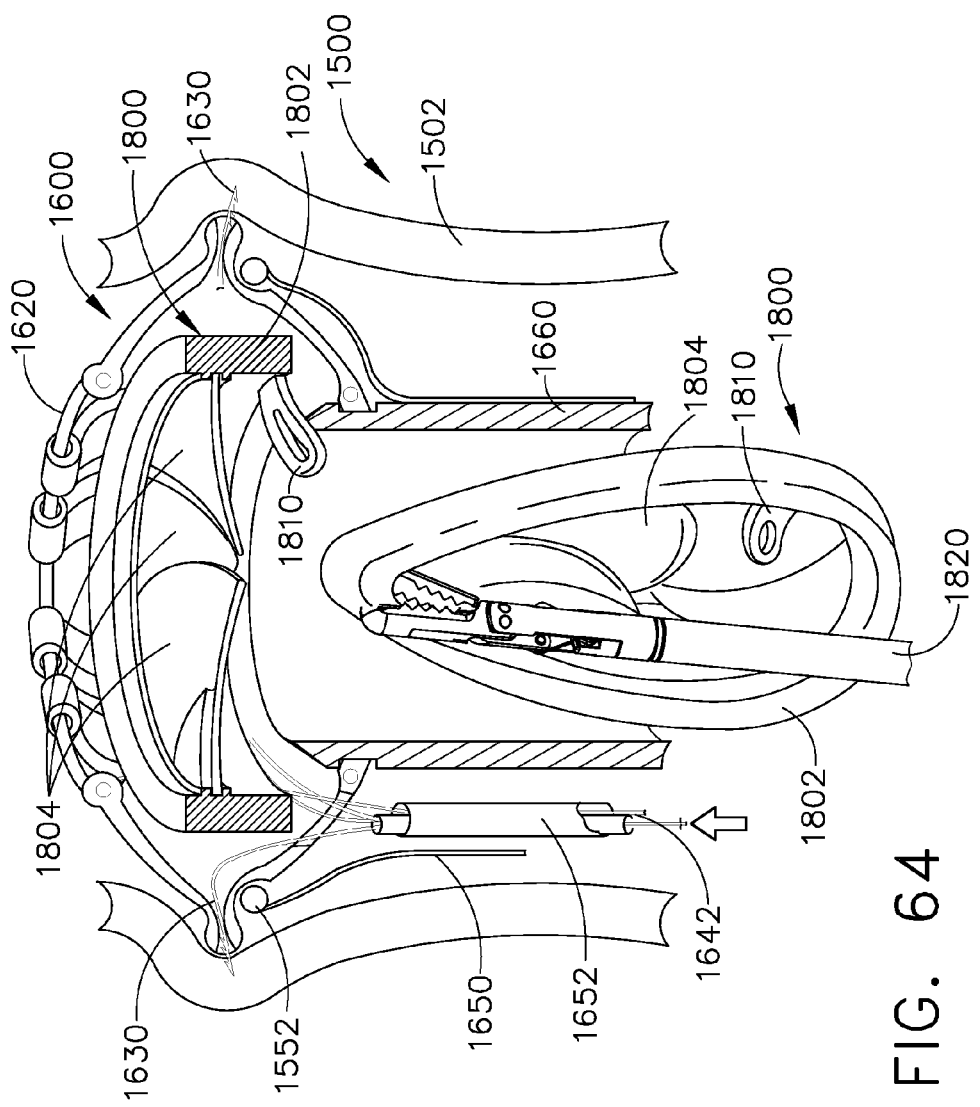
FIG. 64 is another perspective view of a port and insertion tube embodiment of the present invention installed with the colon and wherein a grasping instrument is used to introduce and insert a flexible port member embodiment therein.

FIG. 64 illustrates use of a flexible port member 1800 in connection with a port 1600. As can be see in that Figure, the port member 1800 has a flexible outer ring 1802 that has a plurality of overlapping spirally arranged flaps or petal-like members 1806 that serve to close the central area 1804 defined by the ring 1802, yet permit the passage of objects therethrough. To install the port member 1800 into the port 1600, the surgeon may employ a grasping instrument 1820 to insert the port member 1800 into the stiffener shaft 1660 and into the central area of the expanded port 1600. The port member 1800 may also include a retrieval tab 1810 to enable the surgeon to remove the port member 1800 with the grasping instrument 1820.

One of the challenges facing surgeons when performing colorectal surgery is the difficulty in making the transection in tight and angulated spaces. Limited visualization, as well as the magnitudes of the forces that may generally be required to transect and seal the colon, add to those challenges. Rather than use a mechanical structure to dilate the head of a modular circular stapler, the tissue manipulation device 1900 of the present invention uses a vacuum to draw the colon down to the shaft diameter. With the colon tissue bound to the vacuum shaft, the manipulation of the shaft can then facilitate relative easy movement of the colon for dissection.

As can be seen in FIGS. 65 and 66, the tissue manipulation device 1900, according to at least one embodiment includes a hollow outer shaft 1902 that rotatably supports a vacuum shaft 1910 thereon. The hollow outer shaft 1902 is substantially rigid and is designed to be inserted into the rigid shaft portion 1952 of a ring installation instrument 1950 as will be discussed in further detail below. The vacuum shaft 1910 comprises a proximal attachment collar 1912 that is rotatably affixed to the distal end 1904 of the outer shaft 1902. A seal 1906 is provided between the distal end 1904 of the outer shaft 1902 and the proximal attachment collar 1912. The collar 1912 interfaces with a vacuum supply tube 1914 that is attached to a source of vacuum 1916.

In various embodiments, the vacuum shaft 1910 has a screen section 1918 therein that is attached to the attachment collar 1912. The screen mesh may comprise stainless steel, titanium, etc. mesh. In at least one embodiment, the screen mesh may be constructed of two layers of screen at a 45 degree rotation to one another in an effort minimize any likelihood of clogging with tissue. The distal end of the screen section 1918 is attached to a seal ring 1920 that is configured to establish a sliding and rotating seal with a central drive shaft member 1930. As shown in FIGS. 65 and 66, flexible head member 1932 is attached to the distal end 1931 of the drive shaft 1930. The flexible head 1932 may be fabricated from rubber or other flexible material and have a slight bias as shown. Such arrangement enables the surgeon to better manipulate portions of the colon during installation and positioning of the instrument 1900. However, other head configurations could be use. The drive shaft 1930 extends through the outer shaft 1902 and interfaces with a handle or other arrangement that enables the surgeon to apply rotary and axial motions thereto.

As indicated above, the tissue manipulation device 1900 may be used in connection with a ring installation instrument 1950. As can be seen in FIGS. 65 and 66, the ring installation instrument 1950 includes a shaft 1952 that has a distal end 1954 that is configured to slidably support an elastic anastomosis ring 1960 thereon. The distal end 1954 of the shaft 1952 further includes a ring deployment member 1956 that is attached to a push rod 1970 that extends through the wall of shaft 1952.

The tissue manipulation device 1900 may be used as follows. The surgeon first inserts the ring installation instrument 1950 into the rectum through the patient's anus. Thereafter the tissue manipulation instrument 1900 is inserted through the shaft 1952 and into the colon. The surgeon may then apply an axial motion to the drive shaft 1930 to push a portion of the drive shaft 1930 out of the screened section 1918 to manipulate the colon into a desirable position. The vacuum shaft 1910 is also advanced distally out of the shaft 1952 to enable the target tissue "TT" to be retrieved. Once the screen section 1918 is positioned adjacent to the target tissue "TT", the surgeon may then apply the vacuum thereto to draw the target tissue "TT" onto the screen section 1918. Thereafter the vacuum shaft 1910 is drawn back into the outer shaft 1902 and the shaft 1952 of the ring installation instrument 1950. Such action causes the target tissue "TT" to fold over between the screen section 1918 and the inner wall of the shaft 1952 as shown. Once the target tissue "TT" is positioned between the screen section 1918 the shaft 1952, the surgeon may then apply a pushing motion to the push rod 1970 to axially advance the ring deployment member in the distal direction to push the anastomosis ring 1960 off of the distal end of the shaft 1952 as shown in FIG. 66.

Figure 67:
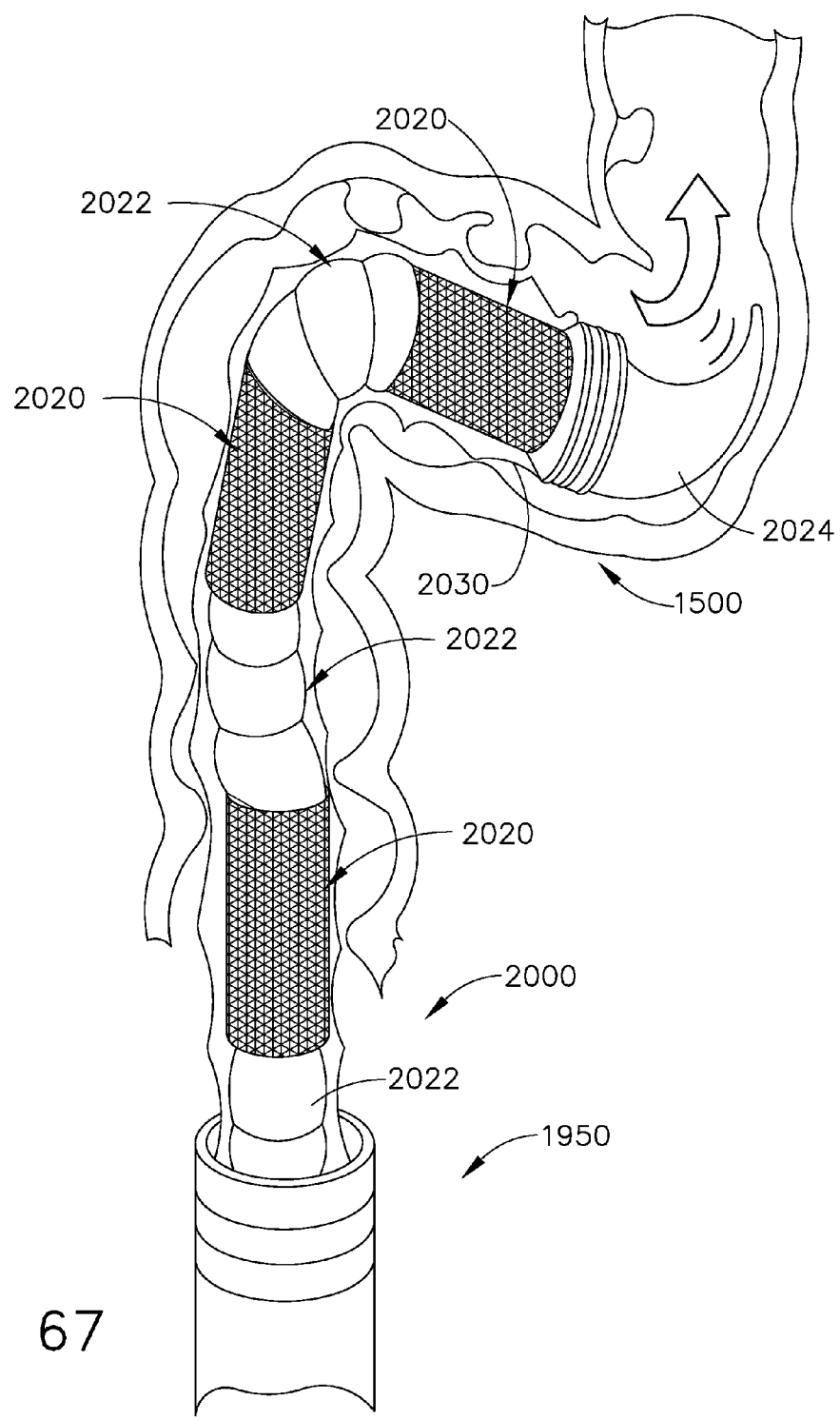
FIG. 67 is a partial perspective view of another tissue manipulation device embodiment of the present invention inserted into the colon.

FIG. 67 illustrates another vacuum shaft embodiment 2000 of the present invention. In at least one form, the vacuum shaft 2000 has a central shaft portion 2010 that has three screen sections 2020 that are interconnected by flexible joints 2022. The distal end of the shaft portion 2010 has a flexible head portion 2024. An outer sleeve 2030 may be employed to facilitate ease of insertion and when the shaft 2000 has been properly located the user may withdraw the sleeve 2030 from the device exposing the screen sections 2020. The screen sections communicate with a source of vacuum as was described above to enable the portions of the colon 1500 to be drawn into engagement therewith to facilitate better manipulation of the colon 1500.

Figure 68:
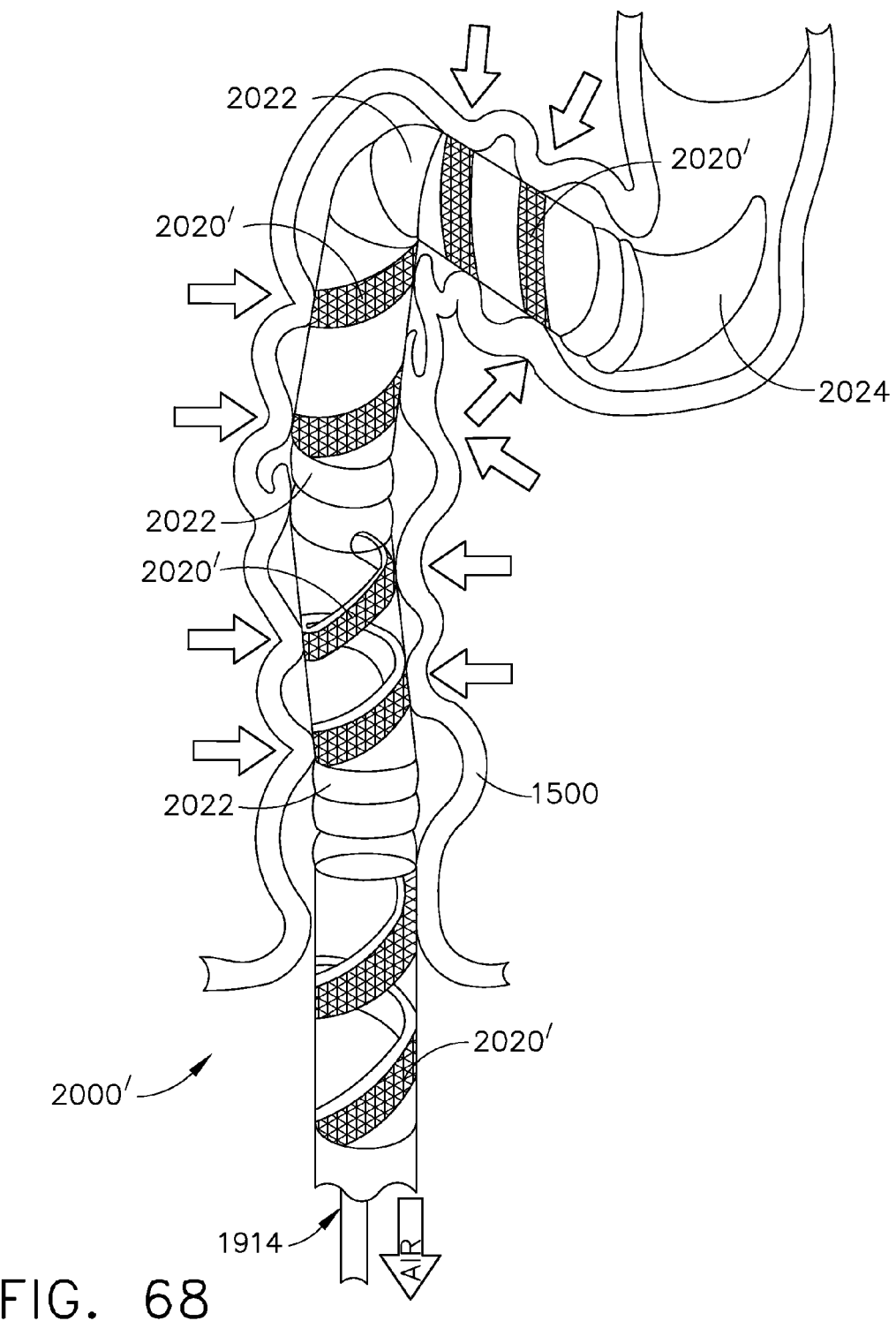
FIG. 68 is a partial perspective view of another tissue manipulation device embodiment of the present invention inserted into the colon.

FIG. 68 illustrates a vacuum shaft embodiment 2000' that employs spirally arranged screen sections 2020' that communicate with a source of vacuum. As the tissue is drawn into contact with the screen sections 2020' the air in the colon is permitted to exit out the vacuum shaft 2000'.

The various embodiments of the present invention represent a vast improvement over prior surgical methods and devices used to perform colorectal surgery. While several embodiments of the invention have been described, it should be apparent, however, that various modifications, alterations and adaptations to those embodiments may occur to persons skilled in the art with the attainment of some or all of the advantages of the invention. For example, according to various embodiments, a single component may be replaced by multiple components, and multiple components may be replaced by a single component, to perform a given function or functions. This application is therefore intended to cover all such modifications, alterations and adaptations without departing from the scope and spirit of the disclosed invention as defined by the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The invention which is intended to be protected is not to be construed as limited to the particular embodiments disclosed. The embodiments are therefore to be regarded as illustrative rather than restrictive. Variations and changes may be made by others without departing from the spirit of the present invention. Accordingly, it is expressly intended that all such equivalents, variations and changes which fall within the spirit and scope of the present invention as defined in the claims be embraced thereby.

What is claimed is:

1. A universal port for insertion into a colon, said universal port comprising:
   an expandable portion configured to be selectively expanded from a collapsed insertion state to an expanded state upon the application of a first rotary drive motion thereto, wherein said expandable portion is configured to engage the colon in said expanded state, said expandable portion comprising:
   a first expandable hub assembly that is configured to move from a collapsed position to an expanded position upon the application of said first rotary drive motion thereto;
   a second expandable hub assembly operably coupled to said first expandable hub assembly for rotational motion relative thereto, said second expandable hub assembly configured to move from a second collapsed insertion state to a second expanded state upon application of a second rotary drive motion thereto, said second expandable hub assembly operably supporting a plurality of tissue-engaging members configured to move from un-deployed positions to deployed tissue-engaging positions when said second expandable hub assembly is moved from said second collapsed insertion state to said second expanded state; and
   an expandable outer ring operably supported on said first expandable hub assembly and wherein said universal port further comprises a drive portion configured to engage said expandable portion and apply said first rotary drive motion to said expandable portion.

2. The universal port of claim 1 wherein said expandable portion further comprises a third expandable hub assembly that is operably coupled to said second expandable hub assembly for rotational motion relative thereto, said third expandable hub assembly configured to move from a third collapsed insertion state to a third expanded state upon application of a third rotary drive motion thereto, said third expandable hub assembly operably supporting a plurality of tissue cutting members configured to move from un-deployed positions to deployed tissue cutting positions when said third expandable hub assembly is moved from said third collapsed insertion state to said third expanded state.

3. The universal port of claim 1 further comprising a flexible sleeve attached to said universal port to form an insertion and exit passage extending therefrom.

4. The universal port of claim 1 further comprising an occlusion cover operably attached to said universal port.

5. The universal port of claim 4 wherein said occlusion cover comprises a segmented diaphragm assembly.

6. The universal port of claim 1 further comprising a seal selectively engageable with said expandable portion.

7. The universal port of claim 1 wherein said drive portion is disengageable from said expandable portion.

8. The universal port of claim 1 wherein said drive portion is configured to be engaged to a distal end of an elongated shaft assembly of a modular surgical instrument configured to selectively supply said first rotary drive motion thereto.

9. A universal port for insertion into a colon, said universal port comprising:
   an annular port body defining a centrally-disposed port therethrough;
   a plurality of tissue-engaging barbs operably supported within said annular port body and configured for movement from a first insertion position within said annular port body to a second deployed position wherein a tissue-engaging portion thereof protrudes outward from said annular port body; and a deployment drive assembly operably supported within said annular port body and configured for operable engagement with a surgical instrument, said deployment drive assembly operably interfacing with each of said tissue-engaging barbs such that upon application of a drive motion from the surgical instrument in a first direction causes said tissue-engaging barbs to move from said first insertion position to said second deployed position and upon another application of said drive motion from the surgical instrument in a second direction causes said tissue-engaging barbs to move from said second deployed position to said first insertion position.

10. The universal port of claim 9 wherein said drive motion comprises an axial drive motion.

11. The universal port of claim 10 wherein said deployment drive assembly comprises:

a rotary drive hub rotatably supported within said annular port body, said rotary drive hub having an inner bore wall that has a pair of helical drive slots therein, said rotary drive hub further having a drive gear formed thereon configured for meshing engagement with gear portions on each of said tissue-engaging barb; and a drive shaft extension configured for releasable engagement with a rotary drive shaft of the surgical instrument, said drive shaft extension having a pair of drive pins protruding therefrom adapted to be received in a corresponding one of said helical drive slots.

12. A universal port for installation within a colon, said universal port comprising:

a first annular port body configured to be releasably inserted within the colon by an insertion member; and a second annular port body movably coupled to said first annular port body, said second annular port body configured for releasable operable engagement with a drive member for applying drive motions thereto, said second annular port body operably supporting a plurality of tissue-engaging barbs around a circumference of said second annular port body, each said tissue-engaging barb being selectively deployable from an insertion position wherein each said tissue-engaging barb is supported substantially within said second annular port body and a deployed position wherein tissue-engaging tip portions thereof protrude outward from second annular port body.

13. The universal port of claim 12 wherein said second annular port body is rotatably attached to said first annular port body for relative rotation thereto upon application of a rotary drive motion thereto by said drive member.

14. The universal port of claim 13 wherein said insertion member comprises an insertion shaft portion of a surgical instrument, said insertion shaft portion configured for releasable engagement with said first annular port body and wherein said drive member comprises a rotary drive shaft assembly comprising a rotary drive shaft rotatably supported within said insertion shaft portion and having a distal end protruding therefrom and a proximal portion configured to operably interface with an actuation system of the surgical instrument such that upon application of an actuation motion thereto, said actuation system causes said rotary drive shaft to apply said rotary drive motion.

15. The universal port of claim 14 wherein said first annular port body has a first inner port wall having a plurality of first slot formations therein configured to releasably receive corresponding first support arms protruding from said insertion shaft portion and wherein said second annular port body has a second inner port wall that has a plurality of second slot formations therein configured to releasably receive corresponding second support arms protruding from said rotary drive shaft assembly.

16. The universal port of claim 15 wherein said distal end of said rotary drive shaft has a blunt distal end that protrudes distally beyond said second annular port body when said second support arms are seated within said second slot formations in said second annular port body.

17. The universal port of claim 12 further comprising a flexible sleeve attached to said universal port to form an insertion and exit passage extending therefrom.

18. A colon expansion port for installation within a colon, said colon expansion portion comprising:

a port body having a proximal port end, a distal port end and a central portion extending therebetween, said port body being selectively configurable from a collapsed insertion position and an expanded installation position;

an insertion instrument releasably attachable to said proximal port end of said port body;

an actuation member interfacing with said distal port end of said port body to apply an actuation motion thereto to draw said distal portion of said port body towards said proximal portion of said port body to move said port body from said collapsed insertion position to said expanded installation position; and a plurality of tissue-engaging barbs operably supported within said port body and being movable from an undeployed position to a deployed position when said actuation motion is applied to said distal port end portion of said port body.

19. A universal port for insertion into a colon, said universal port comprising:

an expandable portion configured to be selectively expanded from a collapsed insertion state to an expanded state upon the application of a rotary drive motion thereto, wherein said expandable portion is configured to engage the colon in said expanded state;

a drive portion configured to engage said expandable portion and apply said rotary drive motion to said expandable portion; and a flexible sleeve attached to said universal port to form an insertion and exit passage extending therefrom.

20. A universal port for insertion into a colon, said universal port comprising:

an expandable portion configured to be selectively expanded from a collapsed insertion state to an expanded state upon the application of a rotary drive motion thereto, wherein said expandable portion is configured to engage the colon in said expanded state;

a drive portion configured to engage said expandable portion and apply said rotary drive motion to said expandable portion; and an occlusion cover operably attached to said universal port.

21. The universal port of claim 20 wherein said occlusion cover comprises a segmented diaphragm assembly.

22. A universal port for insertion into a colon, said universal port comprising:

an expandable portion configured to be selectively expanded from a collapsed insertion state to an expanded state upon the application of a rotary drive motion thereto, wherein said expandable portion is configured to engage the colon in said expanded state;

a drive portion configured to engage said expandable portion and apply said rotary drive motion to said expandable portion; and a seal selectively engageable with said expandable portion.

23. A universal port for insertion into a colon, said universal port comprising:
- an expandable portion configured to be selectively expanded from a collapsed insertion state to an expanded state upon the application of a rotary drive motion thereto, wherein said expandable portion is configured to engage the colon in said expanded state; and
- a drive portion configured to engage said expandable portion and apply said rotary drive motion to said expandable portion and being further configured to be disengaged from said expandable portion.

24. A universal port for insertion into a colon, said universal port comprising:
- an expandable portion configured to be selectively expanded from a collapsed insertion state to an expanded state upon the application of a rotary drive motion thereto, wherein said expandable portion is configured to engage the colon in said expanded state; and
- a drive portion configured to be engage to a distal end of an elongated shaft assembly of a modular surgical instrument configured to selectively supply said rotary drive motion thereto, said drive portion further configured to apply said rotary drive motion to said expandable portion.

* * * * *